(12) United States Patent
Simaan et al.

(10) Patent No.: US 10,300,599 B2
(45) Date of Patent: May 28, 2019

(54) SYSTEMS AND METHODS FOR SAFE COMPLIANT INSERTION AND HYBRID FORCE/MOTION TELEMANIPULATION OF CONTINUUM ROBOTS

(71) Applicants: Vanderbilt University, Nashville, TN (US); Roger E. Goldman, New York, NY (US)

(72) Inventors: Nabil Simaan, Nashville, TN (US); Andrea Bajo, Fort Lauderdale, FL (US); James L. Netterville, Nashville, TN (US); C. Gaelyn Garrett, Nashville, TN (US); Roger E. Goldman, New York, NY (US)

(73) Assignee: Vanderbilt University, Nashville, TN (US)

( * ) Notice: Subject to any disclaimer, the term of this patent is extended or adjusted under 35 U.S.C. 154(b) by 157 days.

(21) Appl. No.: 15/399,902

(22) Filed: Jan. 6, 2017

(65) Prior Publication Data
US 2017/0182659 A1    Jun. 29, 2017

Related U.S. Application Data

(63) Continuation of application No. 14/271,418, filed on May 6, 2014, now Pat. No. 9,539,726, which is a (Continued)

(51) Int. Cl.
*G05B 19/04* (2006.01)
*G05B 19/18* (2006.01)
(Continued)

(52) U.S. Cl.
CPC ............ *B25J 9/1625* (2013.01); *A61B 34/30* (2016.02); *A61B 34/35* (2016.02); *A61B 34/37* (2016.02);
(Continued)

(58) Field of Classification Search
CPC ........ B25J 19/02; B25J 9/1602; Y10S 901/01; Y10S 901/30
See application file for complete search history.

(56) References Cited

U.S. PATENT DOCUMENTS 2,988,237 A * 6/1961 Devol, Jr. ............... B25J 9/1679
                                                                198/349.6
3,580,099 A * 5/1971 Mosher ................... A61F 2/604
                                                                414/1
(Continued)

FOREIGN PATENT DOCUMENTS

WO    WO-2009094670 A1 *   7/2009   ............... A61B 5/11

*Primary Examiner* — Khoi H Tran
*Assistant Examiner* — Jorge O Peche
(74) *Attorney, Agent, or Firm* — Michael Best & Friedrich LLP

(57) ABSTRACT

Methods and systems are described for controlling movement and an applied force at the tip of the continuum robot that includes a plurality of independently controlled segments along its length. An estimated force at the tip of the continuum robot is determined based on measurements of loads and positions of each segment. A reference position command and a force command are received from a user interface. The reference position command indicates a desired movement for the distal end of the continuum robot and the force command indicates a desired force to be applied by the tip of the continuum robot to a tissue surface. The position of the continuum robot is adjusted to cause the tip of the continuum robot to apply the desired force to the tissue surface based on the estimated force at the tip of the continuum robot, the reference position command, and the force command.

12 Claims, 33 Drawing Sheets

Related U.S. Application Data continuation-in-part of application No. PCT/US2013/037346, filed on Apr. 19, 2013.

(60) Provisional application No. 61/819,808, filed on May 6, 2013, provisional application No. 61/636,009, filed on Apr. 20, 2012.

(51) Int. Cl.
*B25J 9/16* (2006.01)
*A61B 34/30* (2016.01)
*A61B 34/35* (2016.01)
*A61B 34/37* (2016.01)
*A61B 90/00* (2016.01)
*A61B 17/00* (2006.01)

(52) U.S. Cl.
CPC ............ *A61B 90/06* (2016.02); *B25J 9/1602* (2013.01); *B25J 9/1633* (2013.01); *A61B 2017/00314* (2013.01); *A61B 2017/00323* (2013.01); *A61B 2034/301* (2016.02); *A61B 2034/306* (2016.02); *A61B 2090/064* (2016.02); *G05B 2219/40184* (2013.01); *G05B 2219/40299* (2013.01); *Y10S 901/01* (2013.01); *Y10S 901/30* (2013.01); *Y10S 901/50* (2013.01)

(56) References Cited

U.S. PATENT DOCUMENTS

| | | | |
|---|---|---|---|
| 4,744,264 A | 5/1988 | Milenkovic | |
| 4,795,296 A * | 1/1989 | Jau | B25J 13/02 244/223 |
| 4,802,461 A | 2/1989 | Cho | |
| 5,046,375 A * | 9/1991 | Salisbury, Jr. | B25J 9/046 414/7 |
| 5,231,989 A * | 8/1993 | Middleman | A61B 1/00165 600/434 |
| 5,337,732 A | 8/1994 | Grundfest et al. | |
| 5,345,937 A | 9/1994 | Middleman et al. | |
| 5,386,741 A * | 2/1995 | Rennex | A61M 25/01 15/104.33 |
| 5,397,323 A * | 3/1995 | Taylor | B25J 9/1065 606/130 |
| 5,410,638 A * | 4/1995 | Colgate | B25J 17/0216 700/260 |
| 5,480,406 A * | 1/1996 | Nolan | A61B 17/0469 289/1.2 |
| 5,662,587 A | 9/1997 | Grundfest et al. | |
| 5,749,828 A | 5/1998 | Solomon et al. | |
| 6,113,593 A * | 9/2000 | Tu | A61B 18/1206 600/374 |
| 6,197,017 B1 * | 3/2001 | Brock | B25J 3/04 414/5 |
| 6,309,346 B1 * | 10/2001 | Farhadi | A61B 1/00156 600/114 |
| 6,554,844 B2 * | 4/2003 | Lee | A61B 5/0084 606/1 |
| 6,669,711 B1 * | 12/2003 | Noda | A61B 17/12104 604/907 |
| 6,676,684 B1 * | 1/2004 | Morley | A61B 34/71 606/205 |
| 6,692,485 B1 * | 2/2004 | Brock | B25J 3/04 414/5 |
| 6,817,974 B2 | 11/2004 | Cooper et al. | |
| 6,837,892 B2 * | 1/2005 | Shoham | A61B 17/1757 606/130 |
| 6,843,793 B2 * | 1/2005 | Brock | A61B 34/20 600/424 |
| 6,858,005 B2 * | 2/2005 | Ohline | A61B 1/0053 600/139 |
| 6,860,878 B2 * | 3/2005 | Brock | A61B 5/04 606/1 |
| 6,949,106 B2 * | 9/2005 | Brock | A61B 17/0469 606/130 |
| 7,021,173 B2 * | 4/2006 | Stoianovici | B25J 9/06 74/490.03 |
| 7,099,745 B2 | 8/2006 | Ebert | |
| 7,214,230 B2 * | 5/2007 | Brock | A61B 17/0469 606/139 |
| 7,235,089 B1 * | 6/2007 | McGuckin, Jr. | A61B 17/00234 227/180.1 |
| 7,316,681 B2 * | 1/2008 | Madhani | A61B 17/00234 606/1 |
| 7,391,173 B2 * | 6/2008 | Schena | G11B 15/60 318/34 |
| 7,682,319 B2 | 3/2010 | Martin et al. | |
| 7,699,835 B2 * | 4/2010 | Lee | A61B 17/062 606/1 |
| 7,787,681 B2 | 8/2010 | Zhang et al. | |
| 7,822,249 B2 | 10/2010 | Garty et al. | |
| 7,837,615 B2 | 11/2010 | Le et al. | |
| 7,854,738 B2 * | 12/2010 | Lee | A61B 34/20 606/130 |
| 7,887,549 B2 * | 2/2011 | Wenderow | A61M 25/0113 606/108 |
| 7,959,557 B2 | 6/2011 | Weitzner et al. | |
| 8,025,635 B2 * | 9/2011 | Eaton | A61B 17/24 604/101.01 |
| 8,088,101 B2 * | 1/2012 | Chang | A61B 34/20 604/96.01 |
| 8,114,062 B2 * | 2/2012 | Muni | A61B 5/411 604/509 |
| 8,116,886 B2 | 2/2012 | Simaan et al. | |
| 8,172,828 B2 * | 5/2012 | Chang | A61B 17/24 604/509 |
| 8,303,576 B2 * | 11/2012 | Brock | A61B 34/74 600/102 |
| 8,311,626 B2 * | 11/2012 | Hlavka | A61B 34/20 600/114 |
| 8,337,521 B2 * | 12/2012 | Cooper | A61B 1/008 606/205 |
| 8,343,141 B2 | 1/2013 | Madhani et al. | |
| 8,365,633 B2 | 2/2013 | Simaan et al. | |
| 8,372,019 B2 * | 2/2013 | Goldenberg | A61B 5/6885 600/587 |
| 8,377,077 B2 * | 2/2013 | Reis | A61B 34/70 606/130 |
| 8,409,234 B2 * | 4/2013 | Stahler | A61B 34/71 606/170 |
| 8,414,505 B1 * | 4/2013 | Weitzner | A61M 25/0113 600/585 |
| 8,414,598 B2 * | 4/2013 | Brock | A61B 34/71 606/130 |
| 8,444,549 B2 * | 5/2013 | Viola | A61B 1/00158 600/117 |
| 8,460,236 B2 * | 6/2013 | Roelle | A61B 1/00149 604/523 |
| 8,480,618 B2 | 7/2013 | Wenderow et al. | |
| 8,486,053 B2 * | 7/2013 | Niemeyer | A61B 17/00234 606/1 |
| 8,498,691 B2 * | 7/2013 | Moll | A61B 17/0057 600/411 |
| 8,504,201 B2 * | 8/2013 | Moll | A61B 34/30 700/245 |
| 8,545,551 B2 * | 10/2013 | Loulmet | A61B 17/0401 606/151 |
| 8,551,115 B2 * | 10/2013 | Steger | A61B 34/30 606/1 |
| 8,585,731 B2 * | 11/2013 | Abbate | A61K 9/70 606/199 |
| 8,864,757 B2 | 10/2014 | Klimovitch et al. | |
| 2002/0120252 A1 * | 8/2002 | Brock | A61B 17/0469 606/1 |
| 2003/0120305 A1 * | 6/2003 | Jud | A61B 17/320016 606/205 |

(56) References Cited

U.S. PATENT DOCUMENTS

| | | |
|---|---|---|
| 2003/0135204 A1 | 7/2003 | Lee et al. |
| 2004/0116906 A1 | 6/2004 | Lipow |
| 2004/0176751 A1* | 9/2004 | Weitzner ............ A61B 17/0469 606/1 |
| 2005/0043718 A1* | 2/2005 | Madhani ................ B25J 9/1615 606/1 |
| 2005/0054900 A1 | 3/2005 | Mawn et al. |
| 2005/0059960 A1 | 3/2005 | Simaan et al. |
| 2005/0228440 A1* | 10/2005 | Brock ..................... A61B 34/71 606/205 |
| 2006/0036182 A1 | 2/2006 | Daniels et al. |
| 2006/0047302 A1* | 3/2006 | Ortiz ................ A61B 17/07207 606/205 |
| 2006/0058861 A1 | 3/2006 | Gibson et al. |
| 2006/0156851 A1* | 7/2006 | Jacobsen ................. B25J 18/06 74/490.01 |
| 2006/0241414 A1* | 10/2006 | Nowlin .................. A61B 34/70 600/431 |
| 2006/0258938 A1* | 11/2006 | Hoffman ............ A61B 1/00193 600/424 |
| 2007/0197939 A1* | 8/2007 | Wallace ................ A61B 5/6885 600/587 |
| 2007/0225787 A1 | 9/2007 | Simaan et al. |
| 2008/0009838 A1 | 1/2008 | Schena et al. |
| 2008/0033240 A1* | 2/2008 | Hoffman ................ A61B 90/36 600/109 |
| 2008/0065105 A1 | 3/2008 | Larkin et al. |
| 2008/0065108 A1* | 3/2008 | Diolaiti .............. A61B 1/00087 606/130 |
| 2008/0071288 A1 | 3/2008 | Larkin et al. |
| 2008/0114492 A1 | 5/2008 | Miegel et al. |
| 2008/0179301 A1 | 7/2008 | Garty et al. |
| 2008/0181473 A1 | 7/2008 | Garty et al. |
| 2008/0188800 A1* | 8/2008 | Bencini ............ A61M 25/0136 604/95.01 |
| 2008/0243063 A1 | 10/2008 | Camarillo |
| 2008/0243064 A1* | 10/2008 | Stahler ................... A61B 34/71 604/95.01 |
| 2008/0243106 A1* | 10/2008 | Coe .................. A61B 17/00234 606/1 |
| 2008/0245173 A1* | 10/2008 | Schwerin .................. B25J 9/06 74/471 XY |
| 2008/0249536 A1 | 10/2008 | Stahler et al. |
| 2008/0262513 A1 | 10/2008 | Stahler et al. |
| 2008/0302200 A1* | 12/2008 | Tobey ...................... B25J 5/007 74/490.02 |
| 2009/0054222 A1 | 2/2009 | Zhang et al. |
| 2009/0076476 A1 | 3/2009 | Barbagli et al. |
| 2009/0076521 A1 | 3/2009 | Hansen |
| 2009/0088774 A1 | 4/2009 | Swarup et al. |
| 2009/0171151 A1 | 7/2009 | Choset et al. |
| 2009/0216083 A1* | 8/2009 | Durant .................. A61B 1/0055 600/130 |
| 2009/0275818 A1 | 11/2009 | Rau et al. |
| 2009/0275857 A1 | 11/2009 | Cabiri et al. |
| 2010/0010504 A1 | 1/2010 | Simaan et al. |
| 2010/0011900 A1 | 1/2010 | Burbank |
| 2010/0030377 A1 | 2/2010 | Unsworth |
| 2010/0069719 A1 | 3/2010 | Wehrheim |
| 2010/0076269 A1* | 3/2010 | Makower ................. A61B 1/233 600/178 |
| 2010/0079308 A1* | 4/2010 | Fabre ..................... G08G 5/0086 340/951 |
| 2010/0099951 A1 | 4/2010 | Laby et al. |
| 2010/0125165 A1* | 5/2010 | Torii .................. A61B 1/00045 600/106 |
| 2010/0152899 A1 | 6/2010 | Chang et al. |
| 2010/0210391 A1 | 8/2010 | Dinger |
| 2010/0256558 A1* | 10/2010 | Olson .................... A61B 34/20 604/95.01 |
| 2010/0331857 A1 | 12/2010 | Doyle et al. |
| 2010/0331858 A1 | 12/2010 | Simaan et al. |
| 2011/0015649 A1 | 1/2011 | Anvari et al. |
| 2011/0066160 A1 | 3/2011 | Simaan et al. |
| 2011/0071541 A1* | 3/2011 | Prisco ................ A61B 17/3421 606/130 |
| 2011/0071542 A1 | 3/2011 | Prisco et al. |
| 2011/0071544 A1* | 3/2011 | Steger ............... A61M 25/0105 606/130 |
| 2011/0125165 A1* | 5/2011 | Simaan .................... A61F 9/007 606/130 |
| 2011/0160569 A1 | 6/2011 | Cohen et al. |
| 2011/0184241 A1 | 7/2011 | Zubiagte et al. |
| 2011/0196419 A1* | 8/2011 | Cooper ............... A61B 18/1445 606/206 |
| 2011/0213346 A1 | 9/2011 | Morley et al. |
| 2011/0230894 A1* | 9/2011 | Simaan ............... A61B 1/00183 606/130 |
| 2011/0306929 A1 | 12/2011 | Levesque et al. |
| 2011/0313243 A1* | 12/2011 | Zubiate .................. A61B 1/008 600/104 |
| 2011/0319910 A1 | 12/2011 | Roelle et al. |
| 2012/0071822 A1* | 3/2012 | Romo ...................... A61B 6/12 604/95.04 |
| 2012/0109274 A1 | 5/2012 | Simaan et al. |
| 2012/0123395 A1* | 5/2012 | Stoy .................. A61B 17/00234 606/1 |
| 2012/0241576 A1* | 9/2012 | Yu ........................ A61G 7/0503 248/231.85 |
| 2012/0253131 A1* | 10/2012 | Malkowski ........ A61B 17/3421 600/201 |
| 2012/0289946 A1* | 11/2012 | Steger .................... A61B 17/29 606/1 |
| 2013/0012928 A1 | 1/2013 | Cooper et al. |
| 2013/0023859 A1* | 1/2013 | Malkowski ...... A61B 17/00234 606/1 |
| 2013/0090763 A1* | 4/2013 | Simaan ..................... A61B 5/11 700/258 |
| 2013/0096540 A1 | 4/2013 | Cooper et al. |
| 2013/0110131 A1 | 5/2013 | Madhani et al. |
| 2013/0131868 A1* | 5/2013 | Rucker .................. B25J 9/1625 700/262 |
| 2013/0165869 A1 | 6/2013 | Blumenkranz ...... B25J 15/0009 604/264 |
| 2013/0165945 A9* | 6/2013 | Roelle .................... A61B 34/71 606/130 |
| 2013/0178838 A1* | 7/2013 | Malkowski ............. A61B 17/00 606/1 |
| 2013/0190741 A1* | 7/2013 | Moll .................... A61B 1/00082 606/13 |
| 2013/0197539 A1 | 8/2013 | Simaan et al. |
| 2013/0218141 A1* | 8/2013 | Hinman .................. A61B 1/008 606/1 |
| 2013/0231529 A1* | 9/2013 | John ..................... A61B 17/24 600/104 |
| 2013/0269109 A1 | 10/2013 | Yu |
| 2013/0274715 A1* | 10/2013 | Chan ..................... A61M 25/10 604/514 |
| 2013/0289581 A1* | 10/2013 | Yeung ............... A61B 17/00234 606/130 |
| 2013/0300537 A1 | 11/2013 | Bajo et al. |
| 2013/0303945 A1* | 11/2013 | Blumenkranz ... A61M 25/0067 600/585 |
| 2013/0306112 A1* | 11/2013 | Blumenkranz ........ A61B 34/30 134/34 |
| 2013/0338433 A1 | 12/2013 | Goldman et al. |
| 2014/0058406 A1* | 2/2014 | Tsekos .................. A61B 34/30 606/130 |
| 2014/0316434 A1 | 10/2014 | Simaan et al. |
| 2014/0330432 A1 | 11/2014 | Simaan et al. |
| 2015/0073434 A1 | 3/2015 | Simaan et al. |

* cited by examiner

| | Mean Error [deg] | Std. Dev. [deg] |
|---|---|---|
| $\theta_1$ | 1.59 | 1.18 |
| $\delta_1$ | 1.53 | 2.70 |

| Sample | θ [deg] | δ [deg] | Force Direction | Force Mag. [N] |
|---|---|---|---|---|
| 1 | 23.58 | 45.69 | $[0.84, 0.54, 0.02]^T$ | 0.61 |
| 2 | 22.50 | 34.80 | $[0.69, 0.72, 0.09]^T$ | 0.78 |
| 3 | 13.39 | -113.87 | $[0.73, 0.67, 0.11]^T$ | 0.62 |
| 4 | 55.41 | -111.67 | $[0.81, 0.57, 0.11]^T$ | 1.29 |
| 5 | 73.61 | -39.67 | $[0.79, 0.56, -0.23]^T$ | 1.08 |
| 6 | 56.34 | -28.58 | $[0.80, 0.55, -0.23]^T$ | 1.30 |
| 7 | 90.00 | -28.58 | $[0.80, 0.55, -0.23]^T$ | 1.23 |
| 8 | 41.27 | -79.45 | $[0.89, 0.43, -0.14]^T$ | 0.96 |
| 9 | 38.44 | -1.18 | $[0.88, 0.45, -0.15]^T$ | 1.48 |
| 10 | 48.64 | -38.54 | $[0.84, 0.53, -0.11]^T$ | 1.03 |
| 11 | 34.07 | 73.03 | $[0.84, 0.53, -0.11]^T$ | 0.72 |
| 12 | 42.21 | 69.97 | $[0.84, 0.53, -0.11]^T$ | 0.80 |
| 13 | 9.54 | 61.22 | $[0.83, 0.54, -0.10]^T$ | 0.62 |
| 14 | 23.68 | 28.34 | $[0.84, 0.53, -0.10]^T$ | 0.91 |
| 15 | 53.63 | 27.93 | $[0.85, 0.52, -0.11]^T$ | 1.29 |
| 16 | 17.44 | -120.21 | $[0.87, 0.48, -0.10]^T$ | 0.74 |
| 17 | 40.92 | -74.30 | $[0.86, 0.49, -0.10]^T$ | 1.23 |
| 18 | 15.98 | -82.64 | $[0.87, 0.48, -0.09]^T$ | 0.62 |
| 19 | 50.76 | -46.08 | $[0.86, 0.50, -0.11]^T$ | 1.50 |
| 20 | 84.13 | -32.56 | $[0.85, 0.51, -0.11]^T$ | 1.10 |
| 21 | 50.62 | 0.61 | $[0.84, 0.50, -0.19]^T$ | 1.35 |
| 22 | 50.26 | 35.16 | $[0.84, 0.51, -0.19]^T$ | 1.23 |
| 23 | 29.72 | 33.82 | $[0.83, 0.52, -0.19]^T$ | 0.96 |
| 24 | 13.43 | 72.34 | $[0.83, 0.53, -0.18]^T$ | 0.62 |
| 25 | 42.72 | -80.94 | $[0.86, 0.48, -0.19]^T$ | 1.01 |
| 26 | 27.39 | -106.95 | $[0.86, 0.48, 0.18]^T$ | 0.64 |
| 27 | 20.71 | -132.31 | $[0.86, 0.48, 0.17]^T$ | 1.03 |
| 28 | 72.51 | -42.88 | $[0.86, 0.51, -0.09]^T$ | 1.11 |

*FIG. 13*

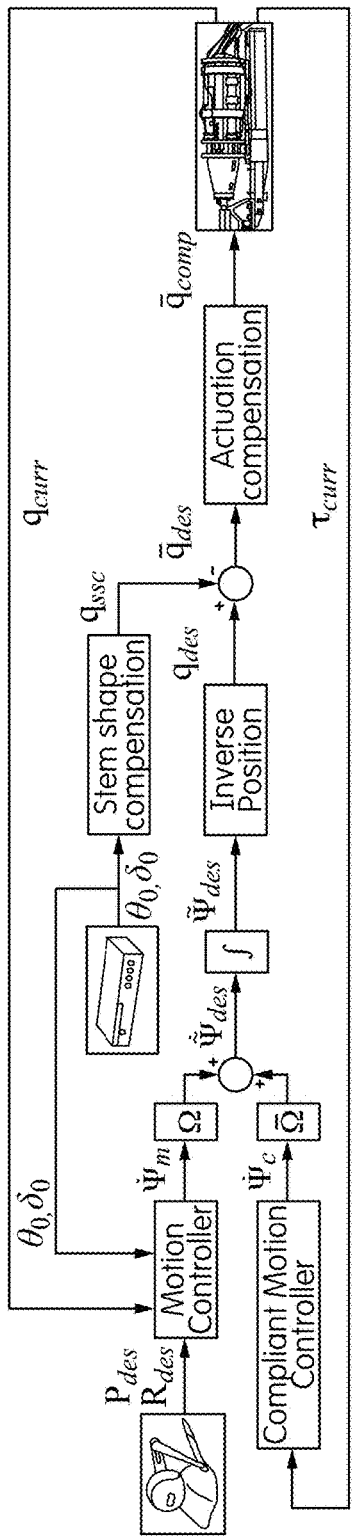
FIG. 21
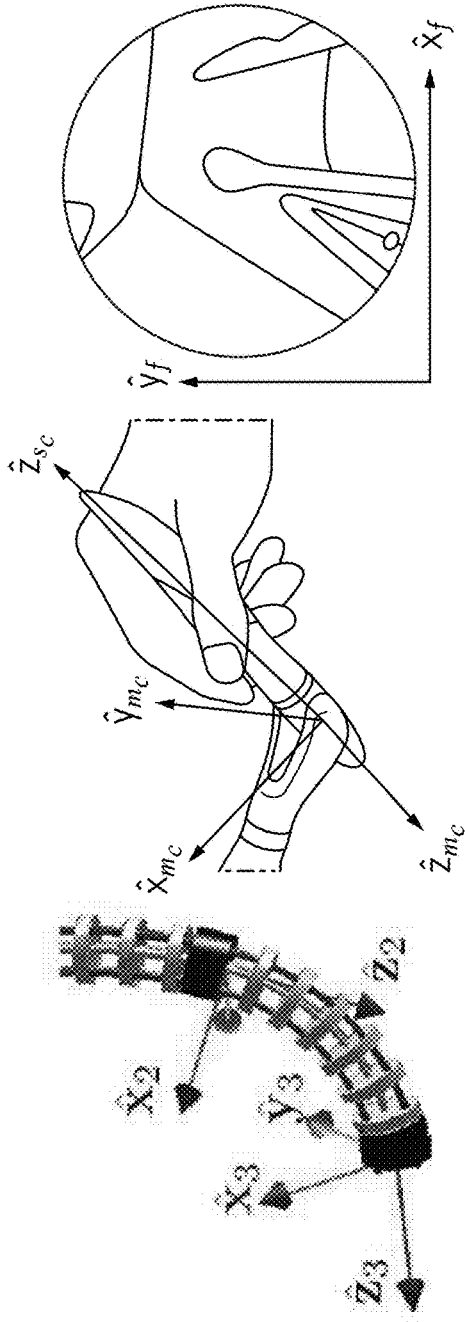
FIG. 22A
FIG. 22B
FIG. 22C

| $r$ [mm] | $L$ [mm] | $\beta$ [°] | $d$ [mm] | $E_Y$ [$N/mm^2$] | $o_d$ [mm] | $I$ [$mm^4$] |
|---|---|---|---|---|---|---|
| 1.8 | 17.5 | 120 | 13.5 | $6.5 \cdot 10^3$ | 0.3 | $3.9761 \cdot 10^{-04}$ |

FIG. 27

| $\theta$ [°] | Force [gr] | Rise Time [s] | Steady State Error [gr] |
|---|---|---|---|
| 80 | 5 | 1.11 | -0.30 |
| 80 | 10 | 1.09 | 0.60 |
| 80 | 15 | 1.04 | 1.50 |
| 60 | 5 | 1.03 | 1.30 |
| 60 | 10 | 0.77 | 3.00 |
| 60 | 15 | 0.88 | 3.00 |
| 40 | 5 | 1.35 | 1.35 |
| 40 | 10 | 1.03 | 4.30 |
| 40 | 15 | 0.67 | 4.20 |

FIG. 32

| $\theta$ [°] | Force [gr] | Rise Time [s] | Steady State Error [gr] |
|---|---|---|---|
| 80 | 10 | 0.75 | 1.90 |
| 60 | 10 | 2.72 | 4.10 |
| 40 | 10 | 1.63 | 8 |

(a) $\theta = 80°$, 10 Gr.

(b) $\theta = 60°$, 10 Gr.

(c) $\theta = 40°$, 10 Gr.

(a) Side view.

(b) Front view.

(c) Top view.

(a) Side view.

(b) Front view.

(c) Top view.

(a) Side view.

(b) Front view.

(c) Top view.

SYSTEMS AND METHODS FOR SAFE COMPLIANT INSERTION AND HYBRID FORCE/MOTION TELEMANIPULATION OF CONTINUUM ROBOTS

RELATED APPLICATIONS

This application is a continuation of U.S. patent application Ser. No. 14/271,418, filed May 6, 2014, which claims priority to U.S. Provisional Application No. 61/819,808, filed on May 6, 2013, and which is a continuation-in-part of International Patent Application No. PCT/US2013/037346, filed Apr. 19, 2013, which claims the benefit of U.S. Provisional Application No. 61/636,009, filed Apr. 20, 2012, the entire contents of all of which are incorporated herein by reference.

STATEMENT REGARDING FEDERALLY SPONSORED RESEARCH OR DEVELOPMENT

This invention was made with government support under grant IIS-1063750 awarded by the National Science Foundation. The government has certain rights in the invention.

FIELD OF THE INVENTION

The present invention relates to systems and methods of controlling the position and pose of multi-segment continuum robots. More specifically, the present invention relates to systems and methods of compliant insertion of a continuum robot into a cavity of unknown size, dimensions, and structure.

BACKGROUND OF THE INVENTION

Multi-segment continuum robots provide for snake-like movement and positioning by deformation of internal structures of the robotic mechanisms as opposed to the relative deformation of individual rigid links. As such, continuum robots can be used to extend deeper into cavities to perform functions including, for example, search and rescue in disaster relief, nuclear handling, and minimally invasive surgical procedures. However, adoption of continuum robots has been limited due to a lack of controls methods to prevent damage to the robotic structure and the environment when the device is inserted into a cavity of unknown dimensions. During insertion into a complex environment, such as a surgical or disaster site, continuum robots must interact safely while being subject to a multitude of unknown contact sites along the robot arm length.

Passive compliance techniques have been proposed to achieve safe interaction without the need for additional sensing and complex control. Passively compliant structures contain flexible members which comply with environment interaction forces without explicit compliant control. Though these systems have shown promise in providing a measure of safety, they suffer from a number of significant disadvantages for exploration and intervention in unstructured environments. By the very nature of their design, passive compliant systems are limited in their accuracy and the magnitude of forces that can be applied during environment interaction. Conversely, the measure of safety provided by passive compliance is limited by the flexibility of the system. Additionally, the compliance adds uncertainty and modeling difficulties that degrade trajectory tracking performance. Thus, a need exists for active compliant instrumentation that can safely interact with the surrounding environment while maintaining manipulation precision and delivering adequate forces for executing manipulation tasks.

SUMMARY OF THE INVENTION

The systems and methods described below allow a continuum robot system to adapt to the shape of a multi-segmented continuum robot structure to thereby adapt to the previously unknown dimensions of a cavity. The shape and position of the individual segments of the continuum robot are continually adjusted as the continuum robot is advanced further into the cavity.

International Publication No. WO 2013/158978 to Simaan et al., the entirety of which is incorporated herein by reference, describes a method of compliant insertion of a continuum robot. The continuum robot includes a plurality of independently controlled segments along a length of the continuum robot. The continuum robot is inserted into a cavity of unknown dimensions. A plurality of forces acting on the continuum robot are determined. The plurality of forces includes a force acting on each of the plurality of segments along the length of the continuum robot. Each force of the plurality of forces includes a magnitude and a direction. These forces result in a generalized force that captures the statics of the robot as described in its configuration space (a space describing the shape of each segment by two configuration space angles per a segment). Each determined generalized force is compared to a respective expected generalized force for each of the plurality of segments. The expected force for each segment is determined based on the position of the continuum robot. The position of each segment of the continuum robot is adjusted based on a difference between the determined generalized force and the expected generalized force for the segment. In some embodiments, the method further includes repeating the acts of determining the plurality of forces, comparing each determined force to a respective expected force, and adjusting the position of each segment as the continuum robot is advanced further into the cavity.

In another embodiment, the invention provides a controller for compliant insertion of a continuum robot into a cavity of unknown dimensions. The continuum robot includes a plurality of independently controlled segments along the length of the continuum robot. The controller includes a processor and memory storing instructions that are executable by the processor. The controller is configured to determine a plurality of forces acting on the continuum robot. The plurality of forces includes a generalized force acting on each of the plurality of segments along the length of the continuum robot. Each generalized force includes a magnitude and a direction. Each determined generalized force is then compared to a respective expected generalized force for each of the plurality of segments. The expected generalized force is determined based on the position of the continuum robot. The controller adjusts the position of each segment based on the difference between the determined generalized force and the expected generalized force for each of the plurality of segments.

In another embodiment, the invention provides a robotic system including a continuum robot, a plurality of actuators, and a controller. The continuum robot includes a plurality of independently controlled segments along the length of the continuum robot and a plurality of back-bone structures extending through the continuum robot. Each actuator is connected to a different one of the plurality of back-bone structures and advances or retracts the back-bone structure to control the shape and end effector position of the continuum robot. The controller includes a processor and a memory. The controller determines a plurality of forces acting on the continuum robot based on forces exerted on the plurality of back-bone structures by the plurality of actuators. The determined forces include a generalized force acting on each of the plurality of segments along the length of the continuum robot. Each generalized force includes a magnitude and a direction. The controller compares each determined generalized force to a respective expected generalized force for each of the plurality of segments. The expected generalized force is determined based on the position of the continuum robot. The position of each segment is adjusted based on the difference between the determined generalized force and the expected generalized force for each segment. The acts of determining the plurality of forces, comparing the generalized forces to a respective expected generalized force, and adjusting the position of each segment are repeated as the continuum robot is advanced into the cavity.

In some embodiments, compliant motion control of the continuum robot is provided by mapping generalized forces into a configuration space of a robot. Support vector regression techniques are used to provide sparse interpolation to estimate and cancel out effects of uncertainty in the generalized forces due to friction and uncertainty in material properties.

In some embodiments, the compliant motion control methods are used to operate rapidly deployable handheld robotic devices that are inserted into the human anatomy for surgical operations such as trans-urethral bladder resection, trans-nasal surgery, and frontal sinus exploration/surgery. In some embodiments, the methods are also used to provide impedance control of continuum robots and to enable a method for bracing the continuum robot against the anatomical features inside the cavity once contact has been localized and detected. Bracing techniques provide increased stability and increased accuracy for operations performed by a tool positioned at the distal end of the continuum robot. Collaborative telemanipulation algorithms can be implemented to work with the compliant motion control methods to reduce the telemanipulation burden of high degree-of-freedom (DoF) surgical slave devices.

Continuum robots with compliant insertion functionality can be used, among other things, to perform a minimally invasive surgery (MIS) of the throat which typically requires full anesthesia and use of a laryngoscope. Additional examples of potential applications include frontal sinus exploration surgery and office-based sinus surgery treatment and monitoring of disease progression. This technology is can also be used, for example, for micro-surgical function restoration of paralyzed vocal cords, which requires control of the location and amount of material to inject inside the paralyzed vocal cord. Currently, surgeons guess the amount of material and adjust accordingly during a follow-up surgery (assuming they do not overfill the vocal cord). By avoiding the use of full anesthesia, cost of operation is reduced and surgeons can get feedback about surgical outcomes during the procedure. Relevance is also found in injection site targeting that currently pairs a trans-dermal injection with a microscope for visualizing the anatomy.

In one embodiment, the invention provides a method of controlling movement of a continuum robot that includes a plurality of independently controlled segments along the length of the continuum robot. The continuum robot is inserted into a cavity of unknown dimensions or shape. A plurality of forces acting upon the continuum robot by the surrounding cavity are estimated. A positioning command indicating a desired movement of the distal end of the continuum robot is received from a manipulator control. The desired movement is augmented based, at least in part, on the estimated plurality of forces acting on the continuum robot such that movement is restricted to within safe boundaries of the surrounding cavity. The positioning of the continuum robot is then adjusted based on the augmented desired movement.

In some such embodiments, the desired movement includes an advancement of the continuum robot through a nasal cavity towards a surgical site in the throat of a patient. The desired movement is augmented by determining an appropriate safe pose for the continuum robot as the distal end is advanced further into the cavity.

In another embodiment, the invention provides a method of controlling positioning of a continuum robot. A set of allowable motions and a set of allowable forces are determines for a continuum robot based, in some cases, on the current position and surroundings of the continuum robot. The set of allowable motions and the set of allowable forces are then projected as projection matrices into a joint space corresponding to a manipulator control. Motion commands received through the manipulator control are translated into one or more task-specific wrenches and then into a joint-torque vector command. The position of the continuum robot is adjusted based on the joint-torque vector command using a joint-space PID controller.

Other aspects of the invention will become apparent by consideration of the detailed description and accompanying drawings.

BRIEF DESCRIPTION OF THE DRAWINGS

FIG. 13 is a table providing experimental data recording during sensitivity analysis of the compliant motion controller using the experimental system of FIG. 11.

FIG. 21 is a functional block diagram of a hybrid control system for manipulation of the continuum robot.

FIG. 22A is a perspective view of a posed continuum robot.

FIG. 22B is a perspective view of a posed manipulator control corresponding to the posed position of the continuum robot in FIG. 21A.

FIG. 22C is a view of the distal end of the continuum robot as seen from the fiberscope.

FIG. 27 is a table of kinematic and static parameters of the continuum robot of FIG. 26A.

FIG. 32 is a table of experimental results of force regulation in the x direction for three bend angles and three force magnitudes.

FIG. 33 is a table of experimental results of force regulation in the y direction for three bend angles.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
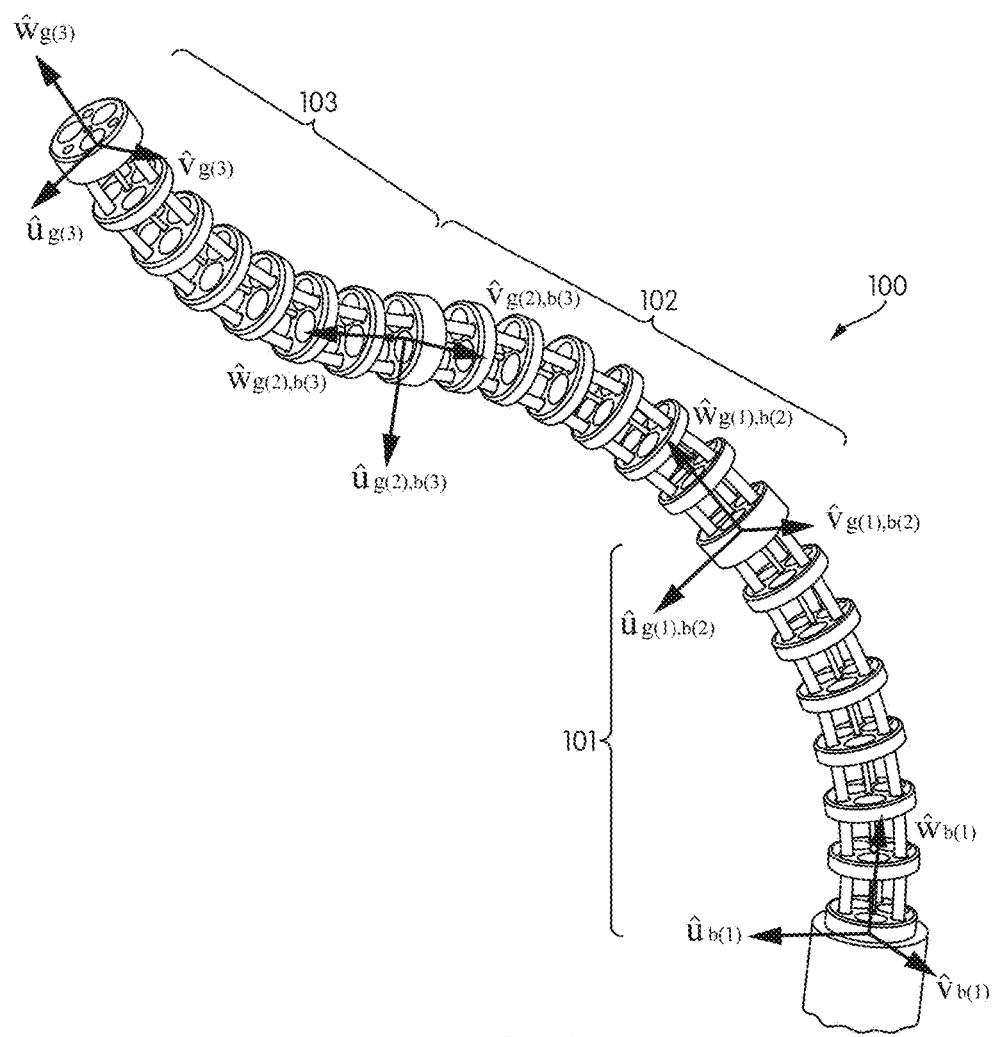
FIG. 1 is a perspective view of a multiple-segment continuum robot.

FIG. 1 illustrates a multiple-segment continuum robot 100 with multiple back-bone structures to control the movement and position of the continuum robot 100. The multiple-segment continuum robot 100 of FIG. 1 includes three independent segments 101, 102, and 103. However, other continuum robots may include more or fewer segments. In operation, a tool or other device would be extended through the continuum robot and would emerge at the distal end of the continuum robot (e.g., the open end of segment 103). The other labels and vectors illustrated in FIG. 1 are referred to below in describing the kinematics of the continuum robot.

Figure 2:
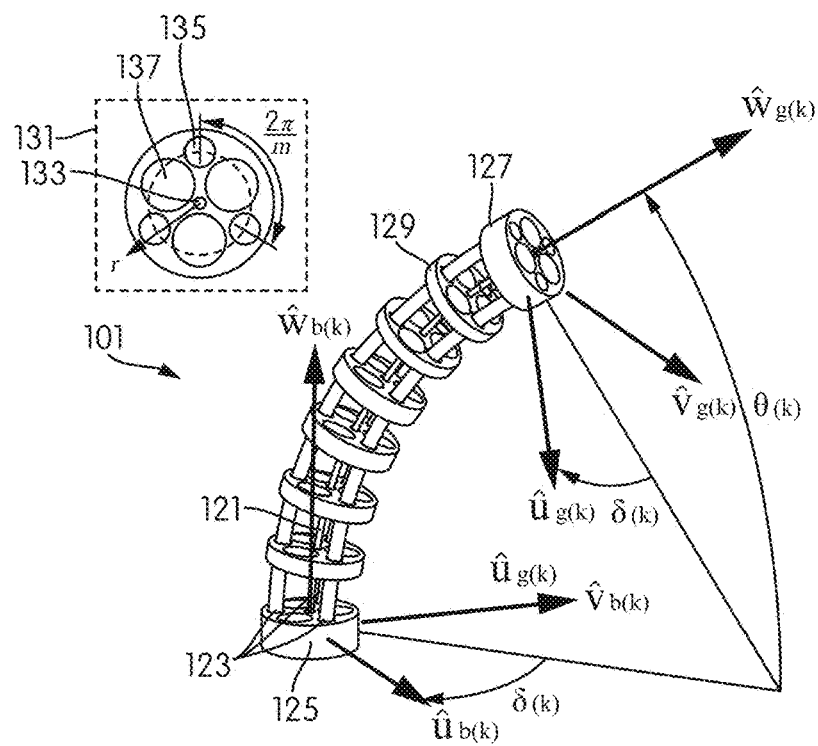
FIG. 2 is a perspective view of a single segment of the continuum robot of FIG. 1.

FIG. 2 provides a more detailed view of a single segment 101 of the continuum robot 100. The continuum robot 100 includes a single central back-bone 121 and multiple secondary back-bones 123. Each segment 101 includes a base disc 125 at the proximate end of the segment and an end disc 127 at the distal end of the segment. A plurality of spacer discs 129 are positioned between the base disc 125 and the end disc 127. The secondary back-bones 123 are super elastic NiTi tubes circumferentially distributed around the central back-bone 121. The end disc 127 is attached to all of the back-bones 121, 123. The base disc 125 is connected only to the central backbone 121. The spacer discs 129 area separated by elastomeric spacers (not pictured) and float along the central backbone 121 while maintaining a fixed radial distance between the central backbone 121 and all secondary backbones 123. Using this arrangement, two degrees of freedom (DoF) per segment are controlled by pushing and pulling on the secondary backbones 123 to bend the segment in a circular arc.

The inset 131 of FIG. 2 illustrates a top view of the discs 125, 127, and 129. A single hole 133 is positioned at the center of each disc. The central backbone 121 extends through the hole 133. Each disc in this example also includes a plurality of holes 135 positioned around the circumference of the disc. The secondary backbones 123 extend through these holes 135. Each disc also includes one or more larger holes 137. Instruments such as, for example, grabbers, cameras, light sources, laser ablation tools, imaging probes (e.g. ultrasound or optical coherence tomography) can be extended through the continuum robot via these larger holes 137 and will emerge from the distal end of the continuum robot 100. As in FIG. 1, the additional labels and vectors illustrated in FIG. 2 are referred to below in describing the kinematics of the continuum robot.

Figure 3:
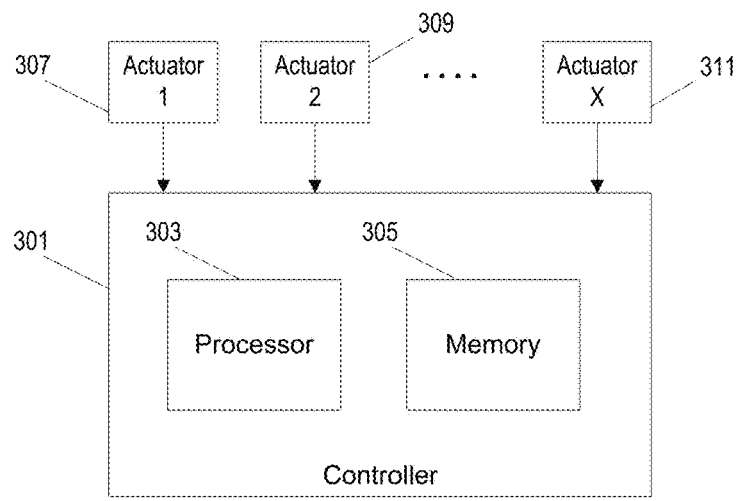
FIG. 3 is a block diagram of a controller for positioning the continuum robot of FIG. 1.

FIG. 3 illustrates a control system for the continuum robot 101 of FIG. 1. The control system includes a controller 301 with a processor 303 and a memory 305. The memory 305 stores instructions that can be executed by the processor 303 to cause the controller to control the operation of the continuum robot. Multiple actuators 307, 309, 311 are connected to and operated by the controller 301. As described above, the actuators 307, 309, 311 each push and pull on one of the secondary backbones 123 of the continuum robot 100 to adjust the position and pose of the continuum robot 100.

Figure 4:
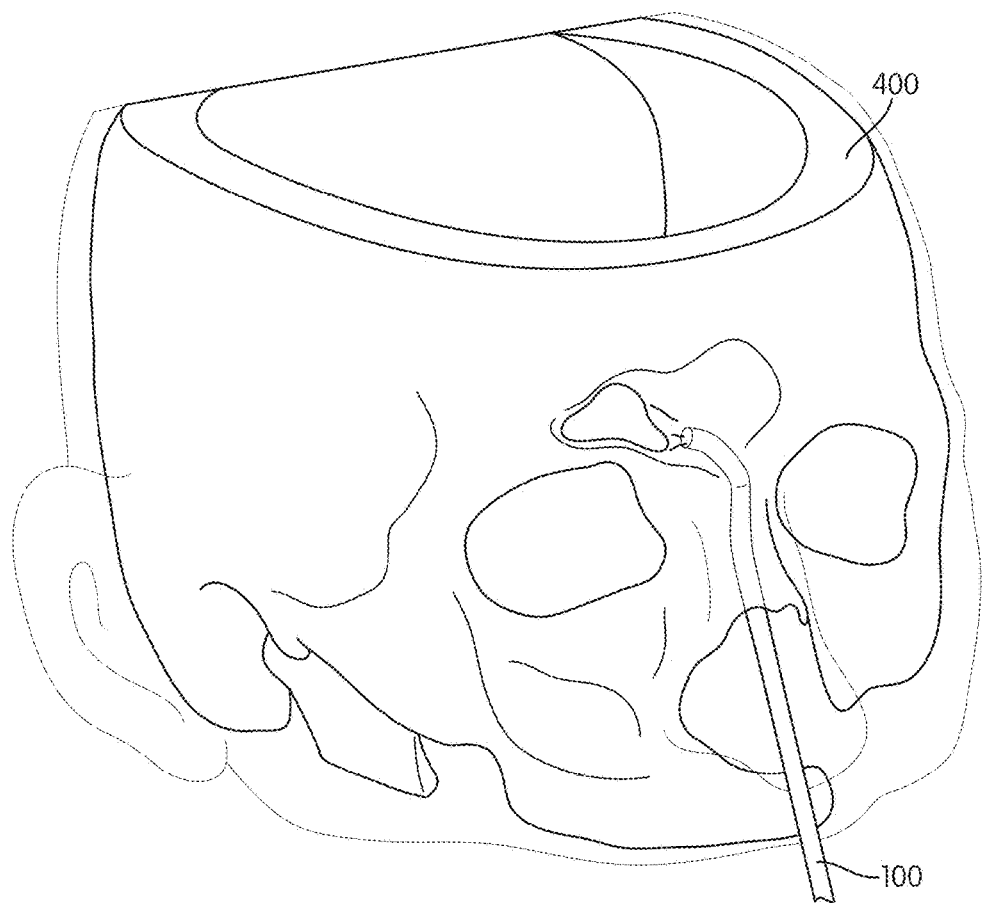
FIG. 4 is a perspective view of the continuum robot of FIG. 1 being inserted into the nasal passage of a human head.

A continuum robot 100 can be inserted into various cavities to reach a target location. Once the distal end of the continuum robot 100 is positioned at the target location, tools emerging from the distal end of the continuum robot 100 are used to perform operations. FIG. 4 illustrates an example of a continuum robot 100 inserted into the nasal passage of a human head 400. In this example, the target location for the distal end of the continuum robot is the upper sinuses. However, the exact dimensions and size of the nasal passages extending from the nose to the upper sinus may not be known. The compliant insertion methods described herein enable the continuum robot 100 to adapt its shape and position to comply with the shape of the nasal passages as the continuum robot 100 is advanced into the nasal passage. Although the examples described herein refer to a continuum robot being inserted into the nasal passage to reach an upper sinus, the methods and systems described herein also provide compliant motion control for other continuum robot applications such as minimally invasive surgery at other locations of the human body or larger applications such as search and rescue at disaster sites.

Figure 5:
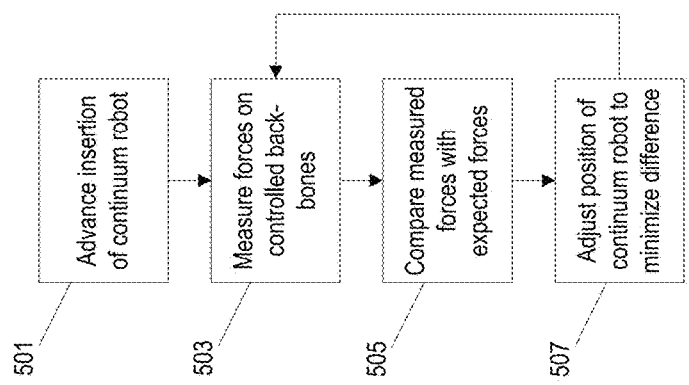
FIG. 5 is a flowchart illustrating a method of adjusting the position of the continuum robot of FIG. 1 as the continuum robot is inserted into a cavity of unknown size and dimensions.

FIG. 5 describes a method of adjusting the position and shape of the continuum robot to adapt to the shape of the cavity in which it has been inserted. The continuum robot 100 is pushed further into the cavity to advance the position of the distal end (step 501). The forces exerted along the length of the continuum robot 100 are measured (step 503). In particular, each determined force indicates the generalized forces applied to the end disc 127 of each segment of the continuum robot. These measured forces include both the forces required to position the continuum robot in its current shape and external forces, or wrenches, applied to the continuum robot 100 by the surfaces of the cavity. The measured generalized forces along the length of the continuum robot are compared to expected generalized forces that would be detected on the continuum robot if it were positioned in its current shape without the presence of external wrenches (step 505). The positions of the continuum robot segments are then adjusted to minimize the difference between the measured generalized forces and the expected generalized forces (step 507). In other words, the shape of the continuum robot is adjusted to minimize the affect of external wrenches on the continuum robot structure along the length of the continuum robot 100.

Figure 6:
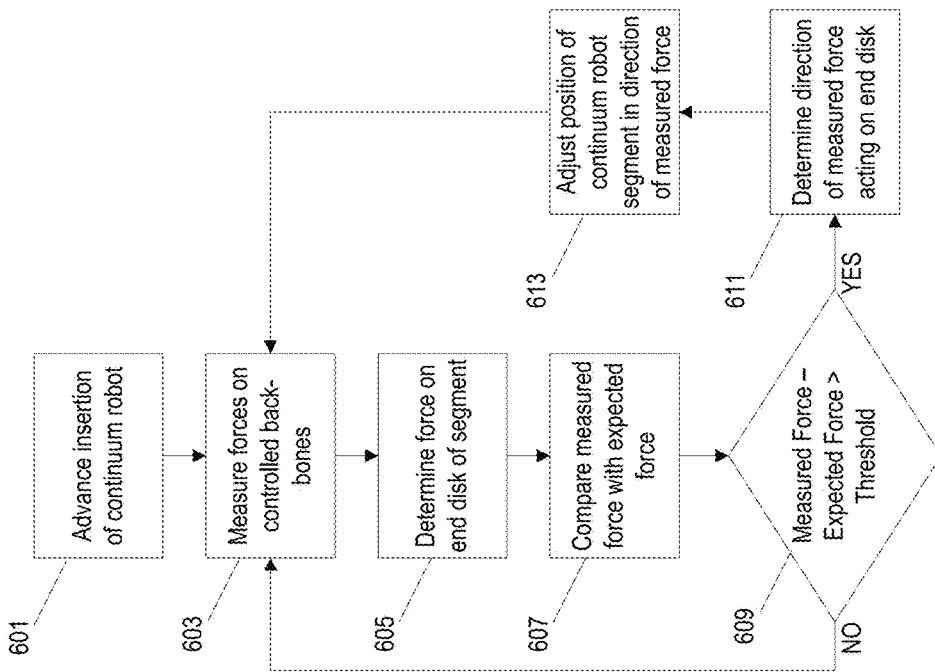
FIG. 6 is a flowchart illustrating a method of adjusting the position of a single segment of the multiple-segment continuum robot of FIG. 1 as the continuum robot is inserted into a cavity of unknown size and dimension.

FIG. 6 illustrates in further detail how the controller 301 adjusts a single segment of the continuum robot 100. The method illustrated in FIG. 6 is performed concurrently and repeatedly for each segment of the continuum robot 100 as it is inserted into the cavity. As the continuum robot 100 is advanced into the cavity (step 601), the controller measures the forces on each of the controlled secondary backbone structures 123 (step 603). The forces are measured at the actuator units and, again represent the forces required to position the continuum robot in its current position and external wrench applied to the continuum robot structure by the surfaces of the cavity. The controller further determines a generalized force applied to the end disc of each individual segment of the continuum robot (step 605). The determined generalized force is compared with an expected generalized force (step 607) to determine the magnitude and direction of the external wrench applied to the continuum robot at the end disc of each segment. If the difference between the measured generalized force and the expected generalized force (e.g., the magnitude of the wrench) is greater than a threshold, the controller determines the direction of the wrench (step 611) and adjusts the position of the segment accordingly (step 613). If the magnitude of the wrench does not exceed the threshold, the controller continues to monitor forces (step 603) without changing the position of the continuum robot. In some embodiments, the threshold applied in step 609 is adjusted in real-time during insertion of the continuum robot into the cavity to account for elastic cavity surfaces such as internal body tissues.

Once the continuum robot has been sufficiently inserted into the cavity and the distal end of the continuum robot has reached its target location, the same compliant insertion techniques can be used to brace the continuum robot against the surfaces of the cavity. Bracing the continuum robot provides additional stability and allows for more accurate placement and maneuvering of the tools emerging from the distal end of the continuum robot. To brace the continuum robot, the controller 301 adjusts the position of each segment of the continuum robot to increase the difference between the measured generalized force and the expected generalized force on each end disc 127. To prevent damage to the continuum robot structure, the controller 301 ensures that the difference between the expected generalized force and the measured generalized force (i.e., the magnitude of the wrench) does not exceed a defined threshold.

The following nomenclature is used to describe the kinematics of the continuum robot, the mathematical modeling, and the specific techniques used to map external wrenches to a generalize force to provide for compliant insertion:

$A_i$ $i^{th}$ row of A
$A^{[i]}$ $i^{th}$ column of A
$[A]_{ij}$ Entry at the ith row and jth column of the matrix A
n Number of segments of the continuum robot
m Number of secondary backbones in each continuum segment
$c_\alpha$, $s_\alpha$ Abbreviated form of the cosine and sine respectively where $c_\alpha = \cos \alpha$ and $s_\alpha = \sin \alpha$
$\theta_{(k)}$ Bending angle for an individual segment $\delta_{(k)}$ Bending plane angle for an individual segment $\psi_{(k)}$ Configuration space vector for an individual segment, $\psi_{(k)} = [\theta_{(k)}, \delta_{(k)}]^T$ $\psi_a$ Augmented configuration space vector for the multi-segment continuum robot, $\psi_a = [\psi^T_{(1)}, \ldots, \psi^T_{(n)}]^T$ $\hat{u}, \hat{v}, \hat{w}$ Unit basis vectors of an arbitrary coordinate frame such that $[\hat{u}, \hat{v}, \hat{w}] = I \in \mathbb{R}^{3\times 3}$ $\{b_{(k)}\}$ Base frame of the kth segment $\{g_{(k)}\}$ End frame of the kth segment $^cP_{ab}$ Position vector pointing from point a (or the origin of frame {a}) to point b (or the origin of frame {b}) expressed in frame {c}

$^aR_b$ Rotation matrix describing the orientation of frame {b} with respect to frame {a}

$^cv_{b/a}$ Linear velocity of frame {b} with respect to frame {a}, expressed in frame {c}

$^c\omega_{b/a}$ Angular velocity of frame {b} with respect to frame {a}, expressed in frame {c}

$^ct_{b/a}$ Twist of frame {b} with respect to frame {a}, expressed in frame {c}: $^ct_{b/a} = [^cv^T_{b/a}, {}^c\omega^T_{b/a}]^T$ $J_{q\psi(k)}$ A Jacobian matrix linearly mapping the configuration space velocities to joint velocities such $\dot{q}_{(k)} = J_{q\psi(k)} \dot{\psi}_{(k)}$ $J_{v\psi(k)}$ A Jacobian matrix linearly mapping the configuration space velocities to linear velocities such that $v = J_{v\psi(k)} \dot{\psi}_{(k)}$ $J_{\omega\psi(k)}$ A matrix linearly mapping of the configuration space velocities to angular velocities such that $\omega = J_{\omega\psi(k)} \dot{\psi}_{(k)}$ $J_{t\psi(k)}$ A linear mapping of the configuration space velocities to the twist such that $t = J_{t\psi(k)} \dot{\psi}_{(k)}$ and $$J_{t\psi(k)} = \begin{bmatrix} J_{v\psi(k)} \\ J_{w\psi(k)} \end{bmatrix}$$

$E_Y$ Young's elasticity modulus for the NiTi back-bones $I_{(k)}$ Cross-sectional second moment of inertia of back-bones of the kth segment r Radius of the pitch circle along which the secondary backbones are circumferentially distributed around the primary backbone $\tau_{(k)}$ Backbone actuation forces of an individual segment $\tau_{(k)} = [\tau_{1,(k)}, \ldots, \tau_{m,(k)}]^T$ $f_{(k)}$ Generalized force for the kth individual segment $f_a$ Augmented generalized force for the multi-segment continuum robot $f_a = [f^T_{(1)}, \ldots, f^T_{(n)}]^T$ $\lambda, \hat{\lambda}$ Actual and estimated augmented generalized force errors $K_{\psi,(k)}$ Configuration space stiffness for the kth individual segment $K_{\psi a}$ Configuration space stiffness for the multi-segment continuum robot x Input feature vector to the Support Vector Regression (SVR)

N The number of training data for the SVR optimization $\varphi(\cdot)$ High dimensional mapping of the input feature space of the support vectors in the SVR The pose of the $k^{th}$ segment continuum robot (as illustrated in FIG. 2) is described in a set of generalized coordinates by a configuration space vector defined as $$\psi_{(k)} = [\theta_{(k)}, \delta_{(k)}]^T \quad (1)$$

where $(\cdot)_{(k)}$ denotes a variable associated with the $k^{th}$ segment. $\theta_{(k)}$ defines the bending angle of the segment measured from the plane defined by the base disk, $\{\hat{u}_{b(k)}, \hat{v}_{b(k)}\}$, and the direction normal to the end disk $\hat{w}_{g(k)}$. $\delta_{(k)}$ defines the orientation of the bending plane of the segment as measured from the plane to the $\hat{u}_{b(k)}$ about $\hat{w}_{b(k)}$.

The inverse kinematics of the segment relating the configuration space, $\psi_{(k)}$, to the joint space, $q_{(k)} = [q_{1,(k)}, q_{2,(k)}, \ldots, q_{m,(k)}]^T$, is given by $$L_{j,(k)} = L_{(k)} + q_{j,(k)} = L_{(k)} \Delta_{j,(k)} \Theta_{(k)}. \quad (2)$$

where $L_{j,(k)}$ is the length of the $j^{th}$ secondary backbone of the $k^{th}$ segment for $j = 1, \ldots, m$, $L_{(k)}$ is the length of the primary backbone of the $k^{th}$ segment, $\Delta_{j,k} = r \cos \sigma_{j,k}$; $\sigma_{j,(k)} = \delta_{(k)} + (j-1)(2\pi/m)$, and $\Theta_{(k)} = \theta_{(k)} - \pi/2$.

The instantaneous inverse kinematics can be described by differentiating (2) to yield $$\dot{q}_{(k)} = J_{q\psi(k)} \dot{\psi}_{(k)} \quad (3)$$

where the Jacobian $J_{q\psi(k)}$ is given by $$J_{q\psi(k)} = \begin{bmatrix} rc_{\sigma_{1,(k)}} & -r\theta_{(k)} s_{\sigma_{1,(k)}} \\ \vdots & \vdots \\ rc_{\sigma_{m,(k)}} & -r\theta_{(k)} s_{\sigma_{m,(k)}} \end{bmatrix} \quad (4)$$

The direct kinematics of the $k^{th}$ segment is given by the position b(k)Pb(k)g(k) and orientation b(k)Rg(k) of the segment end disk with respect to its base disk. For $$\theta_{(k)} \neq \frac{\pi}{2},$$

the kinematics takes the form $$^{b(k)}P_{b(k)g(k)} = \frac{L_{(k)}}{\theta_{(k)}} \begin{bmatrix} c_{\sigma(k)}(s_{\theta(k)} - 1) \\ -s_{\sigma(k)}(s_{\theta(k)} - 1) \\ -c_{\theta(k)} \end{bmatrix} \quad (5)$$

$$^{b(k)}R_{g(k)} = e^{-\sigma(k)[\hat{w}x]} e^{-\theta(k)[\hat{v}x]} e^{\sigma(k)[\hat{w}x]} \quad (6)$$

where $\hat{v} = [0, 1, 0]^T$, $\hat{w} = [0, 0, 1]^T$ and the frames $\{g(k)\}$ and $\{b_{(k)}\}$ are shown in FIG. 3. For $$\theta_{(k)} = \frac{\pi}{2},$$

the formulation singularity, $$\frac{1}{\theta_{(k)}},$$

resolves to $$^{b(k)}Pb_{(k)}g_{(k)} = [0\ 0\ L_{(k)}]^T \quad (7)$$

$$^{b(k)}Rg_{(k)} = I \in \mathbb{R}^{3\times 3} \quad (8)$$

By differentiating (5) and (6), the instantaneous direct kinematics takes the form $$^{b(k)}t_{g(k)/b(k)} = J_{t\psi(k)} \dot{\psi}_{(k)} \quad (9)$$

where, for $$\theta_{(k)} = \frac{\pi}{2},$$

the Jacobian $J_{t\psi_{(k)}}$ is given by δ

$$J_{t\psi_{(k)}} = \begin{bmatrix} Lc_{\delta_{(k)}} \frac{\theta_{(k)}c_{\theta_{(k)}} - s_{\theta_{(k)}} + 1}{\theta_{(k)}^2} & -Ls_{\delta_{(k)}} \frac{s_{\theta_{(k)}}}{\theta_{(k)}} - 1 \\ Ls_{\delta_{(k)}} \frac{\theta_{(k)}c_{\theta_{(k)}} - s_{\theta_{(k)}} + 1}{\theta_{(k)}^2} & Lc_{\delta_{(k)}} \frac{s_{\theta_{(k)}} - 1}{\theta_{(k)}} \\ L \frac{s_{\theta_{(k)}} + c_{\theta_{(k)}}}{\theta_{(k)}^2} & 0 \\ -s_{\delta_{(k)}} & c_{\delta_{(k)}} c_{\theta_{(k)}} \\ -c_{\delta_{(k)}} & -s_{\delta_{(k)}} c_{\theta_{(k)}} \\ 0 & -1 + -s_{\theta_{(k)}} \end{bmatrix} \quad (10)$$

and for $$\theta_{(k)} = \frac{\pi}{2},$$

the formulation singularity, $$\frac{1}{\theta_{(k)}},$$

is resolved by applying l'Hôpital's rule, to yield $$J_{t\psi_{(k)}} = \begin{bmatrix} -\frac{L}{2}c_{\delta_{(k)}} & \frac{L}{2}s_{\delta_{(k)}} & 0 & -s_{\delta_{(k)}} & -c_{\delta_{(k)}} & 0 \\ 0 & 0 & 0 & 0 & 0 & 0 \end{bmatrix}^T \quad (11)$$

Using Euler beam bending analysis and neglecting gravitational potential energy, the total energy of the continuum robot is given by $$U = \sum_{k=1}^{n} U_{(k)}$$

where the potential elastic energy of the $k^{th}$ segment is given by $$U_{(k)} = \frac{E_Y I_{(k)} \theta_{(k)}^2}{2} \left( \frac{1}{L_{(k)}} + \sum_{j=1}^{m} \frac{1}{l_{j,(k)}} \right) \quad (12)$$

The principle of virtual work and the energy expression (12) are used to obtain a statics model for the $k^{th}$ continuum segment as $$J_{q\psi_{(k)}}^T \tau_{(k)} = \nabla U_{(k)} - J_{x\psi_{(k)}}^T w_{e,(k)} \quad (13)$$

where $\tau_{(k)}$ represents the actuation forces on the secondary backbones, $\nabla U_{(k)}$ is the gradient of the potential energy, and $w_{e,(k)}$ is the external wrench applied to the end disk of the $k^{th}$ continuum segment. The energy gradient $\nabla U_{(k)}$ is calculated with respect to a virtual displacement in configuration space. $\Delta \psi_{(k)} = [\Delta \theta_{(k)}, \Delta \delta_{(k)}]^T$ and is given by $$\nabla U_{(k)} = E_Y I_{(k)} \begin{bmatrix} \frac{\theta_{(k)}}{L_{(k)}} + \sum_{j=1}^{m} \frac{\theta_{(k)}}{L_{j,(k)}} - \frac{\theta_{(k)}^2}{2} r & \sum_{j=1}^{m} \frac{c_{\sigma_{j,(k)}}}{L_{j,(k)}^2} \\ \frac{\theta_{(k)}^3}{2} r \sum_{j=1}^{m} \frac{s_{\sigma_{j,(k)}}}{L_{j,(k)}^2} \end{bmatrix} \quad (14)$$

The statics expression (13) projects both the actuation forces $T_{(k)}$ and perturbation wrench $w_e,(k)$ w into the configuration space of the continuum segment, $\psi_{(k)}$. Thus, after projecting the wrench from three-dimensional Cartesian space, $\mathbb{R}^6$, into the configuration space, $\mathbb{R}^2$, the projected generalized force on the segment resides in the vector space controllable within the framework of the single-segment kinematics of equation (1). This projection eliminates the requirements for explicit determination of wrenches required by conventional compliance algorithms and casts the interaction force minimization problem into the configuration space of the continuum segment.

If the wrench acting on the end disk that is projected into the configuration space of the $k^{th}$ segment is defined as the generalized force vector $$f_{(k)} = J_{t,\psi_{(k)}}^T w_{e(k)} \quad (15)$$

Applying equation (13) to the generalized force expression, the $i^{th}$ row of the generalized force $f_{(k)}$ can be written as $$f_i = \nabla U_i - [J_{q\psi}^T]_i T = \nabla U_i [J_{q\psi}^{[i]}]^T T \quad (16)$$

where $J_{q\psi}^{[i]}$ denotes the $i^{th}$ column of $J_{q\psi}$.

For small perturbations from an equilibrium configuration, the stiffness of the individual continuum segment can be posed in the configuration space as $$\delta f = K_\psi \delta \psi \quad (17)$$

where the stiffness is given by the Jacobian of the generalized force with respect to configuration space perturbation. Thus, the elements of $k_\psi$ are given by:

$$\frac{\partial f_i}{\partial \psi_j} = [K_\psi]_{ij} = \frac{\partial}{\partial \psi_j} \left[ \nabla U_i - [J_{q\psi}^{[i]}]^T T \right] \quad (18)$$

The elements of the stiffness matrix (18) can be expanded as $$[K_\psi]_{ij} = [H_\psi]_{ij} - \left[ \frac{\partial}{\partial \psi_j} (j_{q\psi}^{[i]}) \right]^T T - [J_{q\psi}^{[i]}]^T \frac{\partial T}{\partial \psi_j} \quad (19)$$

The first term of the configuration space stiffness, $H_\psi$, is the Hessian of the elastic energy of the segment given by $$H_\psi = \begin{bmatrix} \frac{\partial^2 U}{\partial \theta^2} & \frac{\partial^2 U}{\partial \theta \partial \beta} \\ \frac{\partial^2 U}{\partial \delta \partial \theta} & \frac{\partial^2 U}{\partial \delta^2} \end{bmatrix} \quad (20)$$

The individual elements of the Hessian, $H_\psi$, are given by $$\frac{\partial^2 U}{\partial \theta^2} = E_Y I \left[ \frac{1}{L} + \sum_{i=1}^{m} \frac{1}{L_i} - 2r\theta \sum_{i=1}^{m} \frac{c_{\sigma_i}}{L_i^2} + \theta^2 r^2 \sum_{i=1}^{m} \frac{c_{\sigma_i}^2}{L_i^3} \right] \quad (21)$$

$$\frac{\partial^2 U}{\partial \theta \partial \delta} = \frac{\partial^2 U}{\partial \delta \partial \theta} = E_Y I \left[ \frac{3\theta^2}{2} r \sum_{i=1}^{m} \frac{s_{\sigma_i}}{L_i^2} - \theta^3 r^2 \sum_{i=1}^{m} \frac{s_{\sigma_i} c_{\sigma_i}}{L_i^3} \right] \quad (22)$$

$$\frac{\partial^2 U}{\partial \delta^2} = E_Y I \left[ \frac{\theta^3}{2} r \sum_{i=1}^{m} \frac{c_{\sigma_i}}{L_i^2} + \theta^4 r^2 \sum_{i=1}^{m} \frac{s_{\sigma_i}^2}{L_i^3} \right] \quad (23)$$

The second term of equation (19) expands to $$\frac{\partial}{\partial \psi_1}(J_{q\psi}^1) = 0 \in \mathbb{R}^m \quad (24)$$

$$\frac{\partial}{\partial \psi_1}(J_{q\psi}^2) = \frac{\partial}{\partial \psi_2}(J_{q\psi}^1) = -r[s_{\sigma_1}, \ldots, s_{\sigma_m}]^T \quad (25)$$

$$\frac{\partial}{\partial \psi_2}(J_{q\psi}^2) = -r\theta[c_{\sigma_1}, \ldots, c_{\sigma_m}]^T \quad (26)$$

Figure 7:
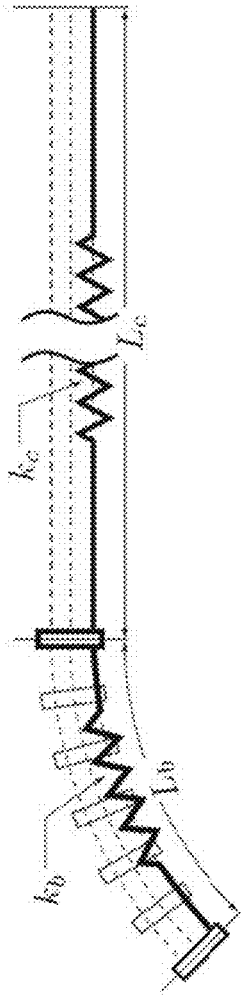
FIG. 7 is a stiffness model for segment of the continuum robot of FIG. 1 with multiple back-bone structures.

Finally, the third term of equation (19) can be expanded by applying a simplifying assumption based on the relative geometry of the backbones in remote actuated continuum system configurations. The stiffness of the continuum robot, as measured from the actuation forces at the proximal end of the actuation lines, is a function of strain throughout the length of the actuation lines. As illustrated in FIG. 7, the contributions to the axial stiffness are divided into the stiffnesses, $k_b$ and $k_c$, corresponding to the bending, $L_b$, and non-bending, $L_c$, regions of the actuation lines connecting the working distal end to the actuation unit.

The axial stiffness along the length of a given actuation line can then be expressed as $$\frac{1}{k} = \frac{1}{k_c} + \frac{1}{k_b} \quad (27)$$

where $$k_c = \frac{E_Y A}{L_c} \text{ and } k_b = \frac{E_Y A}{L_b}$$

and A denotes the cross-sectional area of the backbone.

For continuum robotic systems with remote actuation that are designed to access deep confined spaces, the lengths of the non-bending regions of the actuation lines far exceed that of the bending regions, $L_c \gg L_b$. The stiffness will therefore be dominated by the non-bending regions of the actuation lines. Local perturbations of the backbones at the actuation unit can be expressed as $$\frac{\partial T}{\partial q} = K_q \quad (28)$$

Where $$K_q \cong \begin{bmatrix} \frac{E_Y A}{L_c} & 0 & 0 \\ 0 & \ddots & 0 \\ 0 & 0 & \frac{E_Y A}{L_c} \end{bmatrix} \in \mathbb{R}^{m \times m} \quad (29)$$

Expanding terms by applying the chain rule and using the instantaneous inverse kinematics of equation (3), $$\frac{\partial T}{\partial \psi}$$

is given by $$\frac{\partial T}{\partial \psi} = \frac{\partial T}{\partial q} \frac{\partial q}{\partial \psi} \cong K_q J_{q\psi} \quad (30)$$

The configuration space stiffness therefore reduces to $$[K_\psi]_{ij} = [H_\psi]_{ij} - \left[ \frac{\partial}{\partial \psi_j}(J_{q\psi}^{[i]}) \right]^T T - [J_{q\psi}^{[i]}]^T K_q J_{q\psi}^{[j]} \quad (31)$$

Using the generalized force and stiffness as defined in equations (15) and (31), a compliant motion controller can be constructed to minimize the difference between the expected and measured actuation forces in the secondary backbones. The controller provides compliant motion control of each continuum segment subject to a perturbing wrench at the end disk of the segment. This wrench approximates a multitude of small perturbation forces acting along the length of a continuum segment during an insertion through a tortuous path (e.g., a cavity of unknown size, shape, and dimensions). In an analogy to a linear spring model with an equilibrium position, $f=k(x_{eq}-x)$, there exists an equilibrium pose $\{^{b(k)}P_{eq}, ^{b(k)}R_{eq}\}$, at which the wrench is minimized in the operation space of the continuum segment. Given this equilibrium position and the projection of the applied wrench to the configuration space, there exists a unique, though unknown, configuration $\psi_{(k),d}=g(^{b(k)}P_{eq}, ^{b(k)}R_{eq})$ that minimizes the wrench applied to the continuum segment. The objective of the compliance controller is to advance to this position using the available sensing information of the actuation forces in the backbones, $T_{(k)}$ and therefore minimize the interaction wrench.

For multi-segment continuum robots, a pose exists in the overall configuration space that minimizes the augmented generalized force on the system. The augmented generalized force vector for an n-segment continuum robot $$f_a = [f_{(1)}^T \ldots f_{(n)}^T]^T \quad (32)$$

is associated with the augmented configuration space $$\psi_a = [\psi_{(1)}^T \ldots \psi_{(n)}^T]^T \quad (33)$$

The configuration space stiffness of an individual segment is generalized as the following to result in the augmented configuration space stiffness of the multi-segment continuum robot $$K_{\psi_a} = \begin{bmatrix} K_{\psi,(1)} & 0 & \cdots & 0 \\ 0 & K_{\psi,(2)} & & \vdots \\ \vdots & & \ddots & 0 \\ 0 & \cdots & 0 & K_{\psi,(n)} \end{bmatrix} \quad (34)$$

An error function is defined as the distance in configuration space from the current configuration, $\psi_a$ to the desired configuration $\psi_{ad}$, as $$e_{\psi_a} = \psi_{a_d} - \psi_a \quad (35)$$

For a passive wrench condition, the equilibrium pose and corresponding configuration space remain fixed, e.g., $\dot\psi_{ad}=0$. For external wrenches changing slowly with respect to the compliant control update rate, this condition becomes $\dot\psi_{ad} \approx 0$ and hence negligible when taking the time derivative of $e_{\psi_a}$. The following discussion uses $\dot\psi_{ad}=0$ although it is to be understood that the same derivation follows for $\dot\psi_{ad} \approx 0$ by changing the equality sign to an approximation sign. The time derivative of the error function under these conditions becomes $$\dot e_{\psi_a} = -\dot\psi_a. \quad (36)$$

For small perturbations, the distance in configuration space is given as $\Delta\psi_a = \psi_{a_d} - \psi_a$. Thus by applying the configuration space stiffness $K_{\psi_a}$, the error in the system can be related to the generalized force as $$f_a = K_{\psi_a} e_{\psi_a}. \quad (37)$$

Where $\Delta f_a \cong f_a$ for the small perturbations. This assumption holds for robots that are calibrated such that $f_a \approx 0$ for unloaded movements throughout the workspace.

During control of a continuum system the estimated generalized force $\hat{f}_a$ is calculated using the idealized statics model of $f_a$ based on the estimate of the energy and measured actuation forced as in equation (16). This estimate is contaminated by an error $\lambda$ due to un-modeled friction and strain along the actuation lines, perturbations from circulate-bending shape of individual segments, deviations in the cross-section of the backbones during bending, and uncertainties in the elastic properties of the NiTi backbones. Thus without compensation, the generalized force estimate takes the form $$\hat{f}_{a,uncompensated} = f_a + \lambda \quad (38)$$

where $f_a$ is given by equation (16).

The generalized force error $\lambda$ is identified using the definition in equation (38) for movements of the continuum robot through its workspace with no externally applied wrenches. During this unloaded movement, the wrench at the end disk is $w_e=0$ and equation (15) predicts $f_a=0$. In an ideal continuum robot lacking backlash, friction and other un-modeled effects, the prediction of the generalized force based on the measured values of the actuation forces $T_{(k)}$ in equation (16) for each segment would also return $f_a=0$. However, the actual kinetostatic effects cause $f_a \neq 0$ and this deviation forms $\lambda$ that we seek to estimate. In order to compensate for the errors due to the interaction between segments, non-linear regression via Support Vector (SV) machines is investigated and applied.

These model errors are highly dependent on the pose of the robot and the path in the configuration space to this pose. To compensate for the error, a feed forward term is added to equation (38) to reduce the effects of $\lambda$ during compliant motion control such that the compensated generalized force estimate is given by $$\hat{f}_a = f_a + \lambda - \hat\lambda. \quad (39)$$

An augmented compliant motion controller, taking into account the estimates of the un-modeled error, $\hat\lambda$, takes the form $$\dot\psi_a = \mu A \hat{f}_a \quad (40)$$

where $\mu$ and A correspond respectively to positive definite scalar and matrix gains to be chosen by the operator.

A compliant motion controller utilizing the error compensation techniques described above, results in a system error that is uniformly bounded for any generalized force error by $$\|e_{\psi_a}\| > \|K_{\psi_a}^{-1}(\lambda-\hat\lambda)\|. \quad (41)$$

The dynamics of the error in the configuration space applying equation (40) to equation (36) and accounting for equation (39) is represented as $$\dot e_{\psi_a} = -\mu A (K_{\psi_a} e_{\psi_a} + \lambda - \hat\lambda) \quad (42)$$

A Lyapunov function candidate of the error system for compliant control, represented by equation (42), can be defined as $$v(e_{\psi_a}) = 1/2 e_{\psi_a}^T P e_{\psi_a} \quad (43)$$

where P is any symmetric positive definite matrix. Differentiating equation (43) with respect to time and accounting for equation (42) yields $$\dot V(e_{\psi_a}) = e_{\psi_a}^T P \dot e_{\psi_a} = -\mu e_{\psi_a}^T P A (K_{\psi_a} e_{\psi_a} + \lambda - \hat\lambda) \quad (44)$$

Choosing the control and Lyapunov weighting matrices as $A = K_{\psi_a}^{-1}$ and $P=I$, the derivative of the Lyapunov function reduces to $$\dot V(e_{\psi_a}) = -\mu(e_{\psi_a}^T e_{\psi_a} + e_{\psi_a}^T K_{\psi_a}^{-1}(\lambda-\hat\lambda)) \quad (45)$$

A controller implementing these techniques relies on the invertibility of the configuration space stiffness. The block diagonal matrix is constructed of the sub-matrices, $K_{\psi_{(k)}}$ as in equation (34). Singular configurations of $K_{\psi_{(k)}}$ and, therefore, $K_{\psi_a}$ correspond with a straight segment, $$\theta_{(k)} = \frac{\pi}{2}.$$

For control purposes, the effect of singular poses can be mitigated using a singularity robust inverse of the configuration space stiffness.

Noting the expression $e_{\psi_a}^T e_{\psi_a}$ is positive definite for all $e_{\psi_a}$ and $\mu>0$ it is sufficient to show $\|e_{\psi_a}^T e_{\psi_a}\| > \|e_{\psi_a}^T K_{\psi_a}^{-1}(\lambda-\hat\lambda)\|$ to prove the time derivative of the Lyapunov function candidate is negative definite.

Assuming the bound on the generalized force error, represented by equation (41), and applying the identity $\|e_{\psi_a}^T\| \|e_{\psi_a}\| = \|e_{\psi_a}^T e_{\psi_a}\|$ yields $$\|e_{\psi_a}^T e_{\psi_a}\| > \|e_{\psi_a}^T\| \|K_{\psi_a}^{-1}(\lambda-\hat\lambda)\| \quad (46)$$

Applying the Schwarz inequality $\|e_{\psi_a}^T\| \|K_{\psi_a}^{-1}(\lambda-\hat\lambda)\| \geq \|e_{\psi_a}^T K_{\psi_a}^{-1}(\lambda-\hat\lambda)\|$ to equation (46), the condition on the generalized force error assumed for stability can be expanded as $$\|e_{\psi_a}^T e_{\psi_a}\| > \|e_{\psi_a}^T K_{\psi_a}^{-1}(\lambda-\hat\lambda)\| \quad (47)$$

thus proving the stability of the controller given the bounds on the compensation error.

The techniques described above illustrate controller stability for estimation uncertainties, $\lambda - \hat\lambda$ that are small with respect to the system error, $e_{\psi_a}$. In order to maintain a stable pose in configurations where $\|k_{\psi_a} e_{\psi_a}\| \approx \|(\lambda-\hat\lambda)\|$, i.e. at configurations close to the minimum of the generalized force, the input to the controller is filtered such that estimation error does not drive accidental motion. In the example controller described in further detail below, a dead-band filter is used to ensure that the controller acts for deviation above a reasonable bound for the estimation error. The performance compromise of applying this filter is a reduction in the sensitivity of the controller.

Bounds for the sensitivity of the compliant motion controller, defined by equation (40), are limited by the error in canceling the generalized force uncertainties, $\lambda - \hat{\lambda}$. For small load perturbations to the continuum robot, the errors in the generalized force, $\lambda$, are well approximated by a function of the robot pose in configuration space $\psi_a$ and the trajectory leading to this pose, $\dot{\psi}_a$. Furthermore, the trajectory required to achieve a pose influences the friction and backlash in the system at the current pose. The performance of the controller depends on canceling deviations from the idealized model. As specified in equation (39), this cancellation is carried out by a feed-forward term, $\hat{\lambda}$ that is obtained though off-line training and online estimation of the model error via support vector regression (SVR).

SV machines provide a method for nonlinear regression through mapping of the input vectors into a higher dimensional feature space. Parameters for the estimation are learned by application of empirical risk minimization in this feature space through convex optimization. A subset of the training data forms the support vectors which define the parameters for regression. The robustness and favorable generalization properties with noisy data, coupled with a compact structure which allows real-time function estimation during motion control motivate the choice of a SV machine.

To estimate the error in the generalized force based on an initial unloaded exploration of the workspace, the "ν" SV Regression (ν-SVR) is employed along each dimension of the generalized force. The ν-SVR algorithm provides a means for controlling the sparsity of support vectors, therefore providing robustness to over-fitting while simultaneously reducing the number of control parameters required to be defined.

The training set for the ν-SVR contains input pairs $\{X_{[l]}, y_{[l]}\}_{l=1}^{N}$ based on the pose and generalized force gathered during an exploration of the continuum robot workspace in the absence of external perturbing forces. For the $i^{th}$ component of the generalized force, the input is given as $$x_{[l]} = \left[ \frac{\psi_{a,1}}{\max_N(\psi_{a,1})}, \dots, \frac{\psi_{a,2n}}{\max_N(\psi_{a,2n})}, \frac{\dot{\psi}_{a,1}}{\max_N(\dot{\psi}_{a,1})}, \dots, \frac{\dot{\psi}_{a,2n}}{\max_N(\dot{\psi}_{a,2n})} \right]^T \in R^{4n} \quad (48)$$

$$y_{[l]} = f_{a,i}|w_e = 0$$

where N is the number of training samples, $$\max_N(\psi_{a,i})$$

is the maximum recorded magnitude of the $i^{th}$ row of $\psi_a$ over the set $1 \in [1, N]$, and $\dot{\psi}_a$ is the configuration space velocity. This expression normalizes each element of the input vector $x_{[l]}$ to the range of $[-1, 1]$ for all data in the training set.

Given these training input vector pairs, ν-SVR provides a method for estimating the function $$f(x) = \langle w, \varphi(x) \rangle + b \quad (49)$$

where $\langle,\rangle$ is the inner product space, w and b are parameters to be determined by the convex optimization and $\varphi(.)$ $R^{4th} \rightarrow R^{n_{xh}}$ is a mapping of the input feature vector $x_{[l]}$ to a higher dimensional feature space.

As specified in equation (49), the SVR algorithm allows mapping of the input space to a higher dimensional vector space. Uncertainties in predicting the generalized force, including friction and non-linear bending, are modeled by exponential functions. As such, a Gaussian radial basis function (RBF) kernel $$k(x_{[l]}, x_{[m]}) = e^{-\gamma \|(x_{[l]} - x_{[m]})\|^2}. \quad (50)$$

is chosen as a suitable candidate for higher dimensional mapping.

The resulting ν-SVR model for function estimation with a new input vector, x*, is given by $$f(x) = \sum_{SV} (a_i^* - a_i) k(x_{[i]}, x^*) + b \quad (51)$$

It should be noted that only those training points $x_{[i], y[l]}$, denoted SV in equation (51), for which $|y[l] - f(x[l])| \geq \in$ form the support vectors. During the computation of new estimates, only these support vectors contribute to the final function estimation of equation (51), thus enforcing sparsity in the regression.

Figure 8:
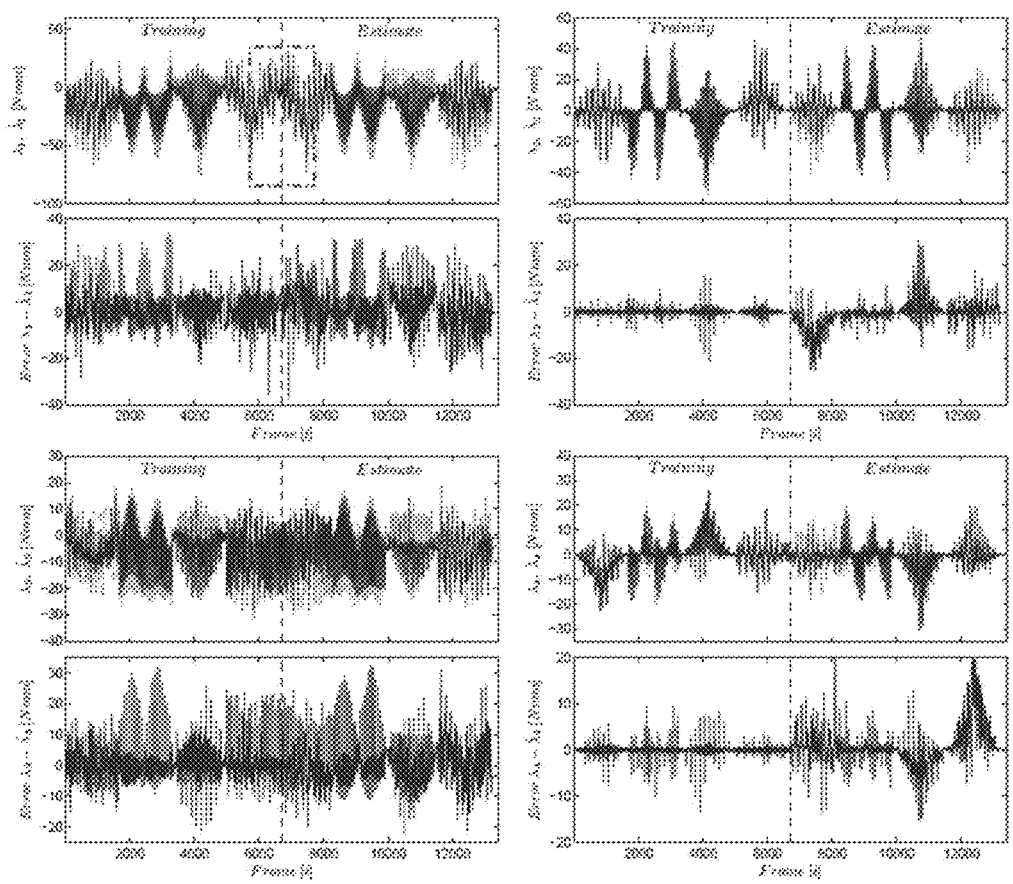
FIG. 8 is a graph of sample training and estimation data for the uncertainty parameters in a multi-segment robot.
Figure 9:
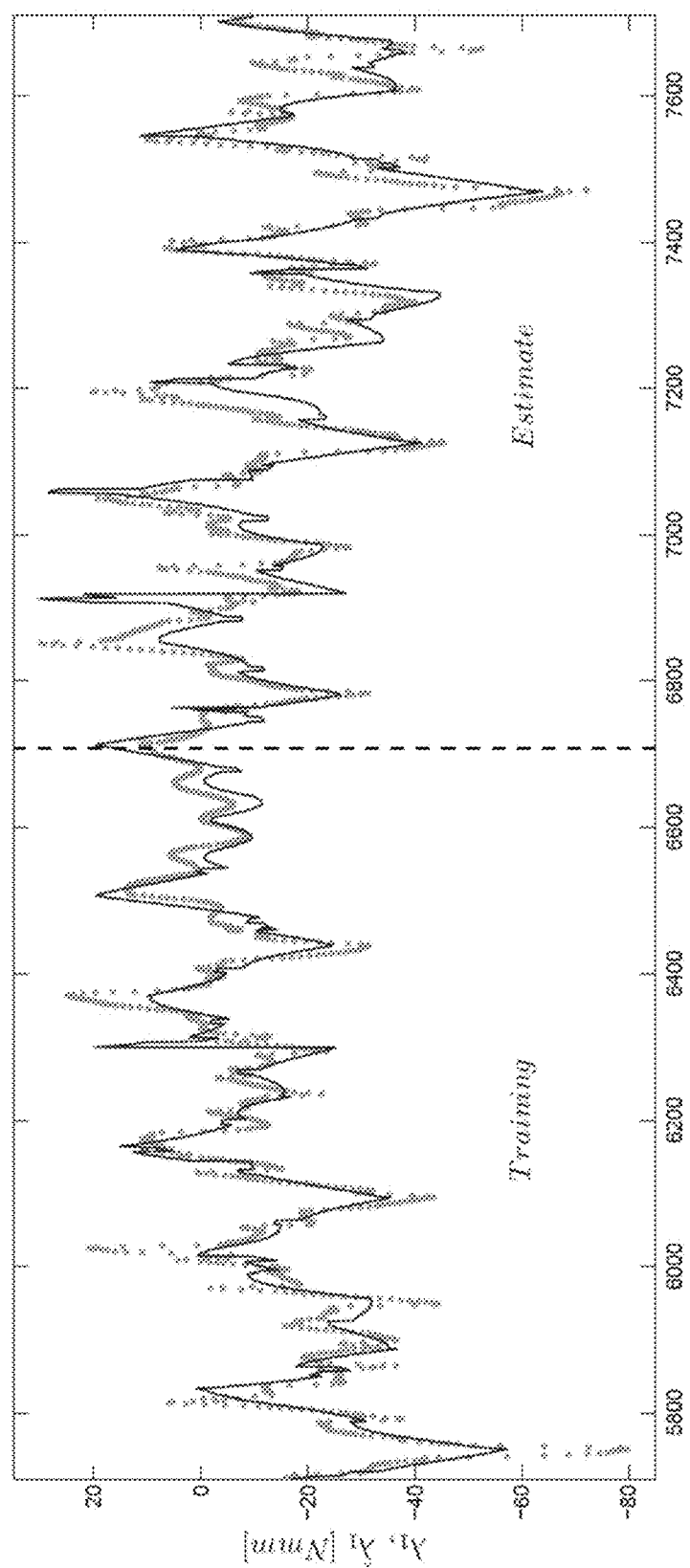
FIG. 9 is a graph of training and estimation data similar to the data provided in FIG. 8.

Software, such as LibSVM, provided by C. C. Chang and C. J. Lin at http://www.csie.ntu.edu.tw/cjlin/libswm, is employed for solving for the optimal parameters of equation (51) for each coordinate of the generalized force independently. The measured error in the generalized force $\lambda$ and the output of the regression for each component of the error compensation, equation (51), is presented for a sample data set in FIG. 8. An inset detailing $\lambda_1$ at higher resolution is provided in FIG. 9. Data for this sample set, including the robot pose, trajectory and actuation forces, was collected at 125 Hz during an unloaded motion in the configuration space of a two-segment continuum robot. The trajectories in each configuration space variable, $\theta_{(1)}, \delta_{(1)}, \theta_{(2)}, \delta_{(2)}$, are uncorrelated to provide a robust data set for estimation. Frames displayed in the FIGS. 8 and 9 are given for every tenth collected sample. The ν-SVR was trained with the first half of the data set, labeled as "Training" in the figure. The regression function was then applied without further training on the remainder of the samples, labeled "Estimate". The compensation error given by the difference between the predicted $\hat{\lambda}$ and actual $\lambda$ is presented for each direction of the generalized force.

The ν-SVR displays good generalization to the untrained data. The compensation provides a minimum of 1.4 times reduction in the RMS error for $\lambda_4$ and a maximum of 2.5 times reduction for $\lambda_1$. While the ν-SVR reduces errors on average, the compensation is locally imperfect as can be seen by maxima in the error in the $\lambda$ directions exceeding the measured errors, FIG. 8. The magnitude of the predicted ν-SVR values exceed the measured values, e.g. FIG. 9 for $\lambda_1$, producing local increases in the compensated predicted force given by $\hat{f}_a$ in equation (39). Filtering is applied to smooth outliers in the prediction values.

Figure 10:
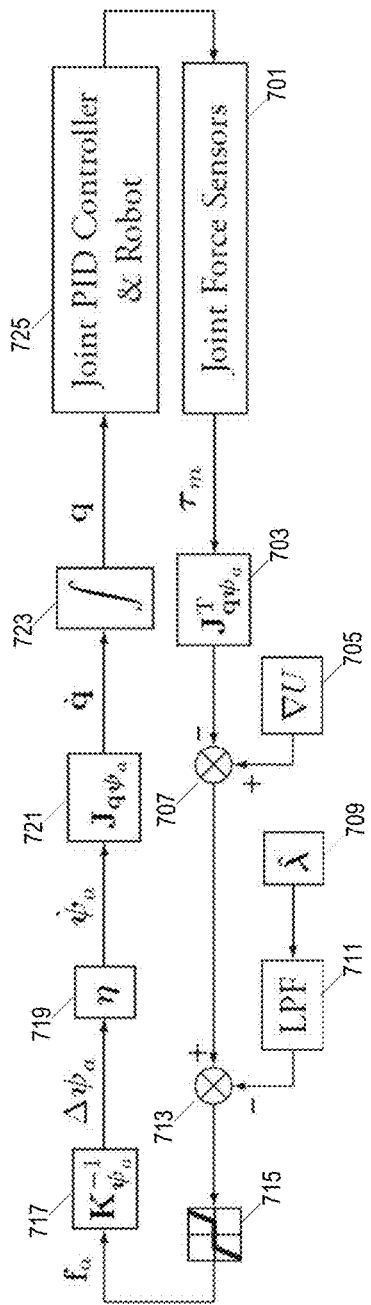
FIG. 10 is a functional block diagram of the operation of a controller providing for compliant insertion of the continuum robot of FIG. 1.

FIG. 10 illustrates an example of a real-time controller for the compliant motion algorithm. This multi-rate controller can be implemented utilizing the Matlab xPC computing environment. The main control loop updating the control values at the joint level runs at 1 kHz. Joint forces are measured at 5 kHz and smoothed with a moving average filter and down-sampled to the 1 kHz control loop. The support vector regression (SVR) is run at 100 Hz. A moving average filter smoothes outliers in the estimate provided by the support vector regression functions of equation (51).

Joint force sensors 701 provide actuation force measurements for individual segments of the continuum robot, $\tau_{(m)}$. The actuation forces are utilized to determine a Jacobian matrix linearly mapping the configuration space velocities to joint velocities (step 703). The Jacobian matrix 703 is multiplied by the energy gradient 705 at step 707. The estimated augmented generalized force errors 709 are filtered by a low pass filter 711. At step 713, the filtered force error is multiplied by the combination of the Jacobian matrix 703 and the energy gradient 705 to provide an estimated augmented force, $F_a$. In order to reduce aberrant motions of the controller due to modeling and estimation errors, a dead-band filter 715 is applied to the estimated generalized force to reduce joint motion due to uncompensated errors.

The inverse of the configuration space stiffness 717 is applied to determine difference, $\Delta_{\psi_a}$, in the configuration space between the current configuration of the continuum robot and the desired configuration. The controller then determines the configuration space vector for an equilibrium pose of the continuum robot (step 719). The Jacobian matrix mapping configuration space velocities to joint velocities is applied to the determined equilibrium pose of the continuum robot (step 721) to determine joint positions, q, for the equilibrium pose. An integral 723 is applied and the output provided to a Joint PID controller 725 that adjusts the position of the continuum robot segments to conform to the detected forces.

In the examples described above, the compliant motion controller uses a feed forward term for compensation of model uncertainties. The sum of the uncertainty estimate and the expected generalized force are filtered through a deadband to prevent motion by the controller due to errors in the compensation. Thus, generalized forces less than the threshold of the deadband filter will be neglected and the threshold for this filter therefore forms a tradeoff between the sensitivity to external perturbations and insensitivity to errors in the model and compensation.

Figure 11:
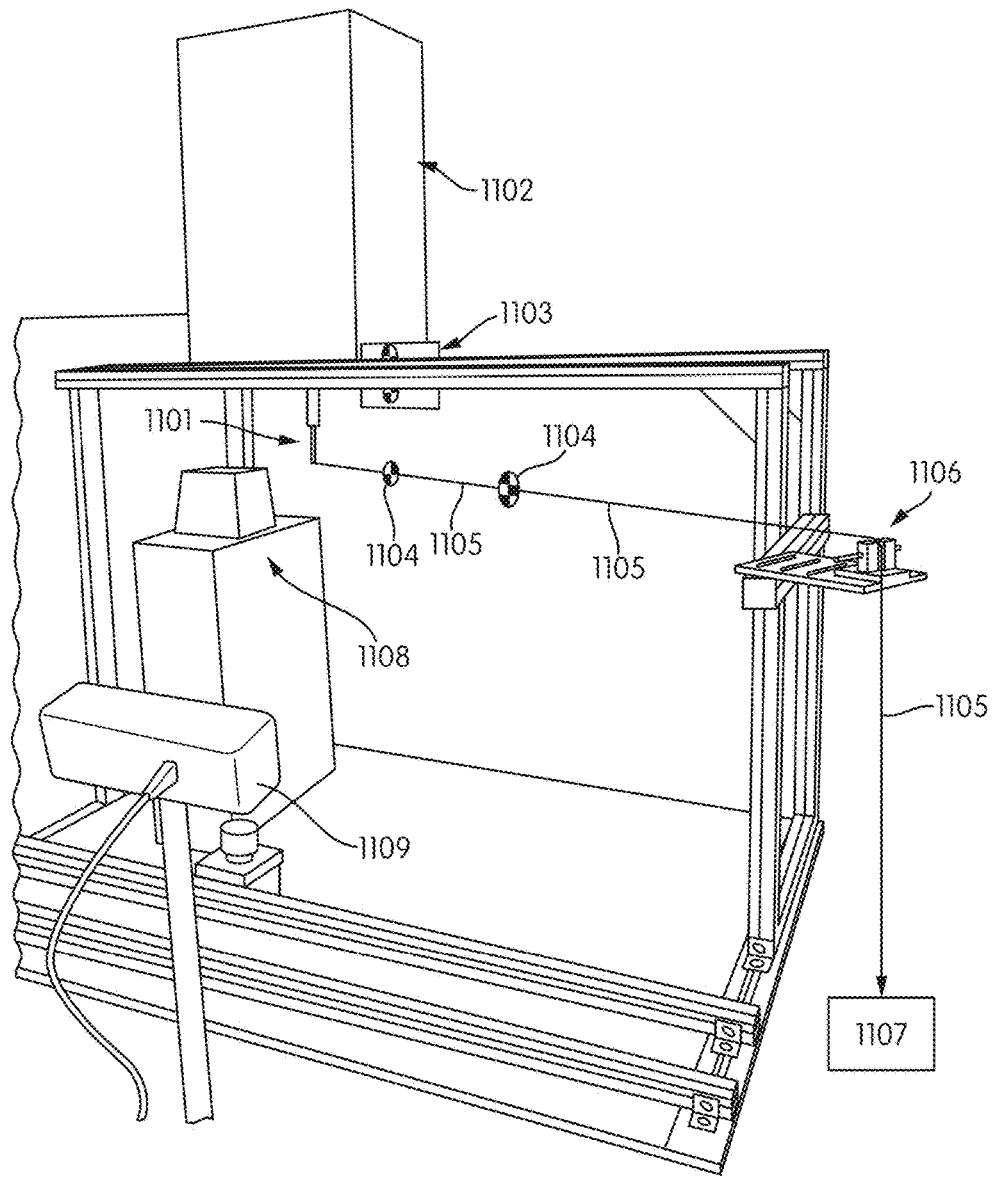
FIG. 11 is a perspective view of an experimental system for analyzing the sensitivity of a continuum robot utilizing compliant motion control.

In order to quantify the effects of the controller and thresholding, the sensitivity of the controller to external wrenches was quantified on a single-segment continuum robot. FIG. 11 illustrates an experimental system that is used to evaluated the sensitivity of the continuum robot. A wrench was applied at the end disk of the segment 1101 by a Kevlar thread 1105, attached through a pulley system 1106 to calibrated weights 1107. The load direction at each pose was quantified relative to the base of the robot by an optical tracking system 1109 with a specified accuracy of 0.20 mm RMS. Optical markers 1104 mounted to the Kevlar thread 1105 and to the base of the continuum robot 1103 serve to specify the direction of the applied force. The weight of the thread and markers is less than 1 gram and is therefore negligible with respect to the loads required to initiate the compliant motion.

The optical tracking system 1109 provides a specification for the linear accuracy of the device while the experiment requires an orientation prediction. The linear accuracy can be used to estimate the orientation accuracy of the optical tracking system 1109 by noting the orientation of a vector that is calculated based on the position of two marker points. The smallest linear distance between marker points of 48.5 mm used for the orientation estimation occurs at the base marker system 1103. Although the direction marker perpendicular to the thread is significantly shorter, this direction is not used for computing the direction vector of the Kevlar thread 1105. An RMS error of 0.2 mm at a moment of 24.25 mm corresponds to an orientation error of less than 0.5°.

For the sensitivity measurement at each pose, the segment was guided into position by manually applying an external wrench and allowing the continuum structure to comply to the sampled configuration. The pose estimate was measured via the nominal kinematics and was verified by an embedded magnetic tracker system 1108 with an RMS orientation accuracy of 0.5°. The load direction was measured via the optical trackers after a 10 gram weight was applied to the Kevlar thread to straighten the thread length between the optical markers. Calibration weights were added to the load in 1 gram increments until the threshold for motion was exceeded. The dead-band of the controller was set during the sensitivity experiments as $$\|f_1\| \leq 20 \text{ Nmm}, \|f_2\| \leq 10 \text{ Nmm}. \tag{52}$$

These thresholds were determined empirically based on the error compensation in the generalized force and the stability of the controller.

Figures 12, 15:
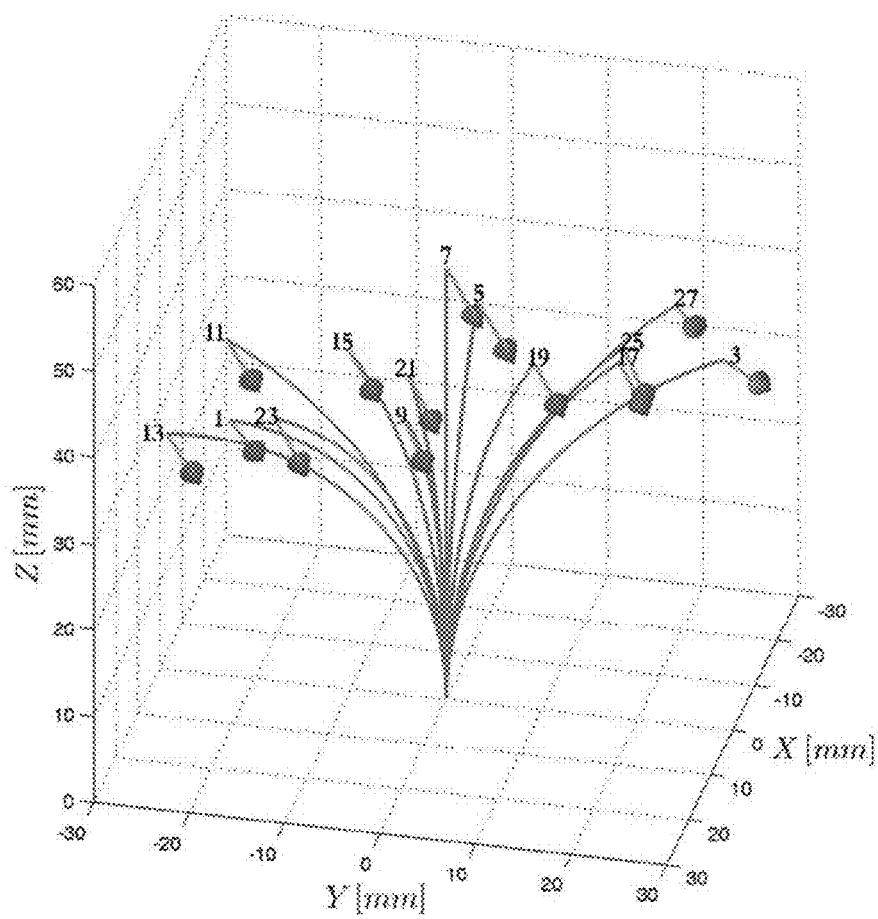
FIG. 12 is a graph illustrating poses of the continuum robot during sensitivity analysis of the compliant motion controller using the experimental system of FIG. 11.
FIG. 15 is a table providing mean pose error and standard deviation of the nominal kinematics from magnetic sensor measurements during sensitivity analysis of the compliant motion controller using the experimental system of FIG. 11.
Figure 14:
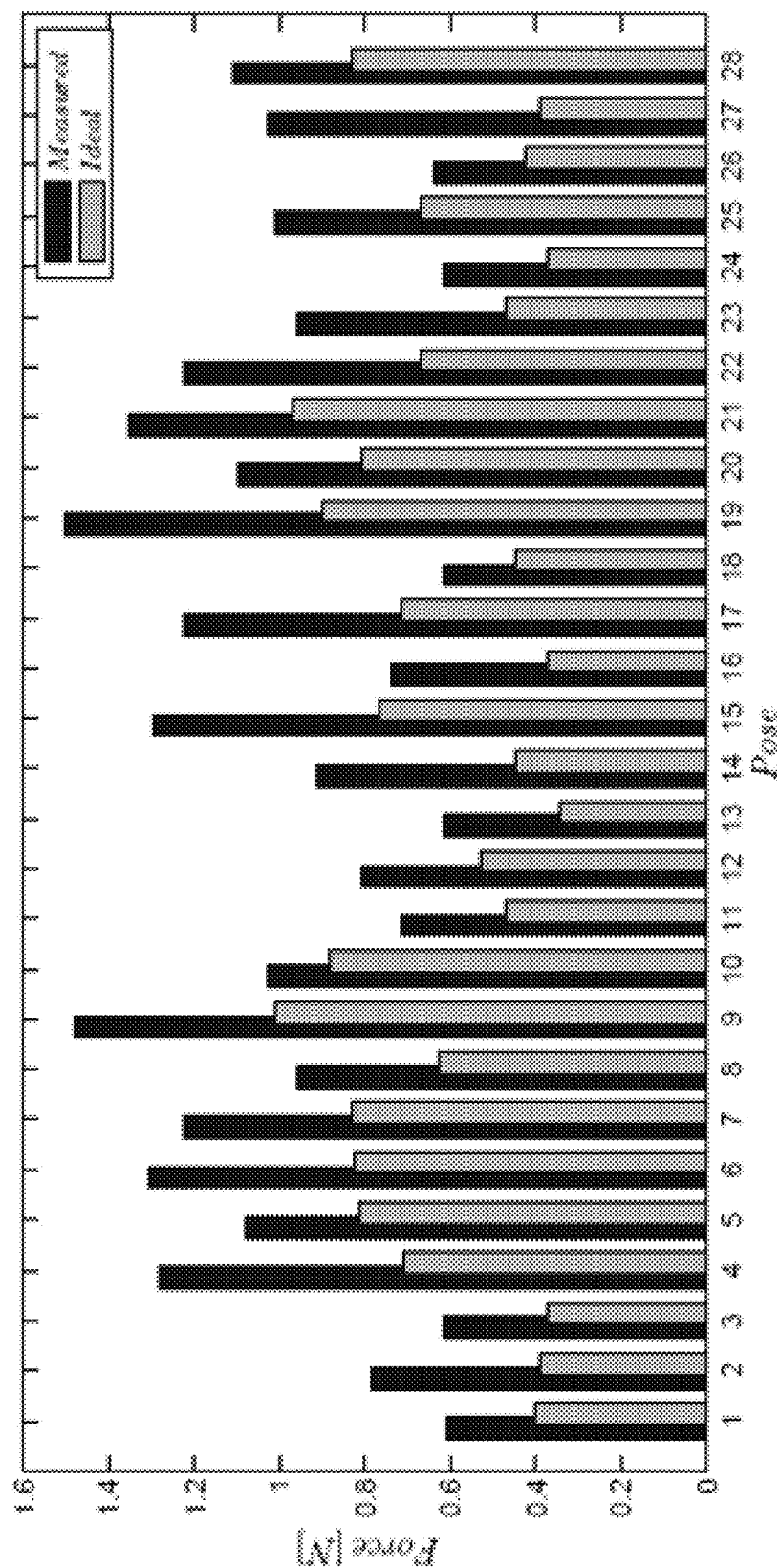
FIG. 14 is a graph illustrating measured and theoretical minimum forces required for compliant motion during sensitivity analysis of the compliant motion controller using the experimental system of FIG. 11.

Sensitivity measurements were recorded for 28 poses shown for the odd samples in FIG. 12. The experimental data is presented in FIGS. 13 and 14. Poses were selected throughout the workspace to ensure a distribution with load directions varying relative to the pose angle δ. The mean pose error and standard deviation of the nominal kinematics from the measured pose of the magnetic sensors is given in FIG. 15. Note at poses in which θ=~90°, the accuracy of δ as reported by the magnetic tracking system 1108 reduces significantly due to a configuration singularity in the magnetic tracking system 1108. Poses 7 and 20, corresponding to configurations θ=90° and θ=84°, respectively, were therefore excluded from the error calculation for $\delta_1$. The accuracy verifies the nominal kinematics of the single segment and these values were used for the subsequent analysis. The mean perturbation force required to induce motion under the experimental conditions was 0.99 N with a standard deviation of 0.28 N. The maximal force required to induce motion was 1.5 N.

The sensitivity measurements provide an opportunity to evaluate the contribution of the model uncertainties and the compensation by v-SVR. Under ideal conditions in which the generalized force is undisturbed by uncertainty, equation (15), the applied force required to induced motion can be estimated as the minimum force required to exceed the motion threshold defined by equation (52). The minimum force required to exceed the threshold in the direction of the applied force measured for each pose based on the idealized model is provided in addition to the measured force in FIG. 14. The average difference between the measured and ideal force was 0.37 N with a standard deviation of 0.14 N. Thus, the data show that model uncertainty contributes significantly to the sensitivity of the controller.

Noting the experimental setup is sized appropriately for use in exploration and intervention during minimally invasive sinus surgery, the compliant controller for this robot demonstrated adequate sensitivity for this application. Average interaction forces for functional endoscopic sinus surgery have been measured at 2.21 N and forces required to breach the sinus walls ranged between 6.06 N and 17.08 N. The compliant motion controller demonstrated in these experiments obtains a comfortable margin of safety for exploration and interaction.

Figure 16:
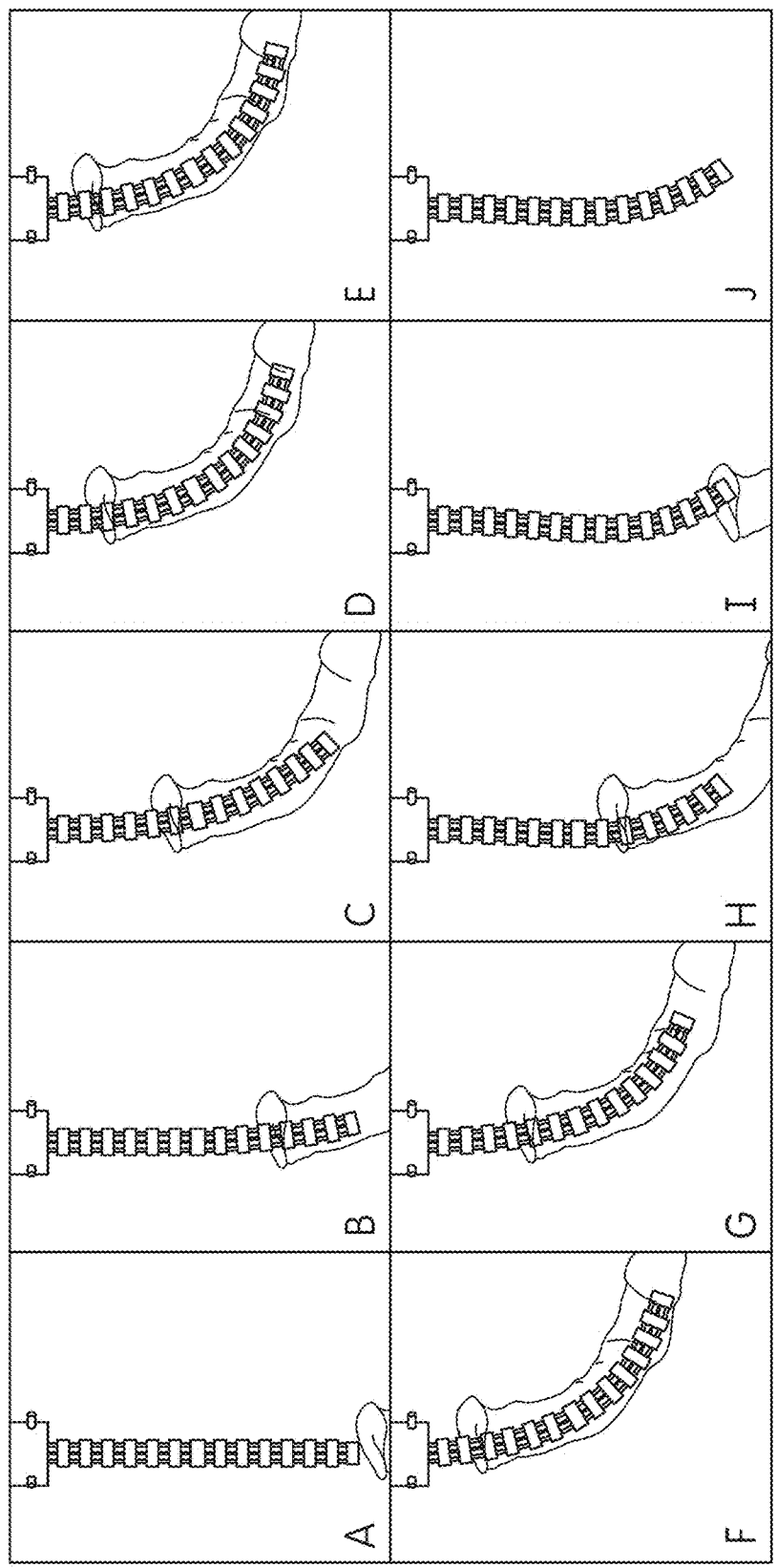
FIG. 16 is a series of images showing compliant insertion of a continuum robot into a cavity of unknown size and shape.

To evaluate the controller in the setting of an application, a two segment continuum robot was inserted into an acrylic tube with a three-dimensional shape comprised of multiple out of plane bends. The tube was mounted to an insertion stage that autonomously brought the tube into contact with the robot in a manner analogous to blind insertion into a cavity and subsequent retraction. The controller had no prior knowledge of the geometry of the tube or the path plan of the insertion stage. As illustrated in FIG. 16, the controller successfully complied with the confined complex shape despite a moving contact location unknown to the controller.

Figure 17:
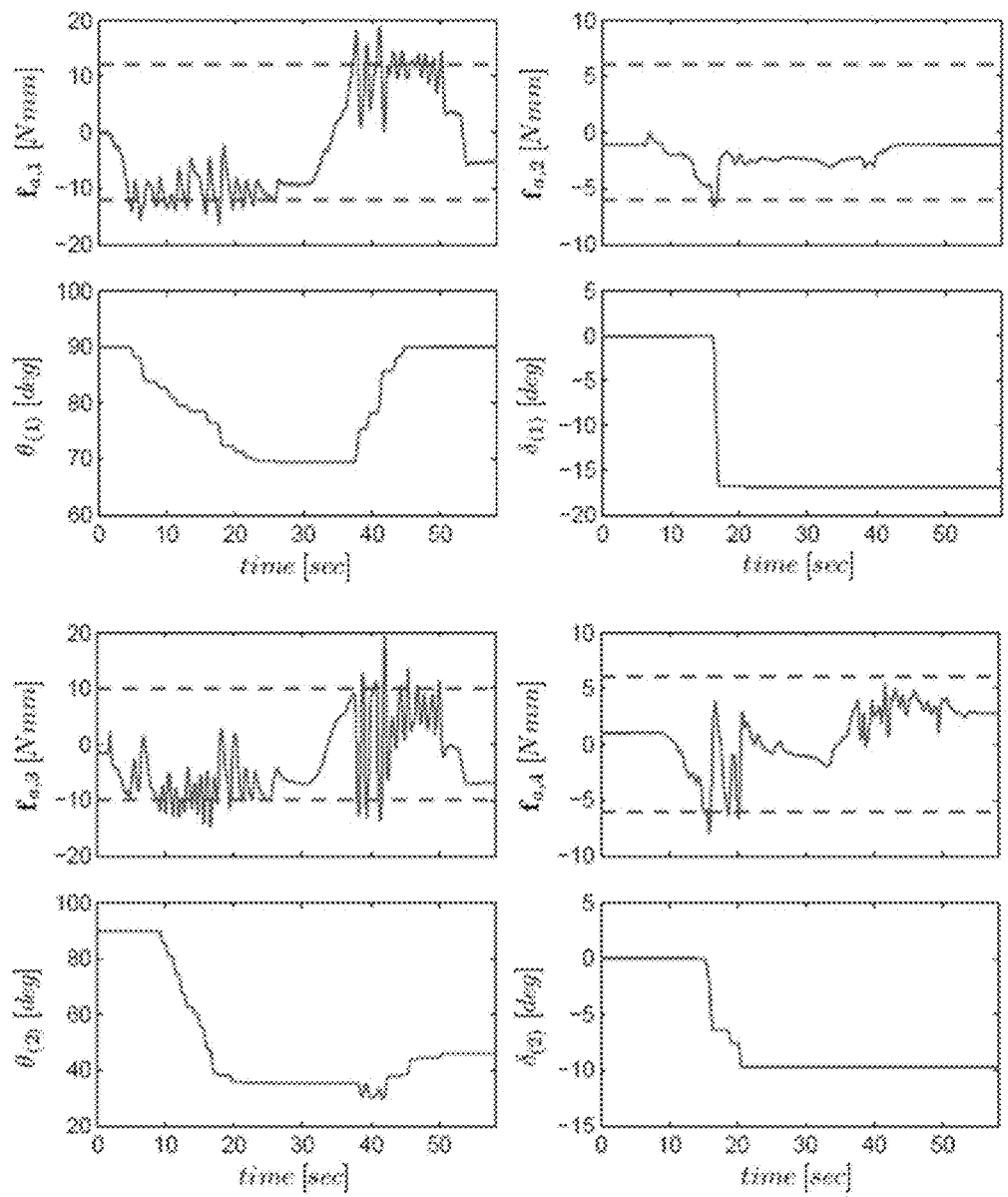
FIG. 17 is a series of graphs illustrating reaction data for the compliant insertion of FIG. 16.

The generalized force estimates during insertion and retraction are presented in FIG. 17. The data display the effect of the threshold on the motion of the system when subject to external perturbations. Generalized force magnitudes below the threshold for motion, denoted by the dashed lines in FIG. 17, are filtered and do not cause motion of the continuum robot. As the generalized force exceeds the threshold, the controller rapidly moves to reduce the force to a level below the threshold. It should be noted that the controller is agnostic to the location of contact and does not therefore require location information for minimization of the environment contact. The results demonstrate the utility of the algorithm for compliant motion control at unknown locations along the length of a continuum robot.

Trans-Nasal Throat Surgery

Minimally Invasive Surgery of the throat is predominantly performed trans-orally. Although trans-oral (TO) access provides a scarless access into the airways, its outcomes are affected by complications, high cost, and long setup time. Continuum robotic systems—such as described herein—can be used to provide trans-nasal (TN) access to the throat. Furthermore, as described below, a hybrid position/compliant motion control of a rapidly deployable endonasal telerobotic system can also be used to safely manipulate the robot during trans-nasal access. The system uses a unique 5 mm surgical slave with force sensing capabilities used to enable semiautomation of the insertion process. Working channels in the continuum robot allow the deployment of surgical tools such as a fiberscope, positioning sensors, grippers, suction tubes, cautery, and laser fibers. The treatment of vocal fold paralysis is chosen as a benchmark application and a feasibility study for collagen injection is conducted. Experiments on a realistic human intubation trainer demonstrated successful and safe TN deployment of the end effector and the feasibility of robotic-assisted treatment of vocal nerve paralysis.

Figure 18A:
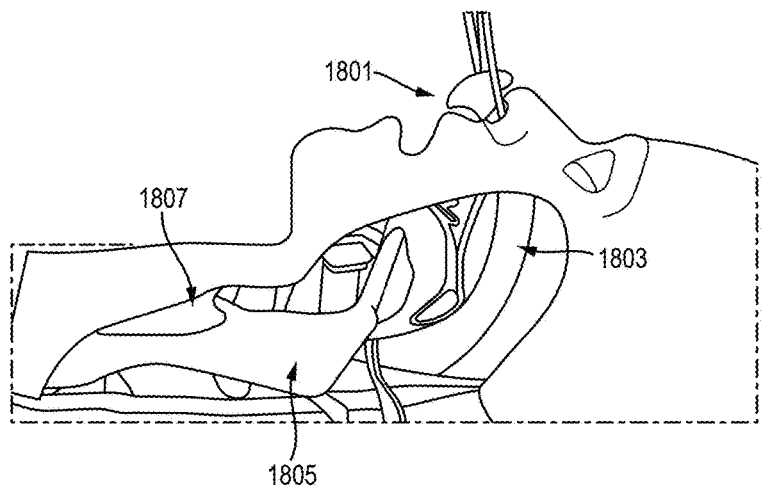
FIGS. 18A, 18B, and 18C are cutaway views of a continuum robot being positioned at a location in the throat of a patient through trans-nasal access.
Figure 18B:
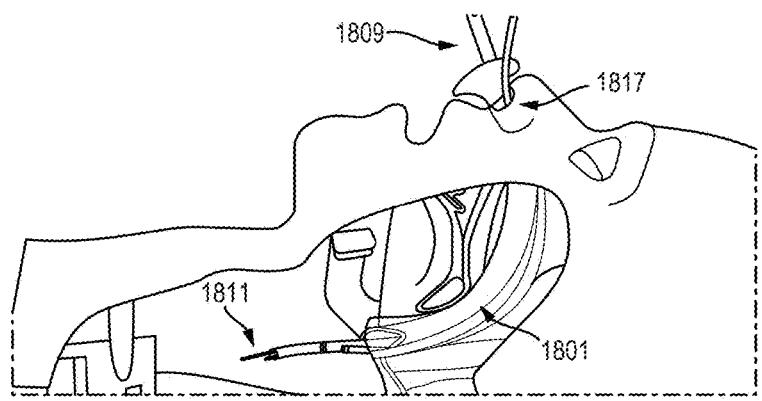
Figure 18C:
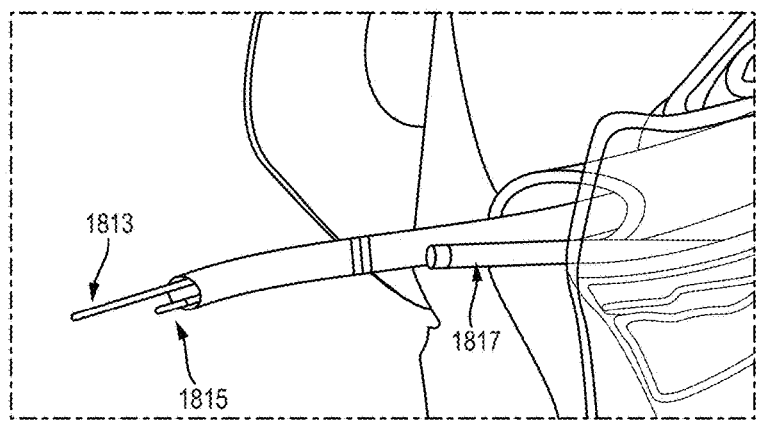

FIGS. 18A, 18B, and 18C illustrate an example of a robotic system for trans-nasal (TN) access to the throat. A nasopharyngeal tube 1801 is inserted into the nasal cavity 1803 through the nose. The continuum robot is extended through the pharynx 1805 to reach a surgical site at the larynx 1807. As shown in FIG. 18B, the robotic stem 1809 is inserted into the nasopharyngeal tube 1801 and the continuum robot 1811 extends from the distal end of the nasopharyngeal tube 1801 at the surgical site. In this example—as illustrated in FIG. 18C, the distal end of the continuum robot 1811 includes a needle 1813 for performing vocal fold repair at the surgical site and a fiberscope 1815. A bronchoscope 1817 is also inserted with the robot through the nasal cavity 1803. The end-effector of the continuum robot 1811 is composed of both active and passive multi-backbone continuum segments. A hybrid motion/compliance controller assists the surgeon during the insertion phase by actively complying to the unknown environment while allowing the operator to control the insertion depth and speed.

Figure 19:
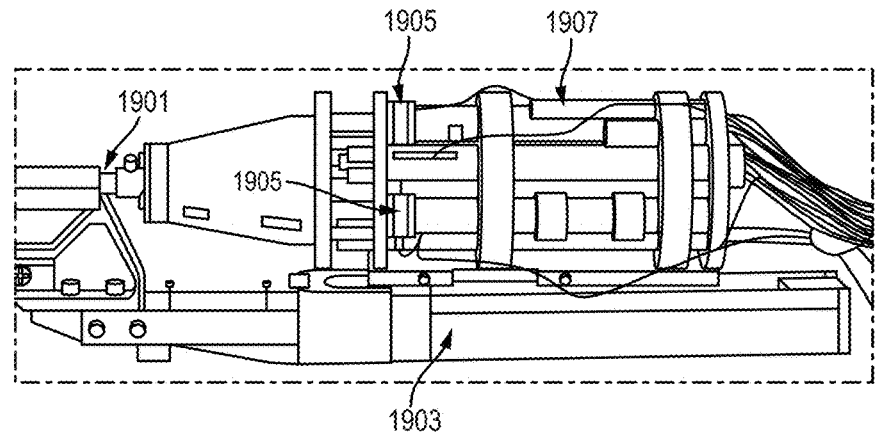
FIG. 19 is an elevation view of an actuation unit for a continuum robot.

The robotic system of FIG. 18A is operated using a dexterous 5 DoF continuum manipulator, a Sensable Phantom Omni, an Ascension 3D Guidance trakSTAR 2 with flat metal immune transmitter, a 4 mm bronchoscope, and a 1.2 mm fiberscope. FIG. 19 illustrates an example of an actuation unit that drives the movement of the continuum robot on seven controlled axes, of which six control the two continuum segments and one controls the insertion depth into the nasopharyngeal tube. The actuation unit includes a robotic stem 1901, a linear slider 1903 (which controls the extension of the continuum robot from the robotic stem 1901), one or more load cells 1905 (for monitoring actuation forces), and one or more potentiometers 1907 (for redundant positioning information).

The system can operate in both passive and semi-active modes. The passive mode is based on a standard telemanipulation architecture where the operator guides the end-effector via a master manipulator (the Phantom Omni) while observing endoscopic images provided by the in-hand fiberscope. The semi-active mode is used to reach the surgical site. During the semi-active mode the surgeon commands the insertion depth while the continuum manipulator autonomously complies with the anatomy using a variation of the compliance motion controller described above.

Figure 20:
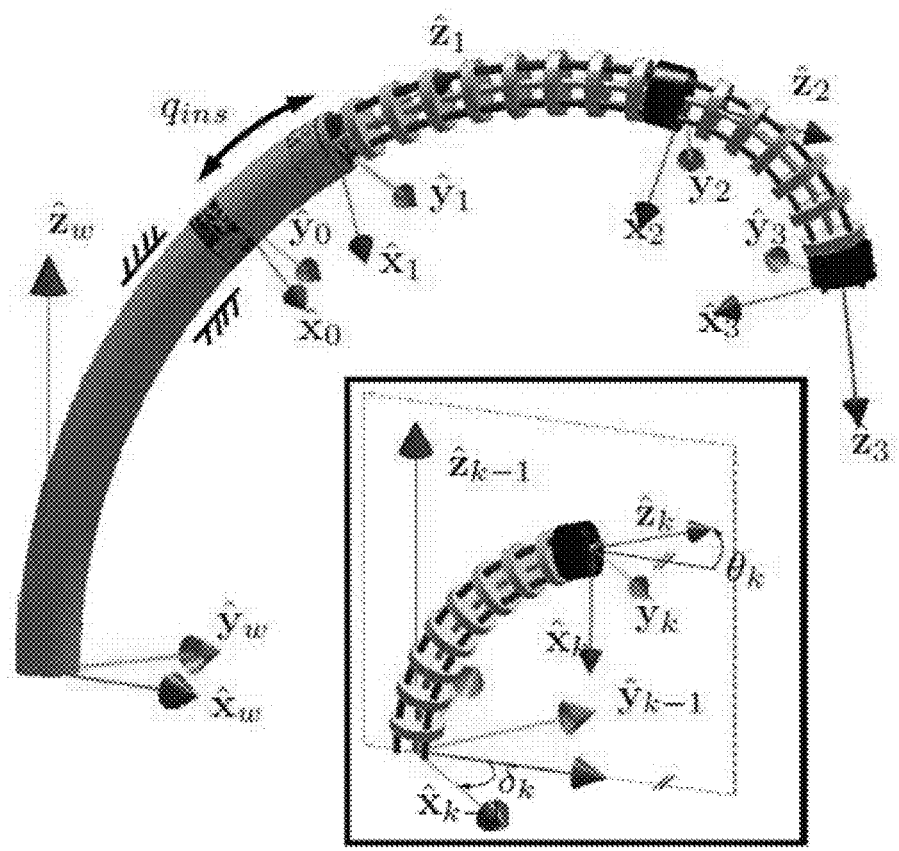
FIG. 20 is a perspective view of a posed continuum robot.

FIG. 20 illustrates a surgical slave portion of the robotic system that is composed of a flexible passive stem and two active segments. Each 5 mm segment is composed of four super-elastic NiTi backbones (one central and three secondary ones) that provide two DoF for bending in any direction. An additional DoF is provided by the linear stage of the actuator (described in FIG. 19 above), which controls the insertion of the base of continuum arm. The robotic arm has three 1.8 mm lumens that allow for the deployment of surgical instruments. In order to compensate for the unknown shape of the passive segment constrained by the nasopharyngeal tube, a 0.9 mm 6 DoF electro-magnetic sensor is attached to the base of the two-segment continuum robot. The metal immune flat transmitter makes the system robust to surrounding metal and easy to place under the patient's head.

FIG. 20 illustrates five coordinate systems that are defined to describe the direct kinematics of the surgical slave: the world frame $B_w$ defined by vectors $\{\hat{x}_w, \hat{y}_w, \hat{z}_w\}$, the frame attached to the exit of the nasopharyngeal tube $B_0$ defined by vectors $\{\hat{x}_0, \hat{y}_0, \hat{z}_0\}$, the base frame of the actively bending continuum robot $B_1$ defined by vectors $\{\hat{x}_1, \hat{y}_1, \hat{z}_1\}$, the base frame of the second segment $B_2$ defined by vectors $\{\hat{x}_2, \hat{y}_2, \hat{z}_2\}$, and the end effector frame $B_3$ defined by vectors $\{\hat{x}_3, \hat{y}_3, \hat{z}_3\}$.

The position and orientation of end-effector frame $B_3$ in $B_0$ may be described by the following augmented configuration space vector:

$$\Psi = [\theta_1 \delta_1 q_{ins} \theta_2 \delta_2 \theta_3 \delta_3]^T \quad (53)$$

where, $q_{ins}$ is the insertion depth and angles $\theta_k$ and $\delta_1$, are defined similarly for the passive segment (k=1) and active segments (k=2, 3) as depicted in FIG. 20. Using the position and orientation of frame $B_3$ in $B_0$ is given by:

$$^0p_3 = {^0p_1} + {^0R_1}(^1p_2 + {^1R_2}{^2p_3}) \quad (54)$$

$$^0R_3 = {^0R_1}{^1R_2}{^2R_3} \quad (55)$$

where $$^{k-1}p_k = \frac{L_k}{\Theta_k}\begin{bmatrix} \cos(\delta_k)(\sin\theta_k - 1) \\ -\sin(\delta_k)(\sin\theta_k - 1) \\ -\cos\theta_k \end{bmatrix} \quad (56)$$

$$^{k-1}R_k = Rot(-\delta_k, \hat{z})Rot(-\Theta_k, \hat{y})Rot(\delta_k\hat{z}) \quad (57)$$

with: $L_1 = q_{ins}$, $L_2$, and $L_3$ being the lengths of the first and second active segments. $\theta_k = \theta_k - \pi/2$, and operator Rot(a,b) being the rotation matrix about axis b by angle a. Note that, since the first segment is passive, $\theta_1$ and $\delta_1$ are not directly controllable. In the remainder of this example, we assume that $\theta_1$ and $\delta_1$ and the origin of from $B_1$ are measured by a magnetic tracker (the position and the orientation frame $B_1$ is known). Hence, the forward kinematics is calculated using $\theta_1$ and $\delta_1$ and $B_1$ along with joing values $q_i$, $i=1 \ldots 6$.

The configuration space vector $\Psi$ relates to the joint space vector as $$q(\Psi) = [q_{ins} q_2(\Psi)^T q_3(\Psi)^T]^T \quad (58)$$

where $q_2$ and $q_3$ are the amount of pushing-pulling on the secondary backbones of active segments 2 and 3. In particular $$q_2 = r\begin{bmatrix} \Theta_1\cos(\delta_2) - \Theta_0\cos(\delta_0) \\ \Theta_1\cos(\delta_2 + \beta) - \Theta_0\cos(\delta_0 + \beta) \\ \Theta_1\cos(\delta_2 + 2\beta) - \Theta_0\cos(\delta_0 + 2\beta) \end{bmatrix} \quad (59)$$

$$q_3 = r\Theta_2\begin{bmatrix} \cos(\delta_2) \\ \cos(\delta_2 + \beta) \\ \cos(\delta_2 + 2\beta) \end{bmatrix} \quad (60)$$

$$\theta_0 = \pi/2 - \text{atan2}\left(\sqrt{R_{13}^2 + R_{23}^2}, R_{33}\right) \quad (61)$$

$$\delta_0 = -\text{atan2}(R_{23}, R_{13}) \quad (62)$$

where $\beta = 2\pi/3$, r is the radial distance of the secondary backbone from the center of the base disk, $\theta_0 = \theta_0 - \pi/2$, $\theta_1 = \theta_1 - \pi/2$, and $R_{ij}$ is element ij of rotation matrix $^wR_1$ obtained from the magnetic sensor placed at the based of the first active segment. Note that angles $\theta_0$ and $\delta_0$ allow us to work in local frame $B_0$ decoupling the kinematics of the distal active and passive segments from shape variations of the passive stem.

FIG. 21 illustrates the control architecture of the telesurgical system. Control inputs and electro-magnetic orientation information are both received at 125 Hz over the Local Area Network while encoder and actuation force signals are sampled at 1 kHz and 5 kHz respectively. The conventional hybrid motion/compliance control is adopted in which two separate controllers independently provide motion and compliance control commands. However, the hybrid motion/compliance control approach is adapted to our continuum robot by decomposing the control task in configuration space rather than in task space. The projection matrices $\Omega$ and $^-\Omega$ ensure that the control commands are projected into subspaces for motion and compliance control. Joint-level commands to the actuators are then obtained through the inverse position of the continuum manipulator and the required model-based actuation compensation. The following details describe the specific implementation of our approach.

(1) Compliant Motion Control:

Compliance Motion Control (CMC), as described above, allows multi-backbone continuum robots with intrinsic actuation sensing to autonomously steer away from constraints without a priori knowledge of the contact nor the external wrench. In the following, the CMC control mechanism is modified in order to use only information about actuation forces sensed on the most distal segment. This control law allows the robot to actively comply to the circle-shaped nasopharyngeal tube. If actuation force information on the second active segment is available, the actuation force error is defined as:

$$\tau_{e_3} = \tau_3 - \bar{\tau}_3 \quad (63)$$

where $\tau_3$ are the expected actuation forces and $^-\tau_3$ are the sensed actuation forces acting on the third segment respectively. We now project the actuation force error, $\tau_{e_3}$, into the configuration space of the distal segment obtaining the generalized force error:

$$f_{e_3} = J_{q\psi}^T \tau_{e_3} \quad (64)$$

where $J_{q\psi}$ is the Jacobian matrix that relates the configuration space velocities to the joint space velocities.

Hence, the desired configuration space velocity vector that steers the robot away from the unknown contact is:

$$\dot{\Psi}_c = \Phi K_{\psi 2}^{-1} f_{e_3} \quad (65)$$

where $K_{\psi 2}$ is the configuration space stiffness matrix of the second segment and $$\Phi = \begin{bmatrix} 0 & 1 & 0 & 1 & 0 \\ 0 & 0 & 1 & 0 & 1 \end{bmatrix}^T \quad (66)$$

Note that Equation (65) is a simplification of the algorithm presented above for compliant motion control for multiple segments. In the case of TN insertion, assuming an overall circular shape of the entire manipulator, both segments need to bend by the same angle in order pass through the nasopharyngeal tube.

(2) Motion Control:

Telemanipulation of the surgical slave is achieved by defining a mapping between the movement of the master's end-effector and the desired motion directions in the fiberscope image space as shown in FIGS. 22A, 22B, and 22C. Because of the difficulties in accurately controlling the two active segments and the long unknown-shaped passive stem, the movement of the Phantom Omni manipulator control (shown in FIG. 22B) is mapped only to 3 DoF of the most distal segment in this example: 1 DoF of insertion and 2 DoF of bending (as in a conventional bronchoscope). Therefore, once the robot is inserted (shown in FIG. 22A), the first segment is bent ($\theta_1=60$) in the direction of the vocal folds ($\delta_1=0$). The user advances the robot in the direction of $\hat{z}_f$ (insertion) and tilts about axes $\hat{x}_f$ and $\hat{y}_f$ in fiberscope-attached frame. The fiberscope-attached frame (shown in FIG. 22C) is related to $B_3$ by a known fixed rotation. This movement in image space is first mapped to the movement of the master stylus $\{\hat{x}_{ms}, \hat{y}_{ms}, \hat{z}_{ms}\}$ and then to the movement of the distal segment frame $\{\hat{x}_3, \hat{y}_3, \hat{z}_3\}$.

The desired position and orientation of distal segment are given as follows:

$$^2p_{3,des} = {^2p_{3,curr}} + {^2R_{3,curr}}p_{des,master} \quad (67)$$

$$^2R_{3,des} = {^2R_{3,curr}}R^T R_{des,master}R \quad (68)$$

where matrix R defines the transformation between the camera-attached frame (FIG. 22C) and the master's stylus (FIG. 22B). Once the desired pose is computed, the desired twist $t_{des}$ is computed and the desired configuration space velocities are obtained as follows:

$$\begin{bmatrix} \dot{q}_{ins} \\ \dot{\theta}_2 \\ \dot{\delta}_2 \end{bmatrix} = (\Gamma \Sigma J_2)^{-1} \Gamma \Sigma t_{des}. \quad (69)$$

In Equation (69), $J_2$ is the Jacobian matrix of the distal segment:

$$J_2 = \begin{bmatrix} 0 & L_2 c_{\delta_2} \frac{\Theta_2 c_{\theta_2} - s_{\theta_2} + 1}{\Theta_2^2} & -\frac{L_2 s_{\delta_2}(s_{\theta_2} - 1)}{\Theta_2} \\ 0 & -L_2 s_{\delta_2} \frac{\Theta_2 c_{\theta_2} - s_{\theta_2} + 1}{\Theta_2^2} & \frac{L_2 c_{\delta_2}(s_{\theta_2} - 1)}{\Theta_2} \\ 1 & L_2 \frac{\Theta_2 \Sigma s_{\theta_2} + c_{\theta_2}}{\Theta_2^2} & 0 \\ 0 & -s_{\delta_2} & c_{\delta_2} c_{\theta_2} \\ 0 & -c_{\delta_2} & -s_{\delta_2} c_{\theta_2} \\ 0 & 0 & -1 + s_{\theta_2} \end{bmatrix} \quad (70)$$

matrix $\Sigma$ transforms the desired twist into gripper frame $$\Sigma = \begin{bmatrix} {}^2 R_{3,curr}^T & 0 \\ 0 & {}^2 R_{3,curr}^T \end{bmatrix} \quad (71)$$

And selection matrix $\Gamma$ defines a desired subtask $$\Gamma = \begin{bmatrix} 0 & 0 & 1 & 0 & 0 & 0 \\ 0 & 0 & 0 & 1 & 0 & 0 \\ 0 & 0 & 0 & 0 & 1 & 0 \end{bmatrix}. \quad (72)$$

In this example, matrix $\Gamma$ selects the third, fourth, and fifth rows of the Jacobian matrix allowing to control only 3 DoF: translation along $z_3$ and tilting about $x_3$, $y_3$. As a result, we only invert a square 3×3 matrix and control only the desired DoFs.

Finally, the augmented desired configuration space velocity vector is given as follows:

$$\dot{\Psi}_m = [\dot{q}_{ins} \ 0 \ 0 \ \dot{\theta}_2 \ \dot{\delta}_2]^T \quad (73)$$

(3) Projection Matrices:

Depending on the operational mode (insertion or telemanipulation) the configuration space $\Psi$ can be partitioned in directions in which motion needs to be controlled, T, and directions in which compliance needs to be controlled, C. Similar to wrench and twist systems in the hybrid motion/force control formulation, these two spaces, T and C, are orthogonal and their sum returns the configuration space $\Psi$ (T+C=$\Psi$). It is, therefore, possible to construct two projection matrices, $\Omega$ and $\bar{\Omega}$, that project desired configuration space velocities into the motion space T and into the compliance space C:

$$\Omega = T(T^T T)^\dagger T^T \quad (74)$$

$$\bar{\Omega} = I - \Omega \quad (75)$$

where T is a 5×m matrix in which its columns define a base of T and superscript † indicate the pseudo-inverse. For example, in the case of compliant insertion, configuration variables $q_{ins}$, $\delta_2$, and $\delta_3$ will be position-controlled while variables $\theta_2$ and $\theta_3$ will be compliance-controlled allowing the segment to adapt to the shape of the nasal conduit. Hence, matrix T is defined as:

$$T = \begin{bmatrix} 1 & 0 & 0 & 0 & 0 \\ 0 & 0 & 1 & 0 & 0 \\ 0 & 0 & 0 & 0 & 1 \end{bmatrix}^T \quad (76)$$

(4) Actuation Compensation:

The desired joint variables are computed using a theoretical kinematics model and a model-based actuation compensation.

Motion Force Control of Multi-Backbone Continuum Robots

This section presents a general framework for hybrid motion/force control of continuum robots. The examples described below assume that the kinematic model is known and that the robot is equipped with a device for measuring or estimating environmental interaction forces. This information can be provided by a dedicated miniature multi-axis force sensor placed at the tip of the robot or by an intrinsic wrench estimator of the types. A multi-backbone continuum robot with intrinsic wrench estimation capabilities is used to demonstrate the hybrid motion/force control framework. The following assumptions specifically apply to multi-backbone continuum robots with intrinsic force sensing. Different assumptions are necessary for different types of robots but the fundamental control framework remain invariant.

Assumption 1: The continuum robot bends in a circular shape and gravitational forces are negligible.

Assumption 2: The continuum robot is able to sense actuation forces via load cells placed between each actuation line and its actuator.

Assumption 3: The geometric constraint is known and the environment is rigid. This information is used for both the hybrid motion/force controller and the intrinsic wrench estimation. However, because of the innate compliance of continuum robots and as demonstrated by experimental results, an exact knowledge of the geometric constraint is not necessary.

Figure 23:
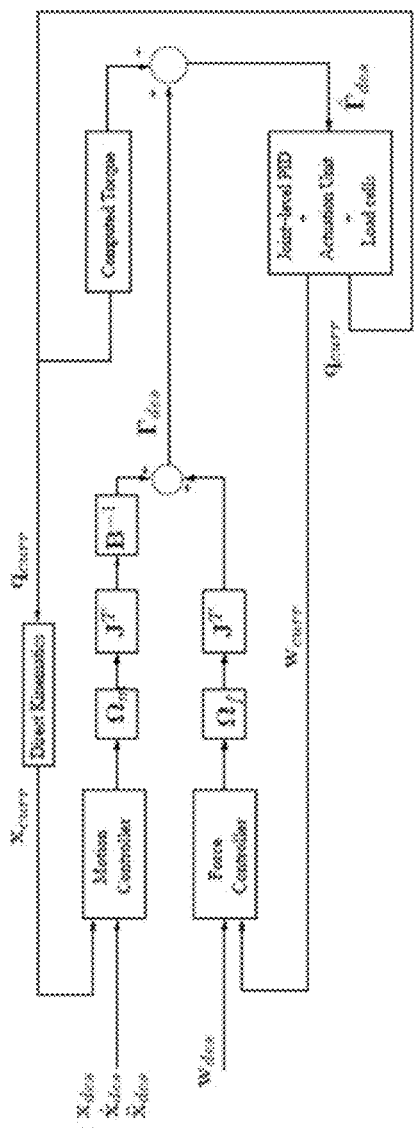
FIG. 23 is a functional block diagram of a hybrid motion/force control system for manipulation of a rigid-link robotic system.

FIG. 23 shows an example of a hybrid motion/force controller for rigid-link robot manipulators. Motion and force controllers provide two separate control signals that are first projected into allowable motion and force directions (using projection matrices $\Omega$ and $\bar{\Omega}$) and then merged into the joint-space of the manipulator. Motion commands are first transformed into task-space wrenches using the inverse of the inertia matrix B and then into joint-torque commands using the transpose of the Jacobian matrix J. The desired joint-torque vector $\Gamma$ is then added to the feedback linearization term that compensates for non-linearities (e.g. coriolis/centrifugal and gravitational effects) and fed to the joint-space PID controller.

Figure 24:
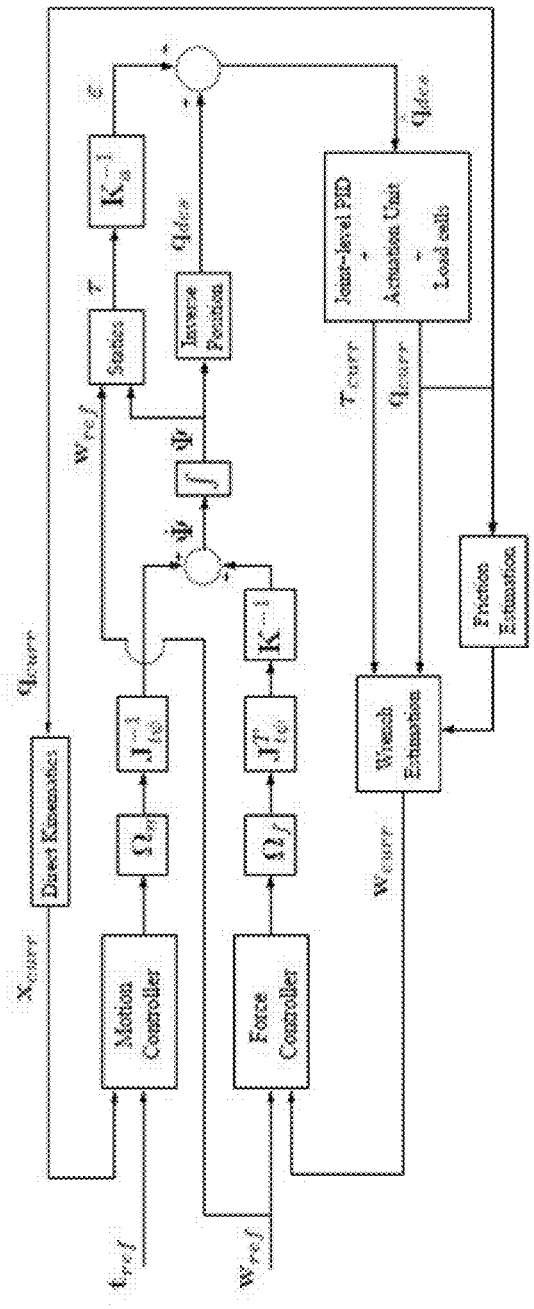
FIG. 24 is a functional block diagram of a hybrid motion/force control system for manipulation of a multi-backbone continuum robot.

FIG. 24 shows a hybrid motion/force controller for multi-backbone continuum robots with intrinsic force sensing. As in the example of FIG. 23, two separate controllers produce motion and force commands that are then projected into allowable motion/force directions using projection matrices $\Omega$ and $\bar{\Omega}$. Hence, the motion and force commands are projected into the configuration space velocity of the continuum manipulator using respectively the inverse of the Jacobian matrix $J_{r\psi}$ and a composition of the transpose of the matrix $J_{r\psi}$ and the configuration space compliance matrix $K^{-1}$. The configuration space compliance matrix provides a mapping between the change in task-space wrenches and the change in configuration space velocities. Finally, using the closed-form inverse position of the manipulator, the theoretical desired joint-space positions $q_{des}$ are obtained. Similar to the feedback linearization term in the example of FIG. 23, an additional term is obtained through the statics of the continuum manipulator and the stiffness of the actuation lines. This term include both an actuation compensation term for the applied wrench at the tip of the robot and a compensation term for extension and friction in the actuation lines.

Control Architecture—A First-Order Model of Contact:

Hybrid motion/force control aims at controlling the interaction of two rigid bodies by decoupling control inputs into allowable relative motions and constraining wrenches. The control inputs are specifically generated to maintain contact between the two bodies by simultaneously generating motion directions that do not break the contact state and apply the desired interaction wrench. For example, in the case of frictionless point contact (as illustrated in FIGS. 25A and 25B), body 1 can translate along axes x and y, rotate about axes $\hat{x}$, $\hat{y}$, and $\hat{z}$, and apply a force along axis $\hat{z}$, i.e. the normal vector between body 1 and body 2.

Regardless of the type of contact, it is possible to define two dual vector sub-spaces, one containing wrenches $F^6$, and the other containing motion screws $M^6$. The reciprocal product between these two spaces is defined as the rate of work done by a wrench $f_i$ acting on a motion screw $m_j$. In the case of rigid bodies, under conservative contact, the bases of the two spaces must satisfy the reciprocity condition. At any given time, the type of contact between the two rigid bodies defines two vector sub-spaces: a n-dimensional space of normal vectors $N \subseteq F^6$ and a (6-n)-dimensional space of tangent vectors $T \subseteq M^6$, where n is the degree of motion constraint. The bases of these two spaces can be defined by a 6×n matrix N and a 6×(6-n) matrix T. The columns of N and T are respectively any n linearly independent wrench in N and any 6-n linearly independent motion screw in T. As a consequence of the reciprocity condition and the contact constraint, the scalar product of any column of N with any column of T is zero, i.e.

$$N^T T = 0 \tag{77}$$

Figure 25B:
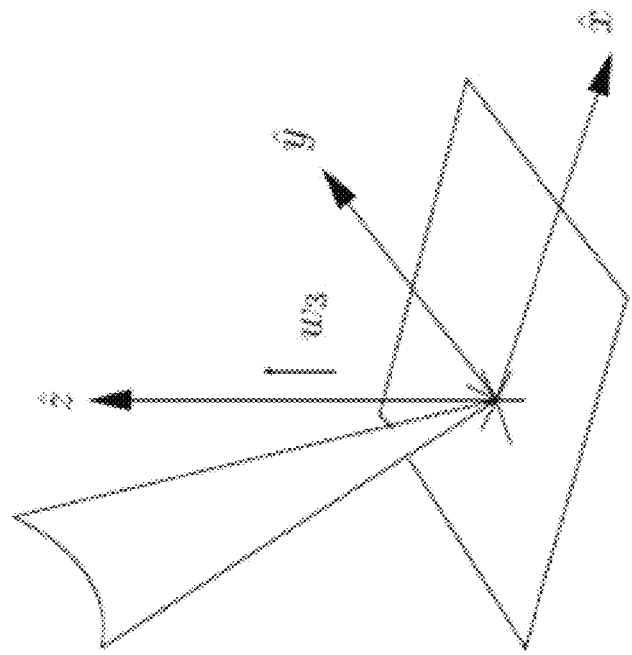
FIGS. 25A and 25B are graphs of wrench and twist screw bases corresponding with a frictionless point contact.
Figure 25A:
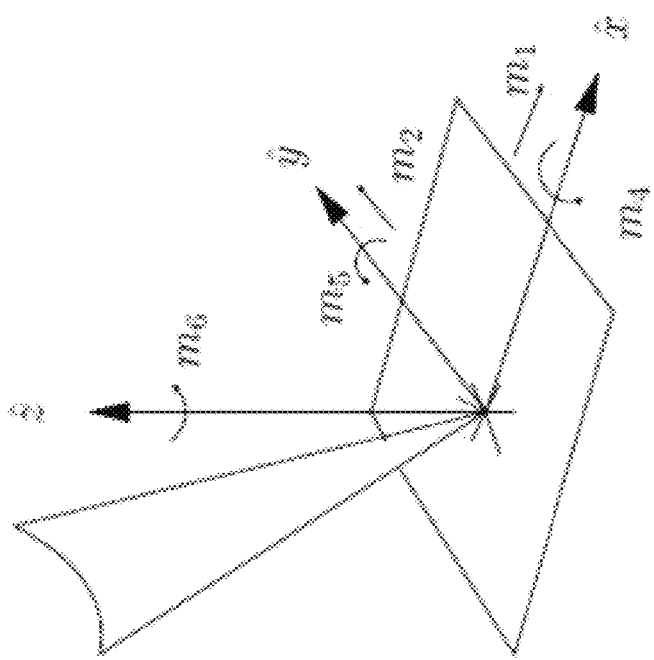

For example, for the contact constraint depicted in FIGS. 25A and 25B, matrices N and T are given by:

$$N = \begin{bmatrix} 1 & 0 & 0 & 0 & 0 \\ 0 & 1 & 0 & 0 & 0 \\ 0 & 0 & 0 & 0 & 0 \\ 0 & 0 & 1 & 0 & 0 \\ 0 & 0 & 0 & 1 & 0 \\ 0 & 0 & 0 & 0 & 1 \end{bmatrix}, T = \begin{bmatrix} 0 \\ 0 \\ 1 \\ 0 \\ 0 \\ 0 \end{bmatrix} \tag{78}$$

Although in many situations matrices N and T are simply the composition of canonical vectors in $\mathbb{R}^6$ and can be obtained by inspection, this is not the case when dealing with complex interaction tasks and multi-point contacts.

The efficacy of hybrid motion/force control stems from its ability to produce adequate motion and force control inputs that do not violate the reciprocity condition (Equation 77). The reciprocity of the control inputs is enforced by projecting each control input into the correct subspace by premultiplication of a projection matrix. We, therefore, define two projection matrices $\Omega_f$ and $\Omega_m$ that project any control input into consistent wrenches and twists respectively:

$$\Omega_f = N(N^T N)^{-1} N^T$$

$$\Omega_m = T(T^T T)^{-1} T^T = I - \Omega_f \tag{79}$$

According to the classical formulation of hybrid motion/force control, the frame-work inputs are defined by the desired twist $t_{ref} = [v_{ref}^T \ w_{ref}^T]^T$ and the desired interaction wrench at the operational point $w_{ref} = [f_{ref}^T \ m_{ref}^T]^T$.

At any given time, the wrench error is given by:

$$w_e = w_{ref} - w_{curr} \tag{80}$$

where $w_{curr}$ is the sensed wrench.

The output of the motion controller, $t_{des}$, is first projected onto the allowed motion space $M^6$ via projection matrix $\Omega_m$ as defined in equation (79) and then onto the configuration space velocity of the manipulator via the pseudo-inverse of the Jacobian matrix $J_{r\psi}^\dagger$:

$$\dot{\Psi}_m = J_{r\psi}^\dagger \Omega_m t_{des}. \tag{81}$$

One the other hand, the output of the motion controller $w_{des}$ can be obtained with a conventional PI control schemes:

$$w_{des} = K_{f,p} w_e + K_{f,i} \int w_e. \tag{82}$$

Similarly to the motion controller, the desired wrench wdes is first projected into the allowed wrench space $F^6$ via projection matrix $\Omega_f$ as defined in equation (79), then into the generalized force space via the transpose of the Jacobian matrix $J_{r\psi}$. The generalized force is the projection of the task-space wrench acting at the end effector into the configuration space of the manipulator. Finally into the configuration velocity space of the continuum manipulator via the configuration space compliance matrix $K_\Psi^{-1}$:

$$\dot{\Psi}_f = K_\Psi^{-1} J_{r\psi}^T \Omega_f w_{des}. \tag{83}$$

Using equations (81) and (83) the motion and force control inputs are merged into a configuration space velocity vector $\Psi$ that does not violate the contact constraint:

$$\dot{\Psi} = \dot{\Psi}_m + \dot{\Psi}_f \tag{84}$$

Equation (84) provides the desired configuration of the continuum manipulator that accomplishes both the desired motion and force tasks without violating the contact constraint. The next step in the control architecture is to generate joint-level commands to accomplish the desired tasks. Because of the flexibility of the arm, actuation compensation is required for both achieving the desired pose and applying the desired wrench at the end-effector. Using the statics model, the desired actuation forces $\tau_d$ are obtained as follows:

$$\tau_{des} = (J_{q\psi}^T)^\dagger (\nabla U - J_{r\psi}^T \Omega_f w_{ref}) \tag{85}$$

According to a model-based actuation compensation scheme, the desired joint-space compensation is given by:

$$\varepsilon = K_a^{-1} \tau_{des} \tag{86}$$

where $K_a^{-1}$ designates the compliance matrix of the actuation lines.

By combining equations (84) and (86), the desired joint-space control input is obtained as follows:

$$q_{des} = \hat{q}_{des}(\Psi) + \varepsilon \tag{87}$$

where $\hat{q}_{des}(\Psi)$ is the joint's positions associated with configuration ($\Psi$) according to the theoretical inverse position analysis.

The hybrid motion/force control architecture for continuum robots with intrinsic force sensing is summarized in FIG. 24. Two independent controllers provide high-level control commands for both motion and force regulation. These commands are projected into adequate force-vectors and velocity-vectors that do not violate the contact constraint and then they are projected into the configuration space of the continuum manipulator. The motion commands are projected using the inverse of the Jacobian matrix $J_{r\psi}$, while the force commands are projected using first the transpose of the Jacobian matrix $J_{r\psi}$ and then the configuration space compliance matrix $K_\psi^{-1}$. The configuration space stiffness matrix describes how a change in the external wrench direction and magnitude is related to a change in the configuration of the continuum manipulator. Once the desired configuration space vector is obtained, a model-based actuation compensation scheme is used to produce the required joint-space displacements for both configuration compensation and the acting wrench. Note that, equation (85) includes two terms: the first compensate for actuation line extension, friction, and model uncertainties, while the second term is a feedforward term that produces the desired wrench at the end-effector by actuation the manipulator in joint-space. Finally, the control input $q_{des}$ is fed into the low-level PID controller. In the case of continuum robots with intrinsic wrench estimation, there are two additional components: the friction compensation/estimation block, and the wrench estimator.

Compensation Uncertainties:

During control of the real continuum robot there will be a deviation between the desired actuation force vector $\tau_{des}$ and the sensed actuation force vector $\tau_{curr}$. This deviation is due to friction and extension in the actuation lines, perturbation of the bending shape from the ideal circular configuration, and geometric and static parameters. Thus, the sensed actuation force vectors is as follows:

$$\tau_{curr} = \tau_{des} + \lambda. \tag{88}$$

Force deviation is a function of the configurations $\Psi$ of the manipulator and the joint-space velocities $\dot{q}$. Several methods have been proposed in order to characterize friction and uncertainties. A discrete Dahl model for friction compensation in a master console may be implemented. A Dahl friction model can also be implemented into the control architecture of steerable catheters. Friction estimation and compensation can also be used in the control of concentric tube robots. A non-linear regression via Support Vector regressors might also be used to compensate for lumped uncertainties in multi-backbone multi-segment continuum robots.

Wrench Estimation:

Continuum robots with actuation force sensing allow to estimate external wrenches acting at the tip. Using a statics model, the external wrench acting at the tip of the continuum robot is given by:

$$w_{curr} = (J_{t\psi}^T)^\dagger (\nabla U - J_{q\varphi}^T(\tau_{curr} - \lambda)) + (I - (J_{t\psi}^T)^\dagger J_{t\psi}^T)\eta \tag{89}$$

where $$\eta = D^\dagger F^T S_e (w_{se} - (J_{t\psi}^T)^\dagger (\nabla U - J_{q\varphi}^T(\tau_{curr} - \lambda)))$$

$$D = (I - (J_{t\psi}^T)^\dagger J_{t\psi}^T) S_e (I - (J_{t\psi}^T)^\dagger J_{t\psi}^T)$$

$$F = (I - (J_{t\psi}^T)^\dagger J_{t\psi}^T)$$

-continued $$S_e = \begin{bmatrix} (\hat{n}_t \times \hat{n}_n)(\hat{n}_t \times \hat{n}_n)^T & 0_{3\times 3} \\ 0_{3\times 3} & I_{3\times 3} \end{bmatrix}$$

$$W_{se} = \begin{bmatrix} c_t \hat{n}_t + n_t \hat{n}_n \\ 0_{3\times 1} \end{bmatrix}.$$

$S_e$ and $W_{se}$ contain a priori knowledge of the contact constraint and guide the estimation algorithm. The a priori knowledge is defined by contact normal vector $\hat{n}_n$ and contact tangential vector $\hat{n}_t$. These two vectors define the plane in which the sensible component of the external wrench lies.

Figure 26B:
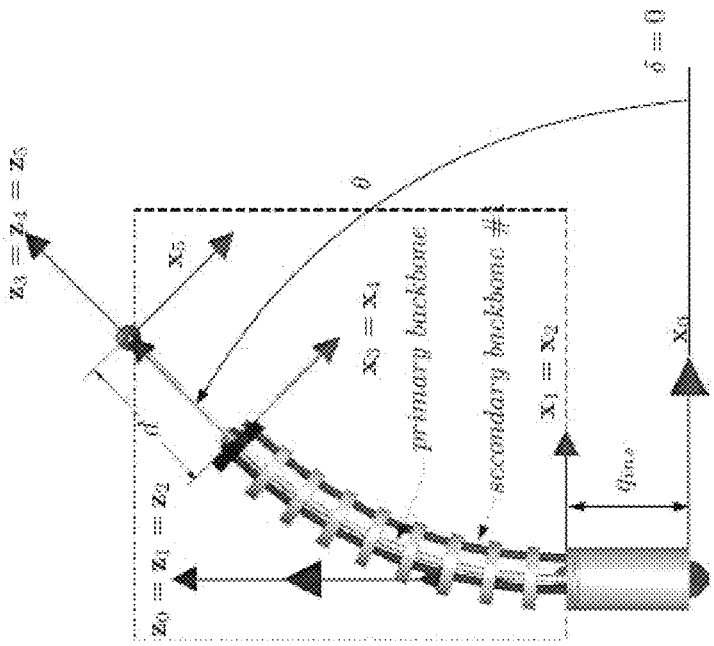
FIG. 26B is a side view of the posed continuum robot of FIG. 26A.
Figure 26A:
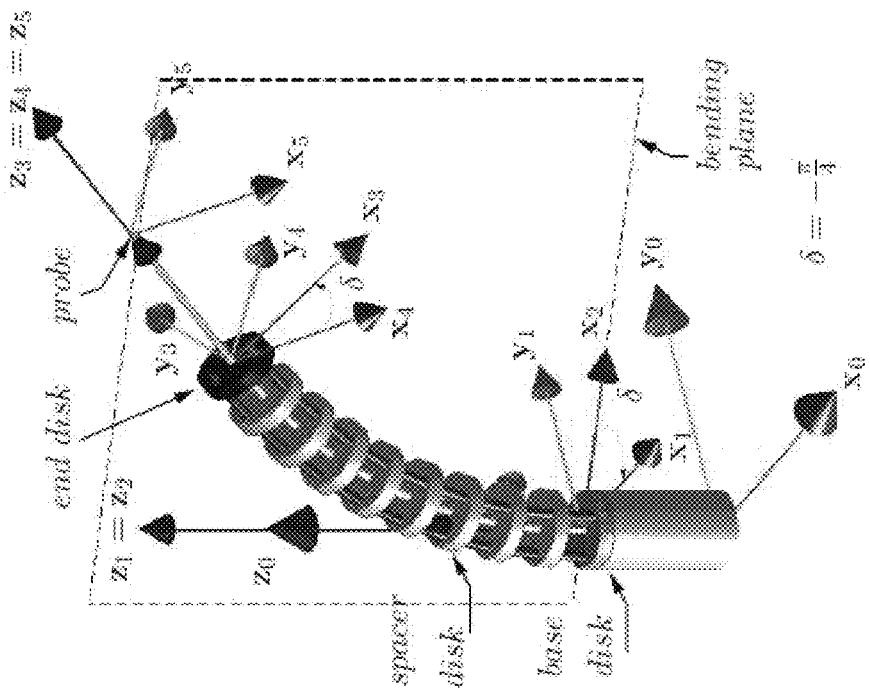
FIG. 26A is a perspective view of a posed continuum robot.

Experimental Results:

In order to validate the proposed framework, the control algorithms were implemented on the one-segment multi-backbone continuum robot of FIGS. 26A and 26B. The continuum segment is able to translate along the $\hat{z}_0$ axis providing the end-effector with a total of 3 DoFs: $q_{ins}$ and angles $\theta$ and $\delta$. The continuum segment is equipped with three load cells that monitor the forces acting on the three secondary backbones. Estimation of the $\hat{x}$ and $\hat{y}$ component of a force acting at the tip of the manipulator is possible. In the remainder of this section, multiple experiments are presented to validate the efficacy and usefulness of the proposed framework. While the motion controller always controls motion in z direction, the force controller switches between regulating a force in the $\hat{x}$ or $\hat{y}$ directions depending on the task.

The remainder of this section is organized as follows. First, the experimental setup is presented. The continuum robot manipulator and required equipment are described. Second, the estimation of uncertainties such as friction and un-modeled actuation forces are presented. Finally, three experiments are presented: force regulation in the $\hat{x}$ and $\hat{y}$ direction, shape estimation, and stiffness characterization.

The Continuum Manipulator—Direct Kinematics:

The surgical slave of FIGS. 26A and 26B is the composition of a linear stage and a two Degree of Freedom (DoF) continuum manipulator. The continuum segment has three push-pull backbones that allows for bending its end disk in space. For the ease of presentation, in the remainder of this section, the kinematics and statics of the manipulator is summarized. Six coordinate systems are defined (Figure V.4): 1) world frame $\{\hat{x}_0, \hat{y}_0, \hat{z}_0\}$, 2) segment's base disk frame $\{\hat{x}_1, \hat{y}_1, \hat{z}_1\}$, 3) segment's bending plane frame $\{\hat{x}_2, \hat{y}_2, \hat{z}_2\}$, 4) segment's end-disk frame $\{\hat{x}_3, \hat{y}_3, \hat{z}_3\}$, 5) segment's gripper frame $\{\hat{x}_4, \hat{y}_4, \hat{z}_4\}$, and 6) segment's tool frame $\{\hat{x}_5, \hat{y}_5, \hat{z}_5\}$. The position, $p_0$, and the orientation, $R^0_3$, of the tool in reference frame is given by:

$$p_5^0 = p_1^0 + R_1^0 p_3^1 + R_4^0 p_5^4$$

$$R_5^0 = R_4^0 \mathrm{Rot}(-\delta, \hat{z}) \mathrm{Rot}(\theta, \hat{y}) \mathrm{Rot}(\delta, \hat{z}) \tag{90}$$

where $R_1^0 = I$, $p_1^0 = [0\ 0\ q_{ins}]^T$, $p_3^2 = [0\ 0\ d]^T \cdot d$ is the distance between frames $\{4\}$ and $\{5\}$ (see FIGS. 26A and 26B), $p_3^1$ is the position of the end disk of the continuum segment as in II.2, $\Theta = \theta - \theta_0$, L is the nominal length of the continuum segment, $\theta_0 = \pi/2$, and operator $\mathrm{Rot}(\emptyset, \hat{w})$ returns a rotation of angle $\emptyset$ about axis $\hat{w}$. The pose of the tool is uniquely defined by configuration variables $\theta$, $\delta$, and $q_{ins}$. We, therefore, define the configuration space vector $\Psi \in \mathbb{R}^3$ as:

$$\Psi = [\theta\ \delta\ q_{ins}]^T. \tag{91}$$

In order to achieve configuration $\Psi$, the secondary backbones of the continuum robot (i=1, 2, 3) are shortened or lengthened as follows:

$$q_i = r \cos(\delta_i)(\theta - \theta_0). \tag{92}$$

where $\delta_i = \delta + (i-1)\beta$, $\beta = 2/3\pi$, and r is the radial distance of each secondary back-bone from the centrally-located back-bone. Similarly to the configuration space, we define the augmented joint-space vector $q \in \mathbb{R}^4$ as:

$$q = [q_1 \ q_2 \ q_3 \ q_{ins}]^T. \quad (93)$$

Differential Kinematics:
The tool twist $t^T = [v^T \ \omega^T]$ is given by:

$$t = J_{t\psi} \dot{\Psi} \quad (94)$$

where $\Psi$ is the rate of change of the configuration space vector $\Psi$ and $$J_{t\psi} = \begin{bmatrix} -dc_\Theta c_\delta - \frac{Lc_\delta c_\theta}{\Theta} - \frac{A_2}{\Theta^2} & -ds_\Theta s_\delta + \frac{A_1}{\Theta} & 0 \\ dc_\Theta s_\delta + \frac{Ls_\delta c_\theta}{\Theta} + \frac{A_1}{\Theta^2} & -ds_\Theta c_\delta + \frac{A_2}{\Theta} & 0 \\ ds_\Theta + \frac{Lc_\theta}{\Theta^2} - \frac{Ls_\theta}{\Theta} & 0 & 1 \\ -s_\delta & c_\delta c_\theta & 0 \\ -c_\delta & -s_\delta c_\theta & 0 \\ 0 & -1 + s_\theta & 0 \end{bmatrix}, \quad (95)$$

where $c_y = \cos(y)$, $s_y = \sin(y)$, $A_1 = L \sin(\delta)(\sin(\theta)-1)$, and $A_2 = L \cos(\delta)(\sin(\theta)-1)$. Similarly, the configuration space velocities are related to the configuration space velocities as:

$$\dot{q} = J_{q\Psi} \Psi \quad (96)$$

where $$J_{q\Psi} = \begin{bmatrix} r\cos(\delta_1) & -r\Theta\sin(\delta_1) & 0 \\ r\cos(\delta_2) & -r\Theta\sin(\delta_2) & 0 \\ r\cos(\delta_3) & -r\Theta\sin(\delta_3) & 0 \\ 0 & 0 & 1 \end{bmatrix}.$$

Statics:
Using virtual work arguments we can derived the following first order linear relationship:

$$\tilde{J}_{t\psi}^T w_e + \tilde{J}_{q\psi}^T \tau = \nabla U \quad (97)$$

where $$\tilde{J}_{t\Psi} = J_{t\Psi} \begin{bmatrix} 1 & 0 \\ 0 & 1 \\ 0 & 0 \end{bmatrix},$$

$$\tilde{J}_{q\Psi} = J_{q\Psi} \begin{bmatrix} 1 & 0 \\ 0 & 1 \\ 0 & 0 \end{bmatrix},$$

and $$\nabla U = E_Y I \begin{bmatrix} \frac{\Theta}{L} + \sum_{i=1}^{3} \frac{\Theta}{L+q_i} - \frac{\Theta^2}{2} r \sum_{i=1}^{3} \frac{\cos(\delta_i)}{(L+q_i)^2} \\ \frac{\Theta^3}{2} r \sum_{i=1}^{3} \frac{\sin(\delta_i)}{(L+q_i)^2} \end{bmatrix}.$$

Configuration Space Stiffness:
The configuration space stiffness is used for compliant motion control. Let the wrench acting on the end disk that is projected into the configuration space of the $k^{th}$ segment be given as the generalized force vector $$f_{(k)} = J_{r\psi(k)}^T w_{e,(k)}. \quad (98)$$

Applying equation (97) to the generalized force expression, the $i^{th}$ row of the generalized force $f_{(k)}$ can be written as $$f_i = \nabla U_i - [J_{q\psi}^T]_i \tau = \nabla U_i - [J_{q\psi}^{[i]}]^T \tau. \quad (99)$$

where J[i] denotes the ith column of $Jq\psi$.

For small perturbations from an equilibrium configuration, the stiffness of the individual continuum segment can be posed in the configuration space as $$\delta f = K_\psi \delta\psi \quad (100)$$

where the stiffness is given by the Jacobian of the generalized force with respect to configuration space perturbation. Thus, the elements of $K\psi$ are given by:

$$\frac{\partial f_i}{\partial \psi_j} = [K_\psi]_{ij} = \frac{\partial}{\partial \psi_j} [\nabla U_i - [J_{q\psi}^{[i]}]^T \tau]. \quad (101)$$

The elements of the stiffness matrix (equation (101)) can be expanded as $$[K_\psi]_{ij} = [H_\psi]_{ij} - \left[\frac{\partial}{\partial \psi_j}(J_{q\psi}^{[i]})\right]^T \tau - [J_{q\psi}^{[i]}]^T \frac{\partial \tau}{\partial \psi_j}. \quad (102)$$

The first term of the configuration space stiffness, $H\psi$, is the Hessian of the elastic energy of the segment given by $$H_\psi = \begin{bmatrix} \frac{\partial^2 U}{\partial \theta^2} & \frac{\partial^2 U}{\partial \theta \partial \delta} \\ \frac{\partial^2 U}{\partial \delta \partial \theta} & \frac{\partial^2 U}{\partial \delta^2} \end{bmatrix}. \quad (103)$$

The axial stiffness along the length of a given actuation line can then be expressed as $$\frac{1}{k} = \frac{1}{k_c} + \frac{1}{k_b} \quad (104)$$

where $$k_c = \frac{E_Y A}{L_c} \text{ and } k_b = \frac{E_Y A}{L_b},$$

and A denotes the cross-sectional area of the backbone.

For continuum robotic systems with remote actuation designed to access deep confined spaces, the lengths of the non-bending regions of the actuation lines far exceed that of the bending regions, $L_c \gg L_b$. The stiffness will therefore be dominated by the non-bending regions of the actuation lines. Local perturbations of the backbones at the actuation unit can be expressed as $$\frac{\partial \tau}{\partial q} = K_a \quad (105)$$

-continued where $$K_q \cong \begin{bmatrix} \frac{E_Y A}{L_c} & 0 & 0 \\ 0 & \ddots & 0 \\ 0 & 0 & \frac{E_Y A}{L_c} \end{bmatrix} \in \mathbb{R}^{m \times m} \quad (106)$$

Expanding terms by applying the chain rule and using the instantaneous inverse $\partial \tau$ kinematics, $\partial \psi$ is given by $$\frac{\partial \tau}{\partial \psi} = \frac{\partial \tau}{\partial q} \frac{\partial q}{\partial \psi} \cong K_a J_{q\psi} \quad (107)$$

The configuration space stiffness therefore reduces to $$[K_\psi]_{ij} = [H_\psi]_{ij} - \left[\frac{\partial}{\partial \psi_j}(J_{q\psi}^{[i]})\right]^T \tau - [J_{q\psi}^{[i]}]^T K_a J_{q\psi}^{[j]} \quad (108)$$

Kinematic and Static Parameters:

The numerical value of the kinematic and static parameters defined in the previous sections are reported in the table of FIG. 27. r is the radial distance from the secondary backbone to the central backbone, L is the nominal length of the continuum segment, β is the division angle between secondary backbones, $E_Y$ is the Young's modulus of the NiTi backbones, od is the outer diameter of the backbones, and $$I = \frac{\pi}{64} o_d^4 \quad (109)$$

is the second area moment of each backbone.

Estimation Uncertainties:

Uncertainties are due to: 1) deviation of the kinematic and static parameters from the nominal ones reported in the table of FIG. 27, 2) unmodeled friction along the actuation lines, 3) statics and kinematics modeling assumptions, and 4) actuation unit assembly. The robot used in this work is a 0 5 mm continuum robot with a cone that re-route the actuation lines and an actuation line length of more than 300 mm. In this work, we calibrate actuation uncertainties by populating a look-up table that depends on the configuration of the continuum manipulator.

Methods:

The continuum manipulator of FIGS. 26A and 26B is commanded to scan its workspace between $\delta=\pi/2$ and $\delta=-\pi/2$ with intervals of 5°~=0.098 rad. At each δ configuration the manipulator is bent from $\theta=\pi/2$ to $\theta=0$ with constant velocity and accomplishment time of 10 s. The discrepancy between the expected actuation forces and the sensed actuation forces was recorded.

Figure 28:
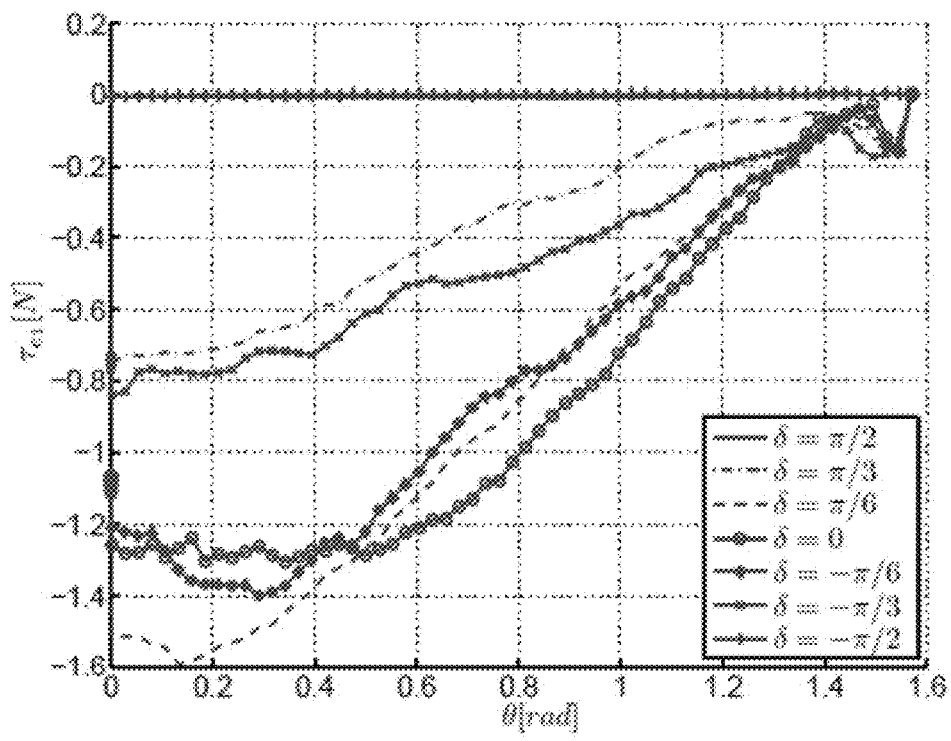
FIG. 28 is a graph of error between expected and actual actuation force on a backbone of the continuum robot of FIG. 26A as a function of bending angle.
Figure 29:
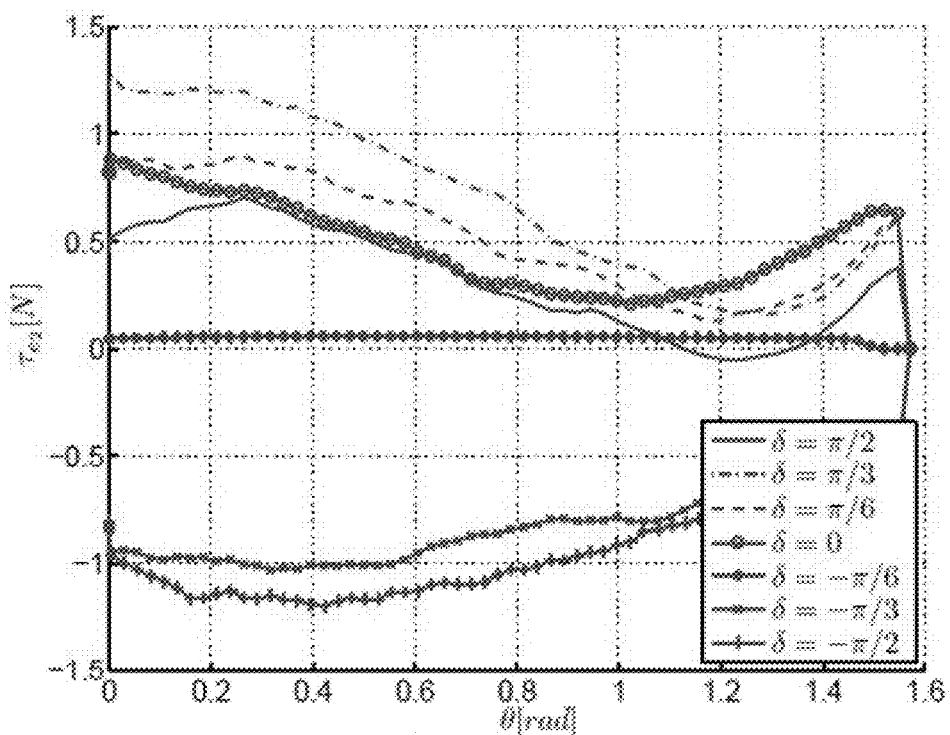
FIG. 29 is a graph of error between expected and actual actuation force on a second backbone of the continuum robot of FIG. 26A as a function of bending angle.
Figure 30:
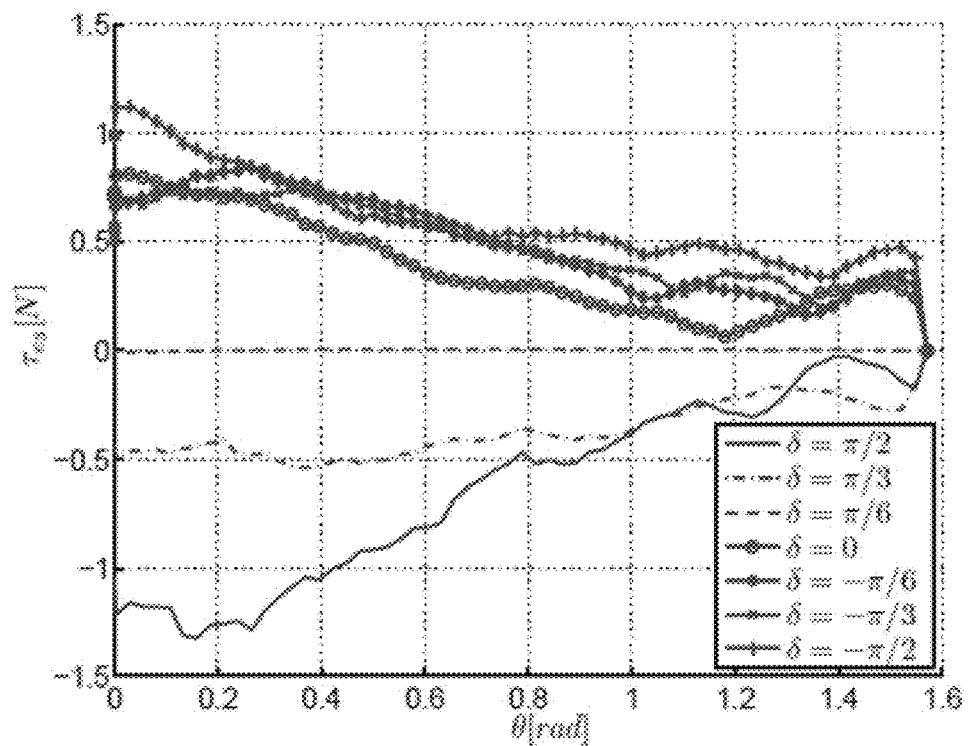
FIG. 30 is a graph of error between the expected and actual actuation force on a third backbone of the continuum robot of FIG. 26A as a function of bending angle.

Results:

FIGS. 28, 29, and 30 show the actuation force errors on backbone one, two, and three respectively. The graphs show a plot of the actuation force error versus the bending angle θ for different values of δ.

FIG. 28 shows the actuation force error, $\tau_{e1}$, associated with the first backbone. The graphs shows how the actuation force error depends on both θ and δ and, therefore, on the configuration of the manipulator. The error on backbone one reaches its minimum at $\delta=\pi/2$ and $\delta=-\pi/2$. In these two configurations backbone one is neither extended nor shortened and the load on it is, therefore, zero. In all other configurations, the error mainly increases as a function of θ but also as a function of δ.

FIG. 29 shows the actuation force error, $\tau_{e2}$, associated with the second back-bone. In this case, the minimum is reached for $\delta=-\pi/6$. In this configuration the second backbone is neither extended nor shortened and, therefore, the resultant load is zero. In all other configurations, $\tau_{e2}$, is non-zero and mainly depends on the bending angle θ. In this case, it is possible to see the effect of friction along the line. For configurations with a negative δ, backbone two is extended while for configurations with positive δ, backbone two is shortened. This phenomenon is not seen in backbone one because between $\delta \in [-\pi/2, \pi/2]$ the backbone is only shortened.

FIG. 29 shows the actuation force error, $\tau_{e3}$, associated with the third backbone. Similarly to backbone n°2, because of symmetry, the actuation force error $\tau_e$ is zero at $\delta=\pi/6$, negative for $\delta \in (\pi/6, \pi/2]$, and positive for $\delta \in [\pi/2, \pi/6)$.

Several methods can be used to characterize friction and uncertainties. In this work, we populated a lookup table using the data shown in FIGS. 28, 29, and 30. The table has a size of 36×18 and linearly interpolates over δ and θ with increments of 5°. In the current implementation, the table is only populated with data associated with negative θ, i.e. the continuum segment bends from $\theta=\pi/2$ (straight configuration) to $\theta=0$. For this reason, the compensation is not effective when the motion is reversed; thus affecting the force estimation. Although it is possible to produce velocity-dependent lookup tables, this is excluded from the scope of this work.

Figure 31:
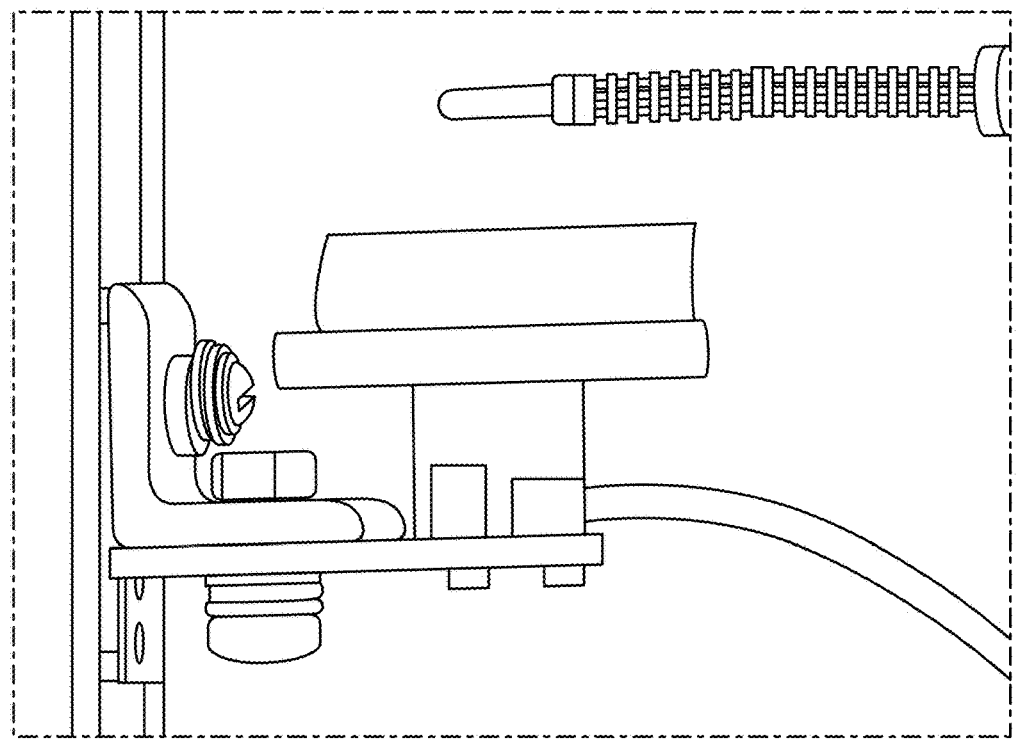
FIG. 31 is an elevation view of a continuum robot during force regulation testing.

Force Regulation:

This section presents force regulation experimental results. The goal of these experiments is to demonstrate the ability of the controller to regulate a predetermined force in both x and y directions at different configurations. As illustrated in FIG. 31, the experimental setup consists of a 5 mm continuum robot, an interaction probe with a spherical tip of 0 5 mm radius, an aluminum block, and an ATI Nano 17 for ground truth.

Methods:

In order to test the force estimation and force controller efficacy in the $\hat{x}$ direction the continuum robot is bent to the following three configurations: 1) θ=80°, δ=0°, 2) θ=60°, δ=0°, and 3) 1) θ=40°, δ=0°. At each configuration, a reference force magnitude of 5 gr, 10 gr, and 15 gr were commanded. Data from the force estimator and the ATI Nano 17 were compared and the rise time and steady state error computed.

In order to test the force estimation and force controller efficacy in the $\hat{y}$ direction the continuum robot is bent to the following configurations: 1) θ=80°, δ=0°, 2) θ=60°, δ=0°, and 3) 1) θ=40°, δ=0°. At each configuration, a reference force magnitude of 10 gr is tested. Data from the force estimator and the ATI Nano 17 are compared and the rise time and steady state error are computed.

Figure 34A:
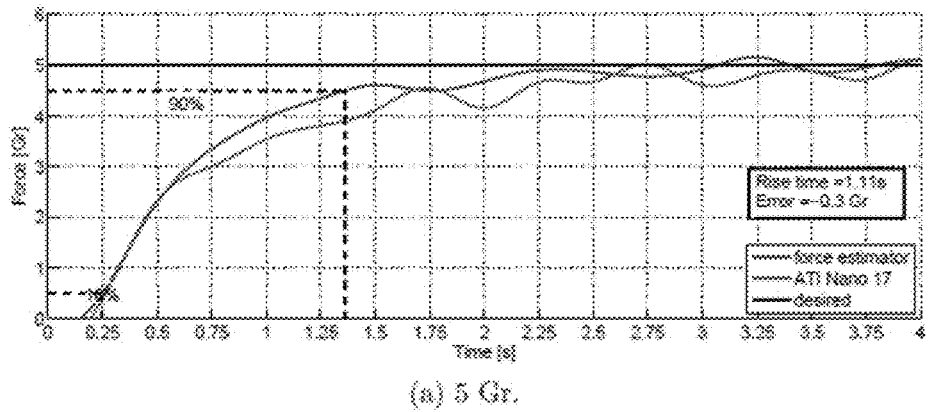
FIGS. 34A, 34B, and 34C are graphs of force step response on a silicon block in the x direction at a bend angle of 80° for three different forces.
Figure 34B:
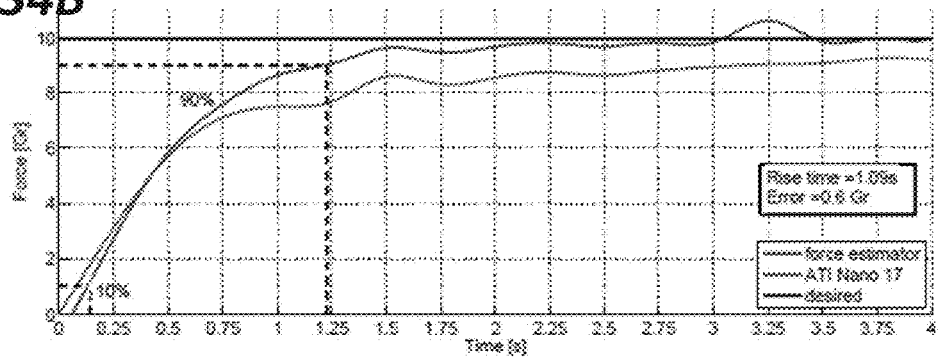
Figure 34C:
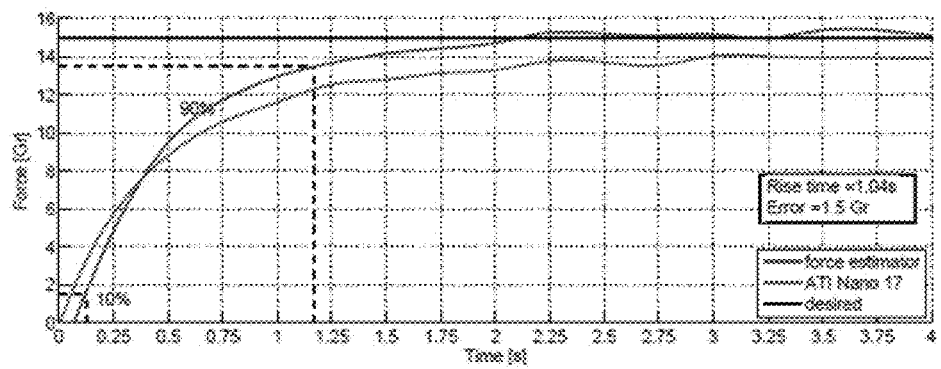
Figure 35A:
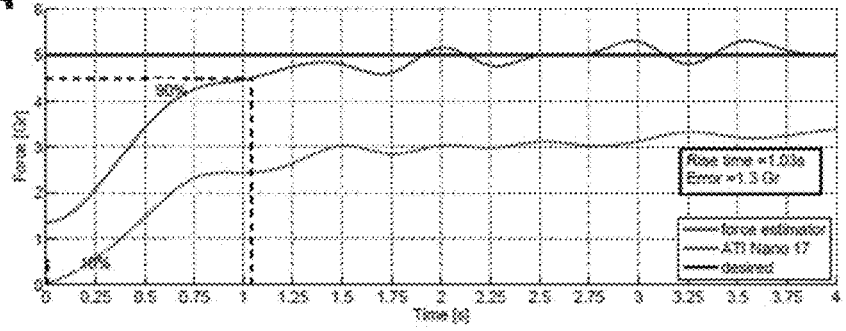
FIGS. 35A, 35B, and 35C are graphs of force step response on a silicon block in the x direction at a bend angle of 60° for three different forces.
Figure 35B:
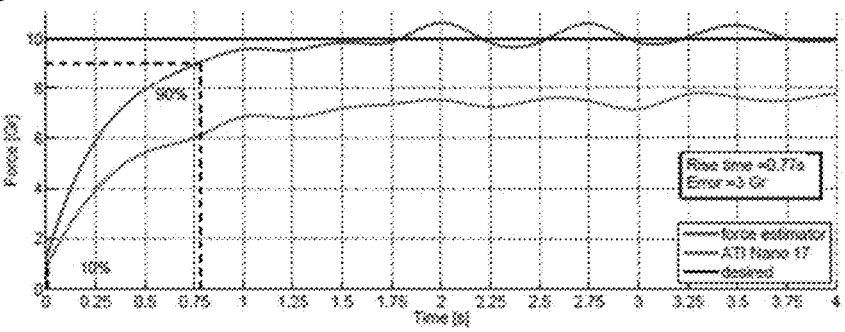
Figure 35C:
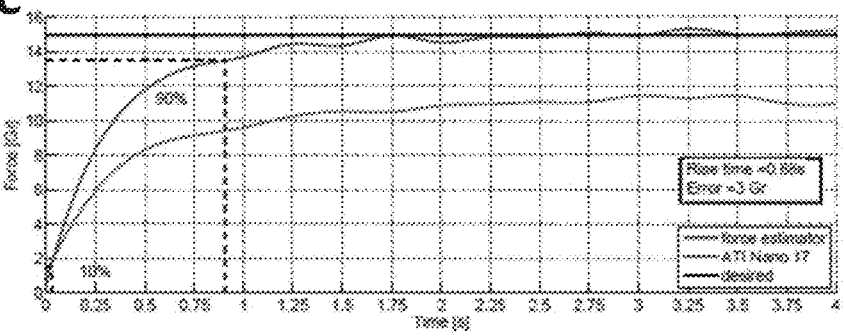
Figure 36A:
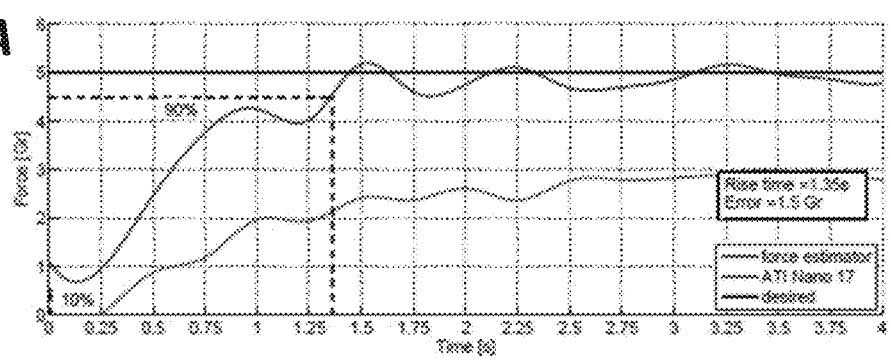
FIGS. 36A, 36B, and 36C are graphs of force step response on a silicon block in the x direction at a bend angle of 40° for three different forces.
Figure 36B:
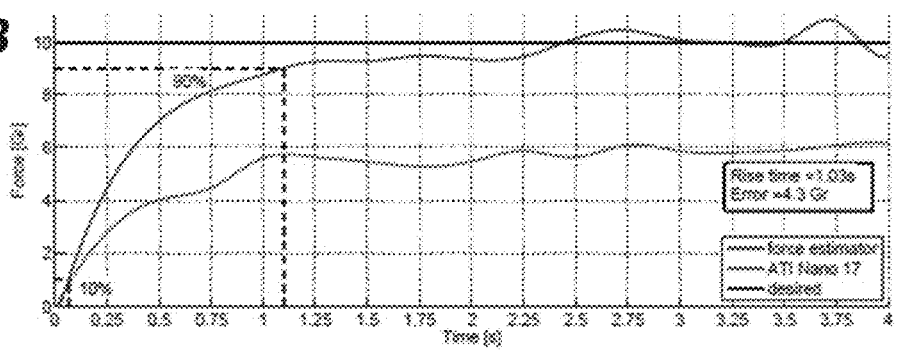
Figure 36C:
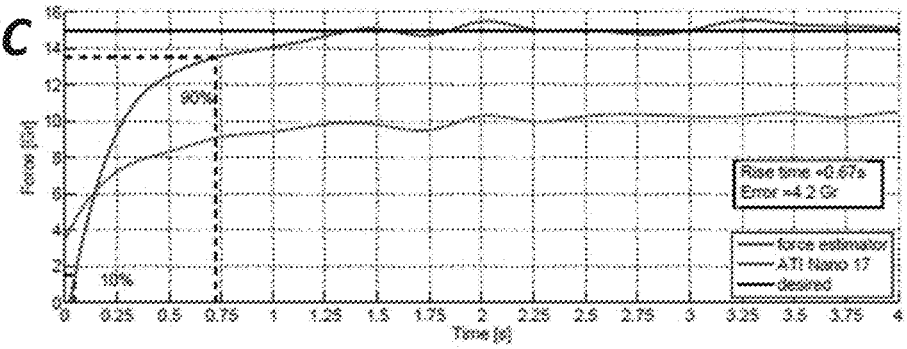

Results:

FIGS. 34A, 34B, and 34C; FIGS. 35A, 35B, and 35C; and FIGS. 36A, 36B, and 36C show the step response for force magnitudes 5 gr, 10 gr, and 15 gr in the $\hat{x}$ direction at θ=80°, θ=60°, and θ=40° respectively. Each graph shows the time history of three quantities: desired force (black), sensed force by the ATI Nano 17 (red), and sensed force by the intrinsic force estimator (blue). These results are summarized in the table of FIG. 32.

Figure 37A:
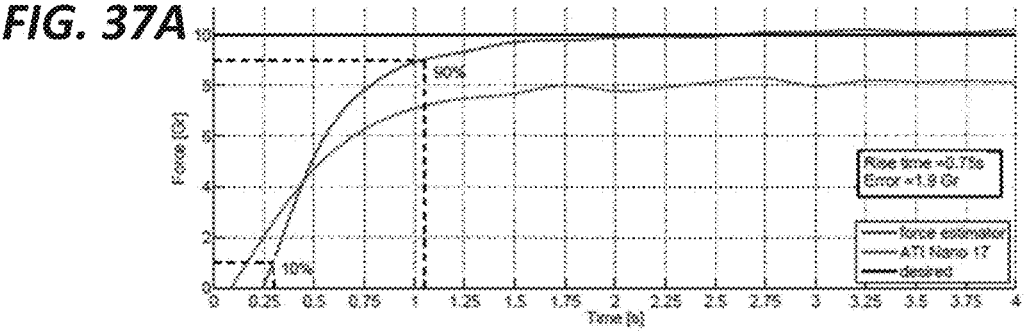
FIGS. 37A, 37B, and 37C are graphs of force step response on a silicon block in the y direction for three different starting bend angles −80°, 60°, and 40°.
Figure 37B:
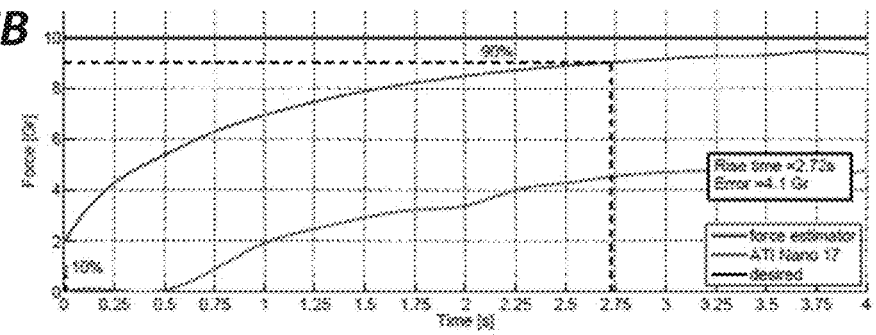
Figure 37C:
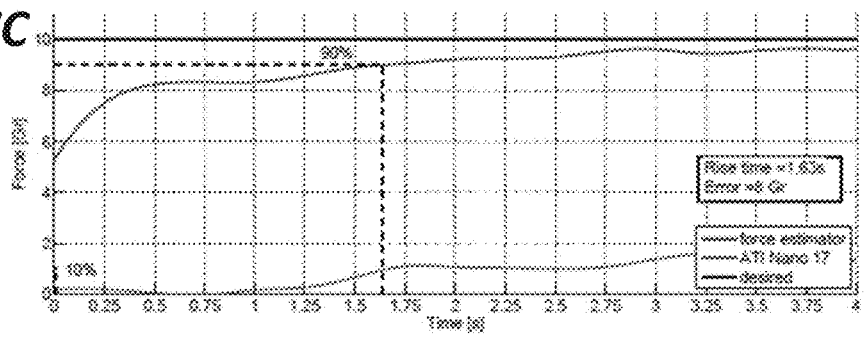

FIGS. 37A, 37B, and 37C show the step response for a force magnitude of 10 Gr in $\hat{y}$ direction at $\theta=80°$, $\theta=60°$, and $\theta=40°$. The results are summarized in the table of FIG. 33.

The experimental results demonstrate both that the hybrid motion/force control is able to regulate forces of different magnitudes in different directions and that the accuracy depends on the configuration of the manipulator. Steady state error in the x direction between the force sensed by the ATI Nano 17 and the intrinsic force estimator are mainly due to residual un-modeled uncertainties as the more energy is stored into the system ($\theta=\pi/2$ zero energy, $\theta=0$ maximum energy). These uncertainties are static and dynamic friction, bending shape, and extension/contraction of the actuation lines. Steady state error in the y direction is due to uncompensated uncertainties for side motions $\delta/=0$ and the much more compliance of the continuum manipulator in the $\delta$ direction at this particular configuration.

As shown in FIGS. 28, 29, and 30, uncertainties are symmetric depending on the configuration of the backbones. The efficacy of the intrinsic force estimator and, therefore, the force controller is definitely weaker in the $\delta$ direction. However, depending on such configuration, the x and y directions are consecutively affected in different ways. It is worth noting that the experiments were conducted on a non-calibrated robot in which geometric parameters (nominal length, distance between backbones, bending shape) and static parameters (Young's modulus, actuation line stiffness, and second moment area of all backbones) were set to the nominal value. Furthermore, the intrinsic force estimator could also undergo proper calibration as in any force/torque sensor. However, this is beyond the scope of this work in which we aim to demonstrate force control schemes for continuum robots and their use in several scenarios.

Figure 38A:
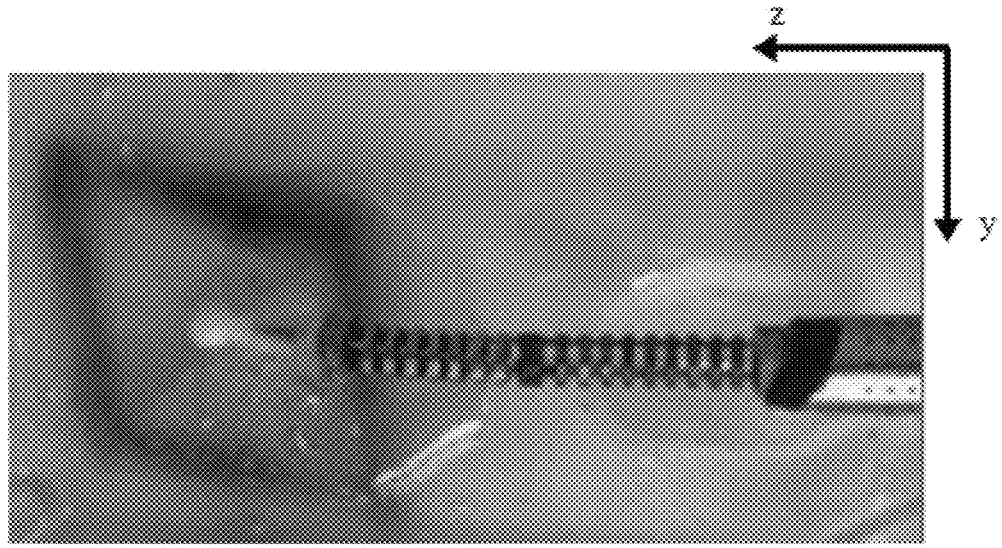
FIG. 38A is a top view of an continuum robot performing shape estimation.
Figure 38B:
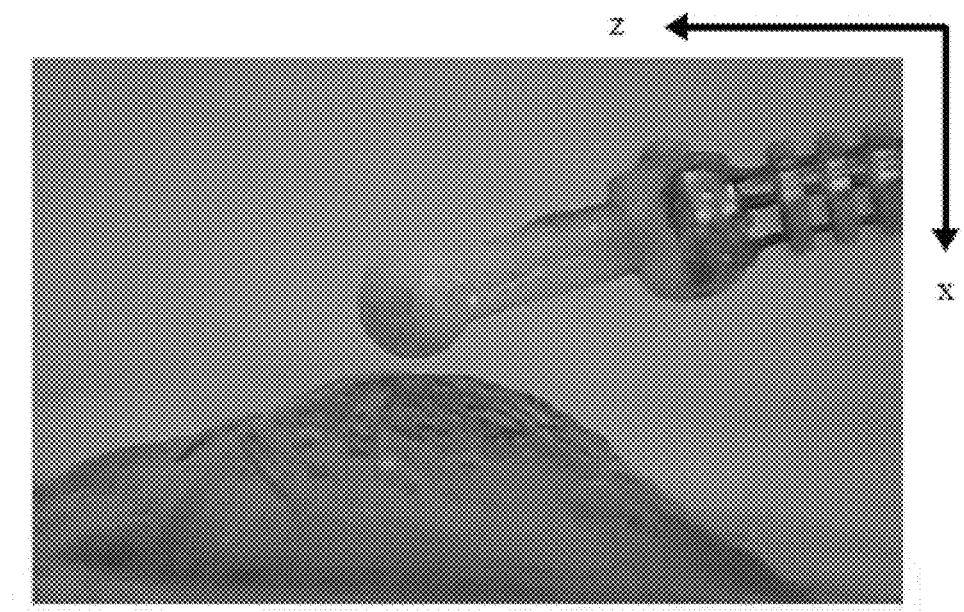
FIG. 38B is an elevation view of the continuum robot of FIG. 38A performing the shape estimation.

Force Regulated Shape Estimation:

This section presents environment's shape estimation experimental results. The goal of these experiments is to demonstrate simultaneous force and motion control. The user is able to control the end-effector while free of contact and engage the force control in pre-determined directions when in contact with the environment. FIGS. 38A and 38B illustrate the experimental setup which consists of a 5 mm continuum robot, a diamond-shape silicon phantom, an Ascension Technologies trakSTAR 2 with flat transmitter placed under the silicone phantom, and a Force Dimension Omega 7.

The experimental setup of FIGS. 38A and 38B performs shape estimation of a silicon diamond-shaped extrusion (shown in FIG. 38A). The base plane of the extrusion is placed at approximately 18 mm from the origin along the x direction (shown in FIG. 38B). The user actively controlled motion of the probe in the y and z directions. The force controller regulates a force with a magnitude of 0.1 N in the x direction.

Methods:

The 5 mm continuum robot is equipped with a plastic probe having a 5 mm radius sphere at the interaction point. The sphere reduces the impingement of the probe into the soft tissue. A 0.9 mm magnetic coil is delivered through one of the robot's working channels and secured to the probe. A silicon diamond-shaped extrusion is placed in a YZ plane at a distance of approximately 18 mm from the robot's reference frame as shown in FIGS. 38A (top view) and 38B (side view).

The end-effector's motions in the $\hat{y}$ and $\hat{z}$ directions were commanded via a Force Dimension Omega 7 with 3-axis force feedback. Position commands were sent over the Local Area Network (LAN) using User Datagram Protocol (UDP) at 100 Hz. The end-effector's position was acquired at 125 Hz using the Ascension Technology trakSTAR 2 and sent over the LAN using UDP at 100 Hz. The high-level motion and force controllers and the wrench estimator run at 200 Hz while the low-level joint controller run at 1 kHz. Switching between full motion control and hybrid motion/force control was enabled using the 7th axis of the Omega 7 (gripper).

The continuum robot, under full motion telemanipulation mode, is guided to reach a point on the silicon phantom. Once hybrid motion/force control is enabled, the continuum robot autonomously regulates a force of −0.1 N in the $\hat{x}$ direction. Position data of the probe were only collected when the sensed force in the $\hat{x}$ direction was smaller or equal to −0.05 N and the hybrid motion/force controller was engaged. These conditions ensured that each data point was actually on the surface of the sil-icon phantom. Switching between full motion/force control and hybrid motion/force control allowed to cover a workspace of 18 mm×30 mm×40 mm.

Figure 39:
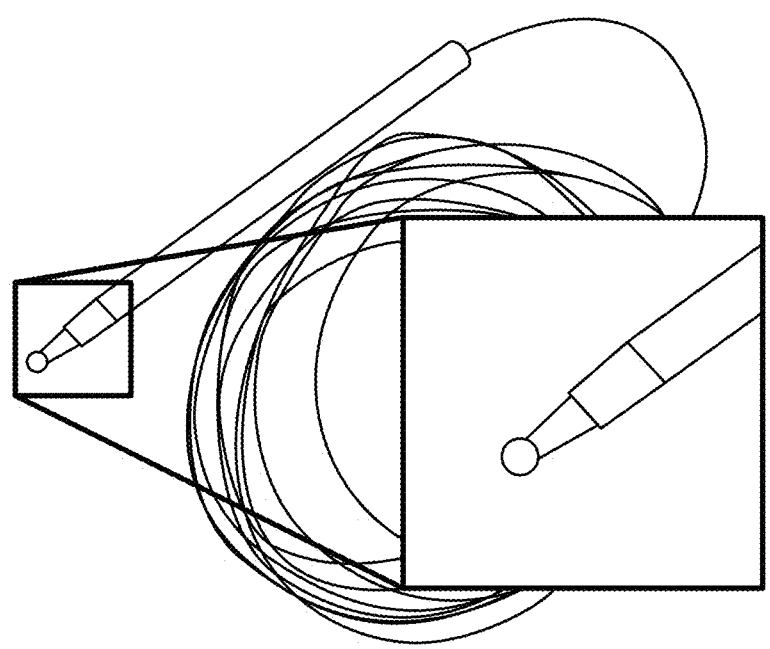
FIG. 39 is an overhead view of a probe used for a manual scan of phantom tissue.

Ground truth shape data was obtained using a second probe equipped with an-other 0 0.9 mm magnetic coil as shown in FIG. 39. The probe was manually swept over the silicon phantom and data collected. The use of an identical probe equipped with a similar sensor ensures comparison of data having the same accuracy, repeatability, noise, and uncertainties.

Position data from the electro-magnetic tracker were stored and linearly interpolated using Matlab function griddata. This function interpolates the surface at query points on the YZ plane and returns the interpolated value along the $\hat{x}$ direction. Multiple data points are automatically averaged during the interpolation.

Figure 40A:
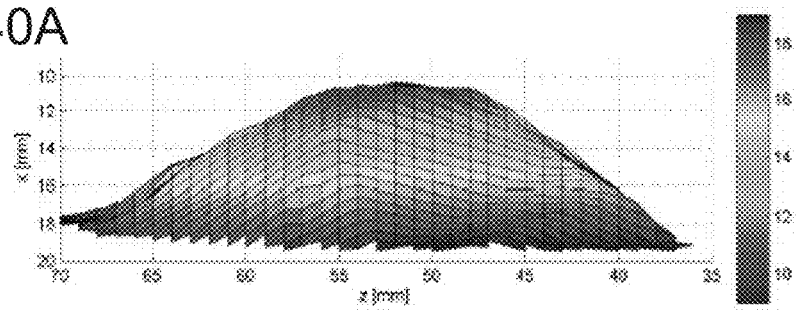
FIGS. 40A, 40B, and 40C are a series of three graphs illustrating the shape of a structure as estimated using the continuum robot of FIG. 38A from a side view, a front view, and a top view.
Figure 40B:
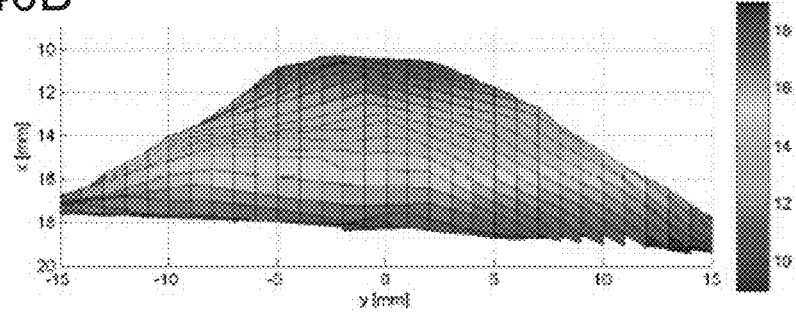
Figure 40C:
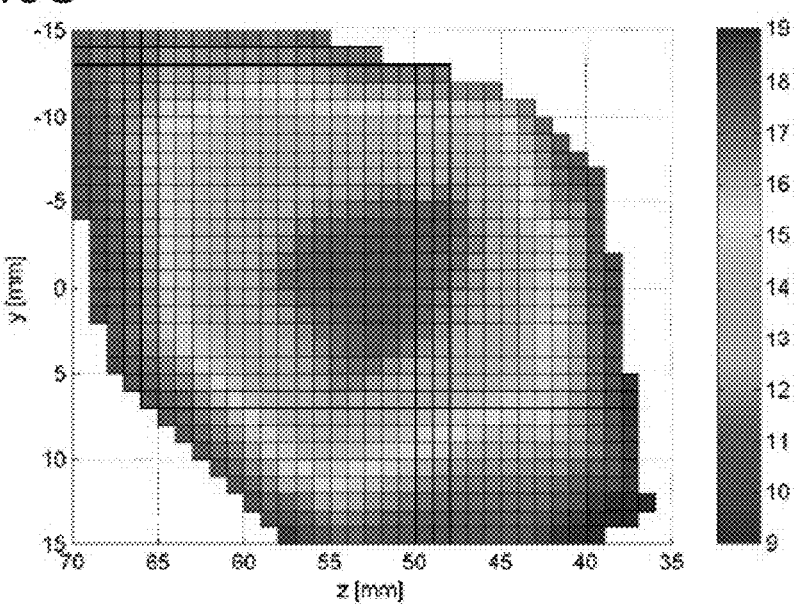
Figure 41A:
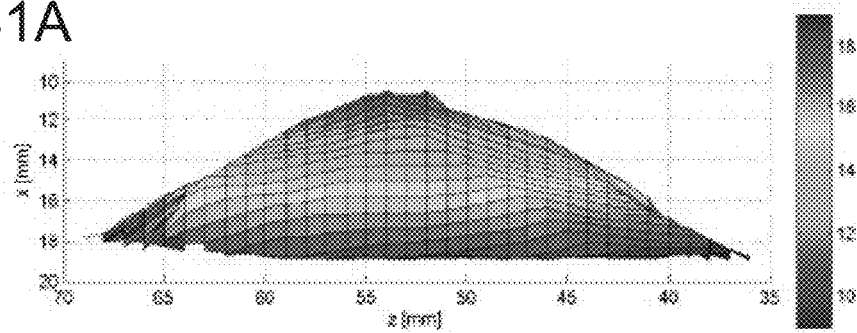
FIGS. 41A, 41B, and 41C are a series of three graphs illustrating the actual, ground truth shape of the structure measured by the continuum robot in FIG. 38A from a side view, a front view, and a top view.
Figure 41B:
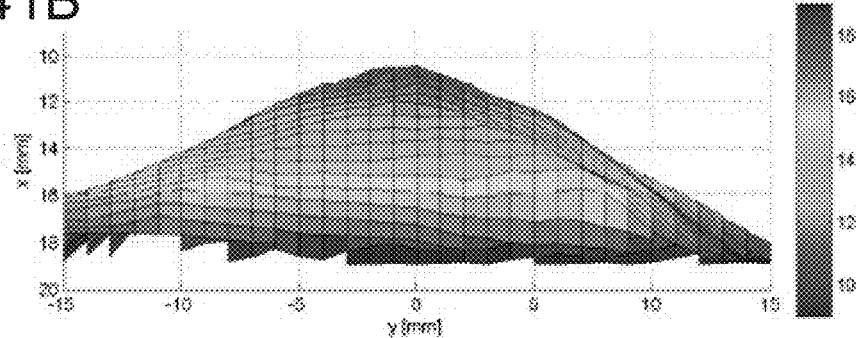
Figure 41C:
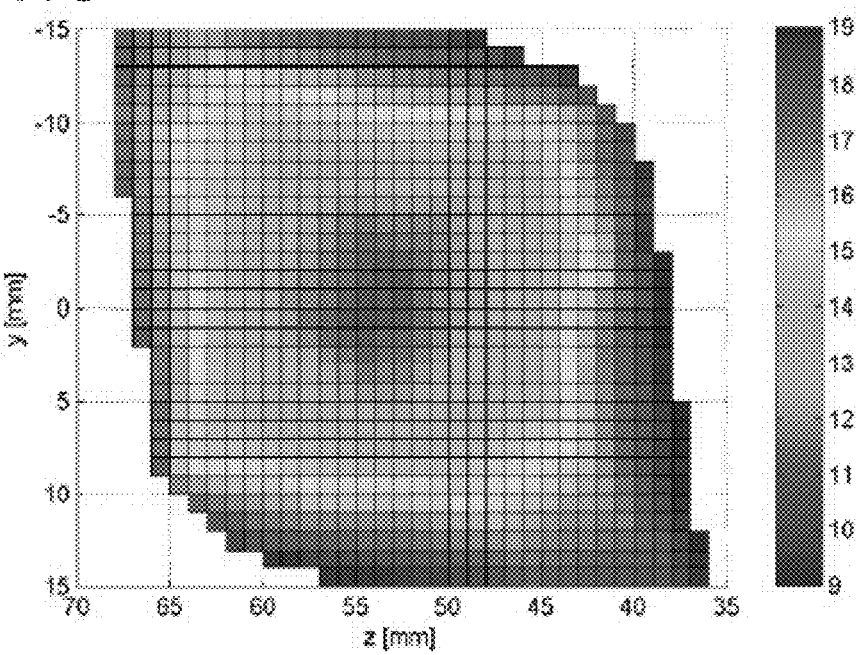
Figure 42A:
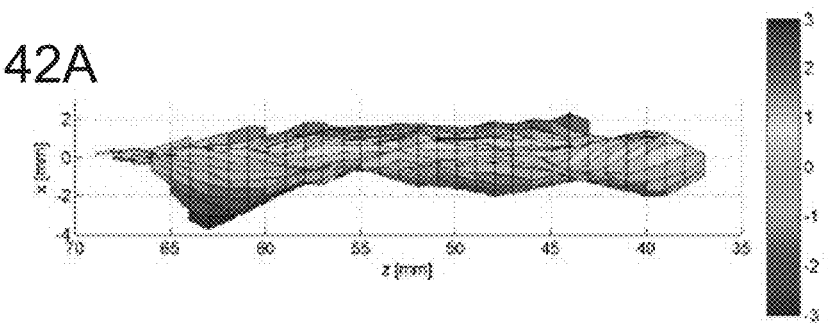
FIGS. 42A, 42B, and 42C are a series of three graphs illustrating the error between the estimated shape and the actual shape measured by the continuum robot in FIG. 38A from a side view, a front view, and a top view.
Figure 42B:
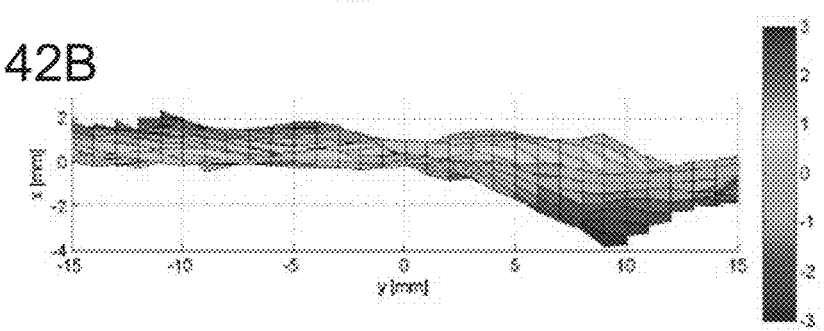
Figure 42C:
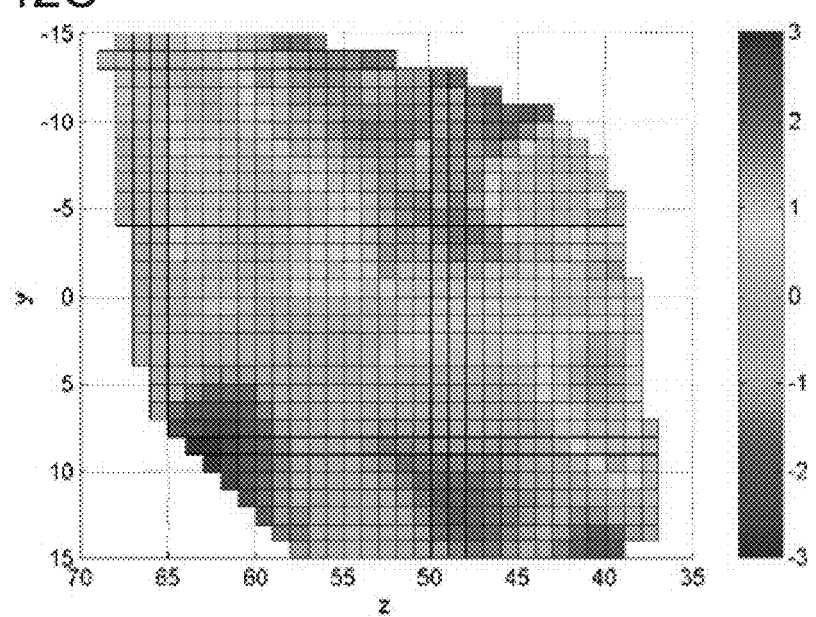

Results:

The estimated shape using the continuum robot is shown in FIGS. 40A, 40B, and 40C while the ground truth data obtained with the manual scan is shown in FIGS. 41A, 41B, and 41C. The error between the estimate shape and the ground truth shape is presented in FIGS. 42A, 42B, and 42C. As expected, the maximum deviation is found at the boundaries of the robot's workspace along the $\hat{y}$ axis. In fact, in order for the continuum segment to stretch along the $\hat{y}$ axis the bending angle $\theta$ decreases considerably and the $\delta$ angle decreases (positive $\hat{y}$) or increases (negative $\hat{y}$). As shown in the force regulation experiments reported in the previous section, the sensitivity of the force estimation in the $\hat{x}$ direction decreases considerably while the sensitivity in the $\hat{y}$ direction increases. Although the controller is unable to regulate the requested amount of force due to the force estimator, the continuum manipulator does not lose contact with the surface. This phenomenon is not seen at the boundaries of the workspace along the $\hat{z}$ direction because the insertion stage provides most of the displacement.

The very small inertia of the continuum manipulator allows the force controller to maintain contact with the unknown surface without perfect knowledge of the tangent and normal vectors at the contact point. These experiments demonstrate the efficacy of the proposed hybrid motion/force control scheme to perform independent motion and force regulation. The intrinsic compliance of the continuum manipulator also makes the impact phase stable allowing for safe and smooth transitions between full motion control and hybrid motion/force control.

Figure 43:
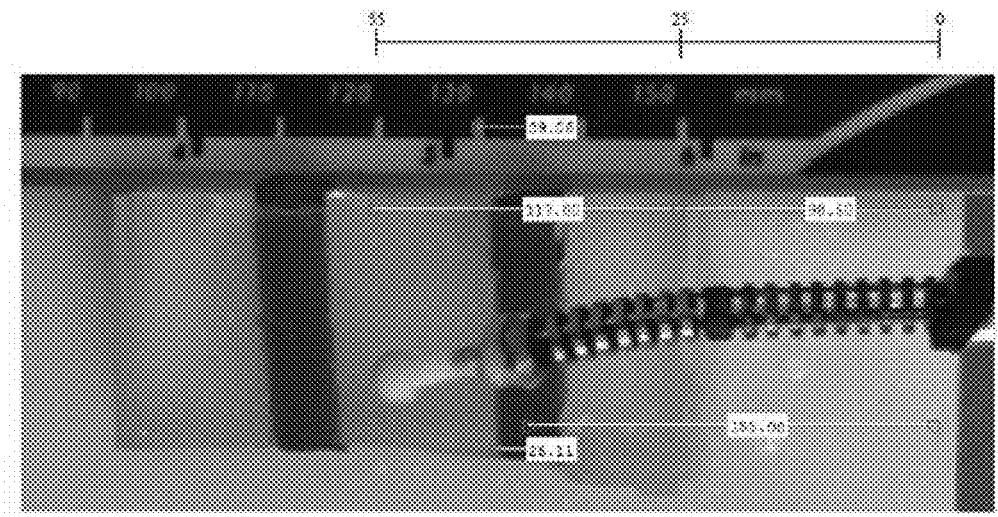
FIG. 43 is a top view of a continuum robot being used to localize a blood vessel.

Stiffness Imaging:

This section presents experimental results on stiffness characterization of soft tissues using the proposed hybrid motion/force controller. The goal of the experiment is to build a stiffness image of the surrounding environment using both position and force data. One way to build such image is to repetitively scan the surface applying different force and recording the displacement of each point between scans. FIG. 43 illustrates the experimental setup which includes a 5 mm continuum robot, a plastic probe with a spherical tip of 5 mm radius, a 0.9 mm electro-magnetic sensor, and a silicone phantom with embedded rubber tubes.

Methods:

Five consecutive surface scans were completed under hybrid motion/force control applying respectively 5 gr, 10 gr, 15 gr, 20 gr, and 25 gr. After selecting the desired force magnitude, the operator guides the robot to cover the designated area (as shown in FIG. 43). A rubber tube is embedded at approximately 155 pixels (px) from the base of the robot. Using the ruler shown in FIG. 43, it is possible to define a scaling factor between image pixels and mm. In this case, 39 px=10 mm. Using this scaling ratio, the position of the rubber tube is identified at approximately 39.7 mm from the base of the manipulator. The operator was asked to scan a rectangular area of approximately 20×30 mm.

Position data during each scan were recorded from the electro-magnetic sensor placed at the tip along with the sensed force in the $\hat{x}$ direction and smoothed by spline interpolation. Because of the position RMS of the Ascension Technologies trakSTAR 2 it was chosen to use the first and the last scan in order to obtain a better noise/signal ratio.

Figure 44:
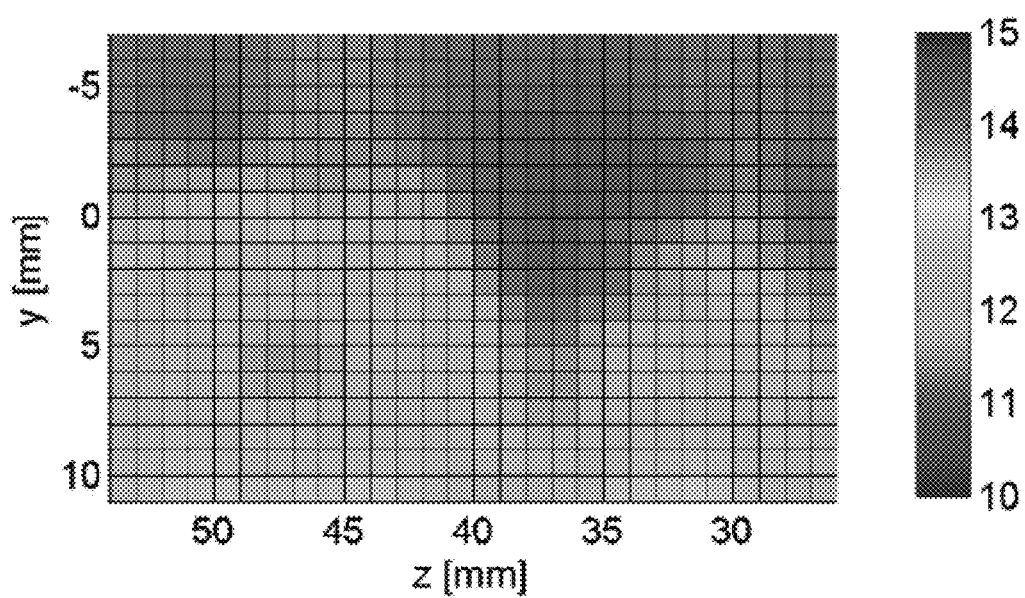
FIG. 44 is a graph illustrating the surface as estimated by the continuum robot in FIG. 43 at a first force.
Figure 45:
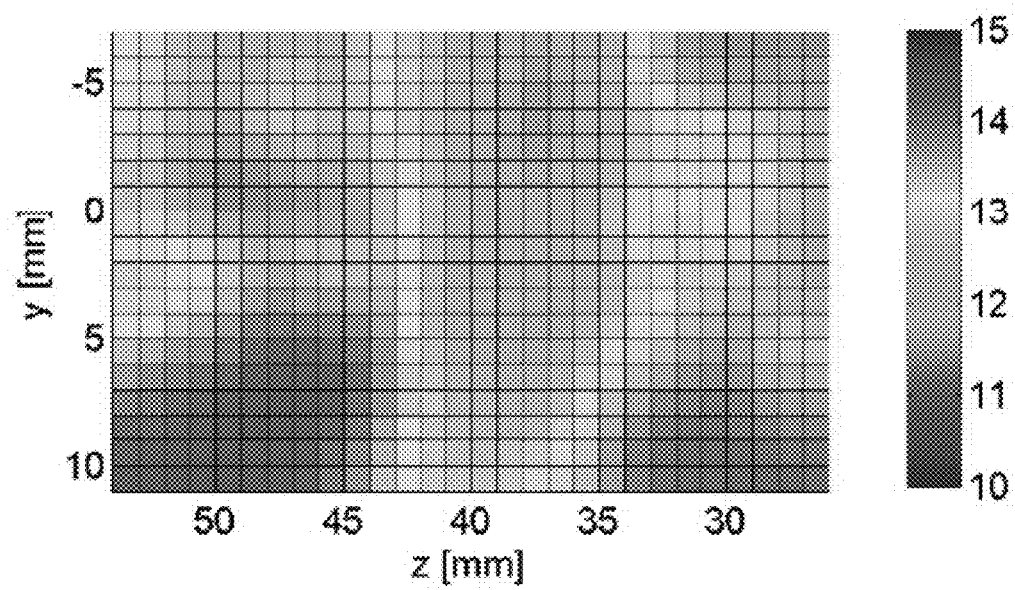
FIG. 45 is a graph illustrating the surface as estimated by the continuum robot in FIG. 43 at a second, greater force.

Results:

The estimated surfaces under 5 Gr force control and 25 Gr force control are shown in FIGS. 44 and 45. FIG. 44 shows a color map of the estimated surface with points between 10 mm and 13 mm along the x direction. FIG. 45 shows a color map of the estimated surface with points between 12 mm and 15 mm along the x direction.

Figure 46:
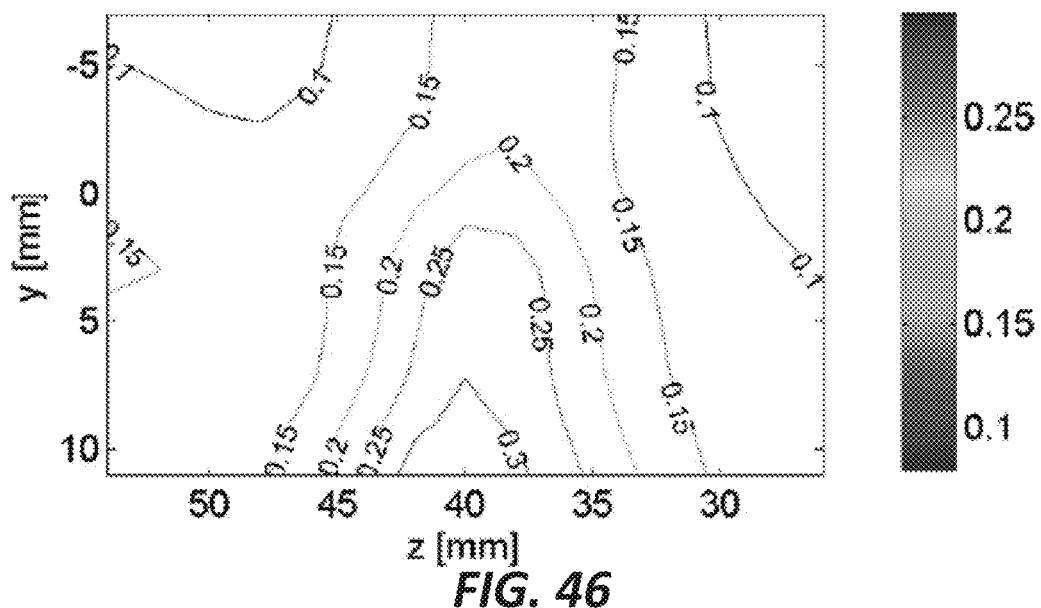
FIG. 46 is a stiffness map of the surface as estimated by the continuum robot in FIG. 43.

In order to characterize the difference in stiffness along the surface (not the absolute stiffness) a linear spring-model is used. FIG. 46 shows the estimated stiffness values across the scanned area. The graph shows a peak of 0.3 N/mm at approximately 40 mm from the base of the robot. The estimated stiffness decreases to 0.25 N/mm, 0.2 N/mm, and 0.15 N/mm respectively along both positive z direction and negative z direction. Lower stiffness is estimated at the boundaries of the scanned surface (z=55 and z=25). FIG. 43 shows that the rubber tube lays along they axis at approximately 155 px=39.7 mm from the base of the robot. The stiffness map clearly identifies high stiffness along that same axis as shown in FIG. 46.

Thus, the invention provides, among other things, systems and methods for controlling the pose of a multi-segmented continuum robot structure to adapt to the unknown dimensions of a cavity. The shape and position of the individual segments of the continuum robot are continually adjusted as the continuum robot is advanced further into the cavity, thereby providing for compliant insertion of a continuum robot into an unknown cavity. Various features and advantages of the invention are set forth in the following claims.

What is claimed is:

1. A method of controlling movement of a continuum robot and an applied force at a tip of the continuum robot, the continuum robot including a plurality of independently controlled segments along a length of the continuum robot, the method comprising the acts of:
    determining an estimated force applied by the tip of the continuum robot to a tissue surface based on measurements of loads and positions of each segment of the plurality of independently controlled segments of the continuum robot, wherein the loads of each segment includes an actuation force applied by an actuator to a segment to cause a bending of the continuum robot at the segment;
    receiving a reference position command and a force command from a user interface, the reference position command indicating a desired movement for a distal end of the continuum robot and the force command indicating a desired force to be applied by the tip of the continuum robot to a tissue surface; and
    adjusting a position of the continuum robot to cause the tip of the continuum robot to apply the desired force to the tissue surface, wherein adjusting the position of the continuum robot includes adjusting a load applied to one or more segments of the plurality of independently controlled segments based on
        the estimated force at the tip of the continuum robot,
        the reference position command, and
        the force command.

2. The method of claim 1, wherein receiving the reference position command and the force command from the user interface includes
    receiving the reference position command indicating that the desired movement of the distal end of the continuum robot is in a first direction, and
    receiving the force command indicating that a direction of the desired force to be applied by the tip of the continuum robot to the tissue surface is opposite the first direction of the desired movement of the distal end of the continuum robot.

3. The method of claim 1, wherein adjusting the position of the continuum robot includes augmenting the desired movement for the distal end of the continuum robot by
    determining a set of allowable motions for the continuum robot,
    determining a set of allowable forces for the continuum robot,
    projecting the set of allowable motions and the set of allowable forces as projection matrices into a joint space corresponding to a manipulator control,
    translating motion commands from the manipulator control into one or more task specific wrenches using an inverse of an inertia matrix, and
    translating the one or more task specific wrenches into a joint-torque vector command using a Jacobian matrix.

4. The method of claim 3, wherein adjusting the position of the continuum robot further includes regulating the force applied by the robot tip to the tissue surface to cause the force applied by the robot tip to equal a value of the desired force.

5. The method of claim 4, wherein adjusting the position of the continuum robot includes adjusting the positioning of the continuum robot based on the joint-torque vector command using a joint-space PID controller.

6. The method of claim 1, further comprising:
    determining a plurality of forces acting on the plurality of independently controlled segments along the length of the continuum robot, the plurality of forces including a generalized force acting on each segment of the plurality of segments, each force of the plurality of forces including a magnitude and a direction; and
    comparing each generalized force of the plurality of forces to a respective expected generalized force for each of the plurality of segments, the expected generalized force being based on the position of the continuum robot, wherein adjusting the position of the continuum robot including adjusting the position of each segment of the plurality of segments based on a difference between the determined generalized force and the expected generalized force for each of the plurality of segments.

7. The method of claim 6, wherein adjusting the position of the continuum robot further includes adjusting the position of each segment of the plurality of segments to minimize the difference between the determined force and the expected generalized force for each of the plurality of segments.

8. The method of claim 6, further comprising, after advancing the distal end of the continuum robot to a target location, bracing the continuum robot against surfaces of the cavity by adjusting the position of each segment of the plurality of segments to increase a difference between the determined generalized force and the expected generalized force for each of the plurality of segments until the difference reaches a threshold.

9. The method of claim 6, wherein adjusting the position of the continuum robot includes operating each of a plurality of actuators to advance or retract one of a plurality of back-bone structures relative to the continuum robot, the plurality of back-bone structures each extending through the length of the continuum robot and being coupled to at least one of the plurality of segments.

10. The method of claim 9, wherein determining a plurality of forces acting on the plurality of segments along the length of the continuum robot by the surrounding cavity includes measuring a force exerted on one of the plurality of back-bone structures by one of the plurality of actuators.

11. The method of claim 10, wherein measuring the force exerted on one of the plurality of back-bone structures includes determining a force required to hold the continuum robot in a current position while counteracting external forces acting on the plurality of segments by the surrounding cavity.

12. The method of claim 1, wherein a segment of the plurality of independent controlled segments includes an end disk,
 wherein a central backbone is fixedly coupled to the end disk and fixedly coupled to a base disk,
 wherein at least one secondary backbone is fixedly coupled to the end disk and slidably positioned through an opening in the base disk,
 wherein a load of the segment includes an actuation force applied to a proximal end of the at least one secondary backbone by an actuator, and
 wherein adjusting a position of the continuum robot includes adjusting the actuation force applied to a proximal end of the at least one secondary backbone causing the secondary backbone to slidably move through the opening in the base disk and to adjust a bending position of the end disk relative to the base disk.

* * * * *